(12) United States Patent
Lin et al.

(10) Patent No.: US 8,895,497 B2
(45) Date of Patent: Nov. 25, 2014

(54) CATHEPSIN S INHIBITORS

(75) Inventors: Chun-Cheng Lin, Fengyuan (TW);
Wun-Shaing Wayne Chang, Zhunan Township, Miaoli County (TW);
Biing-Jiun Uang, Hsinchu (TW);
Jang-Yang Chang, Taipei (TW);
Jo-Chun Chen, Taichung (TW);
Hsing-Pang Hsieh, Taipei (TW)

(73) Assignees: DCB-USA, LLC, Wilmington, DE (US); National Tsing Hua University, Hsinchu (TW); National Health Research Institutes, Miaoli (TW)

( * ) Notice: Subject to any disclaimer, the term of this patent is extended or adjusted under 35 U.S.C. 154(b) by 694 days.

(21) Appl. No.: 12/960,805

(22) Filed: Dec. 6, 2010

(65) Prior Publication Data

US 2011/0166141 A1    Jul. 7, 2011

Related U.S. Application Data

(60) Provisional application No. 61/266,877, filed on Dec. 4, 2009, provisional application No. 61/394,629, filed on Oct. 19, 2010.

(51) Int. Cl.
*C07D 295/215* (2006.01)
*C07D 307/68* (2006.01)

(52) U.S. Cl.
USPC ........................................ 514/1.1; 514/237.5

(58) Field of Classification Search
None
See application file for complete search history.

(56) References Cited

U.S. PATENT DOCUMENTS

| | | |
|---|---|---|
| 6,004,933 A | 12/1999 | Spruce et al. |
| 2003/0105099 A1 | 6/2003 | Graupe et al. |
| 2003/0119827 A1 | 6/2003 | Hickey et al. |
| 2003/0199506 A1 | 10/2003 | Li et al. |
| 2004/0072755 A1 | 4/2004 | Stennicke et al. |
| 2006/0018831 A1 | 1/2006 | Birger et al. |
| 2006/0111303 A1 | 5/2006 | Hatayama et al. |
| 2007/0117785 A1 | 5/2007 | Butler et al. |
| 2007/0141059 A1 | 6/2007 | Elrod |
| 2008/0103149 A1 | 5/2008 | Guedat et al. |
| 2008/0200454 A1 | 8/2008 | Ameriks et al. |
| 2008/0207683 A1 | 8/2008 | Allen et al. |
| 2008/0269241 A1 | 10/2008 | Allen et al. |
| 2009/0099157 A1 | 4/2009 | Ameriks et al. |
| 2009/0118274 A1 | 5/2009 | Allen et al. |

FOREIGN PATENT DOCUMENTS

| | | |
|---|---|---|
| WO | WO96/30353 | 10/1996 |
| WO | WO98/49190 | 11/1998 |
| WO | WO99/54317 | 10/1999 |
| WO | WO02/100849 | 12/2002 |
| WO | WO2004/007557 | 1/2004 |
| WO | WO2004/064870 | 8/2004 |
| WO | WO2005/040142 | 5/2005 |
| WO | WO2006/050930 | 5/2006 |
| WO | WO2007/066200 | 6/2007 |
| WO | WO2008/053301 | 5/2008 |
| WO | WO2008/100618 | 8/2008 |
| WO | WO2008/100620 | 8/2008 |
| WO | WO2008/100621 | 8/2008 |
| WO | WO2008/100622 | 8/2008 |
| WO | WO2008/100635 | 8/2008 |
| WO | WO 2009/136997 | * 11/2009 |
| WO | WO2009/136997 | 11/2009 |

OTHER PUBLICATIONS

Liu, Hong et al., Design and Synthesis of Arylaminoethyl Amides as Noncovalent Inhibitors of Cathepsin S. Part 1, Bioorganic & Medicinal Chemistry Letters vol. 15, pp. 4979-4984 (2005).

Loser, Reik et al., Antimalarial Activity of Azadipeptide Nitriles, Bioorganic &Medicinal Chemistry Letters, vol. 20, pp. 252-255 (2009).

Ward, Yancey D. et al., Design and Synthesis of Dipeptide Nitriles as Reversible and Potent Cathepsin S Inhibitors, 1. Med. Chem., vol. 45, pp. 5471-5482 (2002).

Chen, Jo-Chun et al., Design and Synthesis of α-Ketoamides as Cathepsin S Inhibitors with Potential Applications against Tumor Invasion and Angiogenesis; J. Med. Chem. 53(11):4545-4549 (2010).

* cited by examiner

*Primary Examiner* — Karlheinz R Skowronek
*Assistant Examiner* — Roy Teller
(74) *Attorney, Agent, or Firm* — Cesari and McKenna, LLP

(57) ABSTRACT

Cathepsin S inhibitors having formula (I), (II), (III) or (IV) as shown in the specification. These inhibitors can be used to treat cancer and autoimmune/inflammatory diseases.

14 Claims, No Drawings

CATHEPSIN S INHIBITORS

CROSS REFERENCE TO RELATED APPLICATIONS

This application claims the benefit of the priority pursuant to 35 U.S.C. §119(e) of U.S. Provisional Application Ser. Nos. 61/266,877, filed on Dec. 4, 2009, and 61/394,629, filed Oct. 19, 2010. The contents of both prior applications are incorporated herein by reference.

BACKGROUND

Cathepsin S (CTSS), a proteolytic enzyme, plays an essential role in the major histocompatibility complex (MHC) class II antigen presentation pathway. Specifically, this enzyme degrades the invariant chain (a MHC class II chaperone) prior to its removal from the MHC class II peptide-binding cleft. This facilitates loading of antigenic amide compounds to MHC class II αβ-dimers and subsequent transportation of the complex to the cell surface to initiate MHC class II restricted CD4+ T-cell recognition. See Pierre and Mellman, *Cell* 1998, 93, 1135-1145. It has been found that CTSS is associated with autoimmune and inflammatory diseases, such as asthma, allergy, atherosclerosis, emphysema, and rheumatoid arthritis.

CTSS also participates in dissolution and remodelling of connective tissue and basement membranes in tumor growth, invasion, and metastasis. See Sloane et al., *Biochemical and Molecular Aspects of selected Cancers*, 1994, 411-466, Academic Press, New York Inhibition of this enzyme has been reported to be effective in treating cancers. See Reise et al., Immunity 1996, 4, 357-366 and Liu et al., Drug News Prespect 2004, 17, 357-363.

SUMMARY

This invention is based on the discovery that certain amide compounds are effective in inhibiting CTSS.

In one aspect, this invention features amide compounds of formula (I):

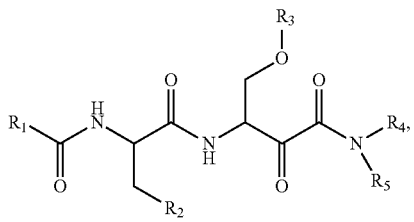

wherein $R_1$ is H, alkyl, alkenyl, alkynyl, cycloalkyl, cycloalkenyl, heterocycloalkyl, heterocycloalkenyl, aryl, heteroaryl, $OR_a$, $SR_a$, $NR_aR_b$, $N(R_a)C(O)R_b$, $N(R_a)C(O)OR_b$, $C(O)R_a$, $COOR_a$, $OC(O)R_a$, $C(S)R_a$, $C(O)NR_aR_b$, $C(S)NR_aR_b$, $N(R_a)C(S)R_b$, or $N(R_a)N(R_b)C(O)R_c$, in which each of $R_a$, $R_b$, and $R_c$, independently, is H, alkyl, alkenyl, alkynyl, cycloalkyl, cycloalkenyl, heterocycloalkyl, heterocycloalkenyl, aryl, or heteroaryl, or $R_a$ and $R_b$ together with the nitrogen atom or nitrogen atoms to which they are attached form heterocycloalkyl, heterocycloalkenyl, or heteroaryl; each of $R_2$ and $R_3$, independently, is H, cycloalkyl, cycloalkenyl, heterocycloalkyl, heterocycloalkenyl, aryl, heteroaryl, or alkyl optionally substituted with cycloalkyl, cycloalkenyl, heterocycloalkyl, heterocycloalkenyl, aryl, or heteroaryl; and each of $R_4$ and $R_5$, independently, is H, alkyl, alkenyl, alkynyl, cycloalkyl, cycloalkenyl, heterocycloalkyl, heterocycloalkenyl, aryl, or heteroaryl, or $R_4$ and $R_5$ together with the nitrogen atom to which they are attached form heterocycloalkyl, heterocycloalkenyl, or heteroaryl.

Referring to formula (I), the compounds may have one or more of the following features: (i) $R_2$ is cycloalkyl (e.g., cyclohexyl) or aryl (e.g., phenyl), (ii) $R_3$ is alkyl optionally substituted with cycloalkyl, heterocycloalkyl, aryl, or heteroaryl (e.g., benzyl), and (iii) one of $R_4$ and $R_5$ is H and the other of $R_4$ and $R_5$ is cycloalkyl, cycloalkenyl, heterocycloalkyl, heterocycloalkenyl, aryl, or heteroaryl, or alkyl optionally substituted with cycloalkyl, cycloalkenyl, heterocycloalkyl, heterocycloalkenyl, aryl, heteroaryl, $OR_d$, $C(O)R_d$, $COOR_d$, or $OC(O)R_d$, in which $R_d$ is H, alkyl, alkenyl, alkynyl, cycloalkyl, cycloalkenyl, heterocycloalkyl, heterocycloalkenyl, aryl, or heteroaryl (e.g., alkyl optionally substituted with aryl or $COOR_d$, or phenyl optionally substituted with halo or fused with heterocycloalkyl).

Some of the compounds of formula (I) has the following stereochemistry:

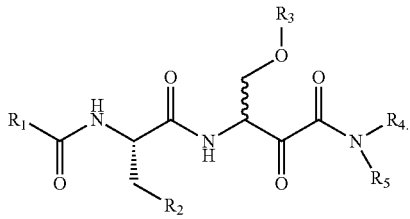

In another aspect, this invention features amide compounds of formula (II):

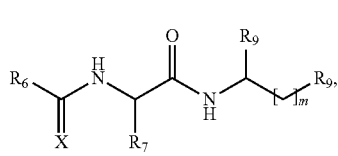

wherein m is 0, 1, 2, or 3; X is O or S; $R_6$ is cycloalkyl, cycloalkenyl, heteroaryl, or $NR_aR_b$, each of $R_a$ and $R_b$, independently, being H, alkyl, alkenyl, alkynyl, cycloalkyl, cycloalkenyl, heterocycloalkyl, heterocycloalkenyl, aryl, or heteroaryl; $R_7$ is cycloalkyl, cycloalkenyl, heterocycloalkyl, heterocycloalkenyl, aryl, heteroaryl, or alkyl substituted with cycloalkyl, cycloalkenyl, heterocycloalkyl, heterocycloalkenyl, aryl, or heteroaryl; $R_8$ is H, alkyl, alkenyl, alkynyl, cycloalkyl, cycloalkenyl, heterocycloalkyl, heterocycloalkenyl, aryl, or heteroaryl, and $R_9$ is cycloalkyl, cycloalkenyl, heterocycloalkyl, heterocycloalkenyl, aryl, heteroaryl, $OR_c$, CN, $CONR_cR_d$, $CON(R_c)NR_dR_e$, $C=NNR_dR_e$, $N(R_e)NR_dR_e$, or alkenyl substituted with $COOR_e$, in which each of $R_c$ and $R_d$, independently, is H, alkyl, alkenyl, alkynyl, cycloalkyl, cycloalkenyl, heterocycloalkyl, heterocycloalkenyl, aryl, or heteroaryl, or $R_c$ and $R_d$ together with the nitrogen atom or nitrogen atoms to which they are attached form heterocycloalkyl, heterocycloalkenyl, or heteroaryl, and $R_e$ is CN, $C(O)R_f$, $C(S)R_f$, $C(O)NR_fR_g$, $C(S)NR_fR_g$, each of $R_f$ and $R_g$, independently, being H, alkyl, alkenyl, alkynyl, cycloalkyl, cycloalkenyl, heterocycloalkyl, heterocycloalkenyl, aryl, or heteroaryl, or $R_f$ and $R_g$ together with the nitrogen atom to which they are attached forming heterocycloalkyl, heterocycloalkenyl, or heteroaryl.

Referring to formula (II), the compounds may have one or both of the following features: (i) $R_6$ is heteroaryl (e.g., pyrazinyl) and (ii) $R_9$ is $CON(R_c)NR_dR_e$ or $CONR_cR_d$.

Some of the compounds of formula (II) has the following stereochemistry:

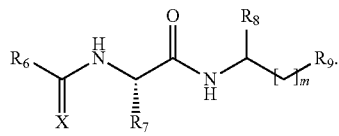

In still another aspect, this invention features amide compounds of formula (III):

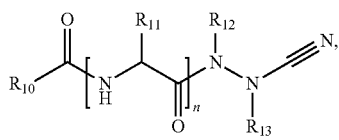

(III)

wherein n is 1, 2, or 3; $R_{10}$ is aryl, heteroaryl, alkoxy, aryloxy, or heteroaryloxy; $R_{11}$ is cycloalkyl, cycloalkenyl, heterocycloalkyl, heterocycloalkenyl, aryl, heteroaryl, or alkyl substituted with cycloalkyl, cycloalkenyl, heterocycloalkyl, heterocycloalkenyl, aryl, or heteroaryl; and each of $R_{12}$ and $R_{13}$, independently, is H, alkyl, alkenyl, alkynyl, cycloalkyl, cycloalkenyl, heterocycloalkyl, heterocycloalkenyl, aryl, or heteroaryl when $R_{10}$ is alkoxy; or each of $R_{12}$ and $R_{13}$, independently, is H, alkyl, alkenyl, alkynyl, cycloalkyl, cycloalkenyl, heterocycloalkyl, heterocycloalkenyl, aryl, or heteroaryl, or $R_{12}$ and $R_{13}$ together with the nitrogen atoms to which they are attached form heterocycloalkyl, heterocycloalkenyl, or heteroaryl when $R_{10}$ is aryl, heteroaryl, aryloxy, or heteroaryloxy.

Some of the compounds of formula (III) has the following stereochemistry:

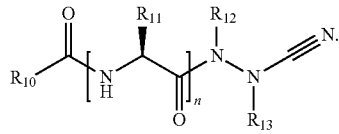

In still another aspect, this invention features amide compounds of formula (IV):

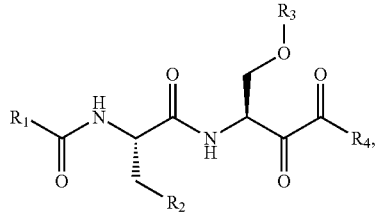

(IV)

wherein each of $R_1$ and $R_2$, independently, alkyl, alkoxyalkyl, acyl, cycloalkyl, aryl, heteroaryl, heterocycloalkyl, cycloalkylalkyl, aralkyl, heteroaralkyl, or heterocycloalkylalkyl; $R_3$ is cycloalkyl, aryl, heteroaryl, heterocycloalkyl, cycloalkylalkyl, aralkyl, heteroaralkyl, or heterocycloalkylalkyl; and $R_4$ alkyl, alkoxyalkyl, acyl, amino, cycloalkyl, aryl, heteroaryl, heterocycloalkyl, cycloalkylalkyl, aralkyl, heteroaralkyl, or heterocycloalkylalkyl.

Referring to formula (IV), the compounds may feature that $R_1$ is one of the following moieties:

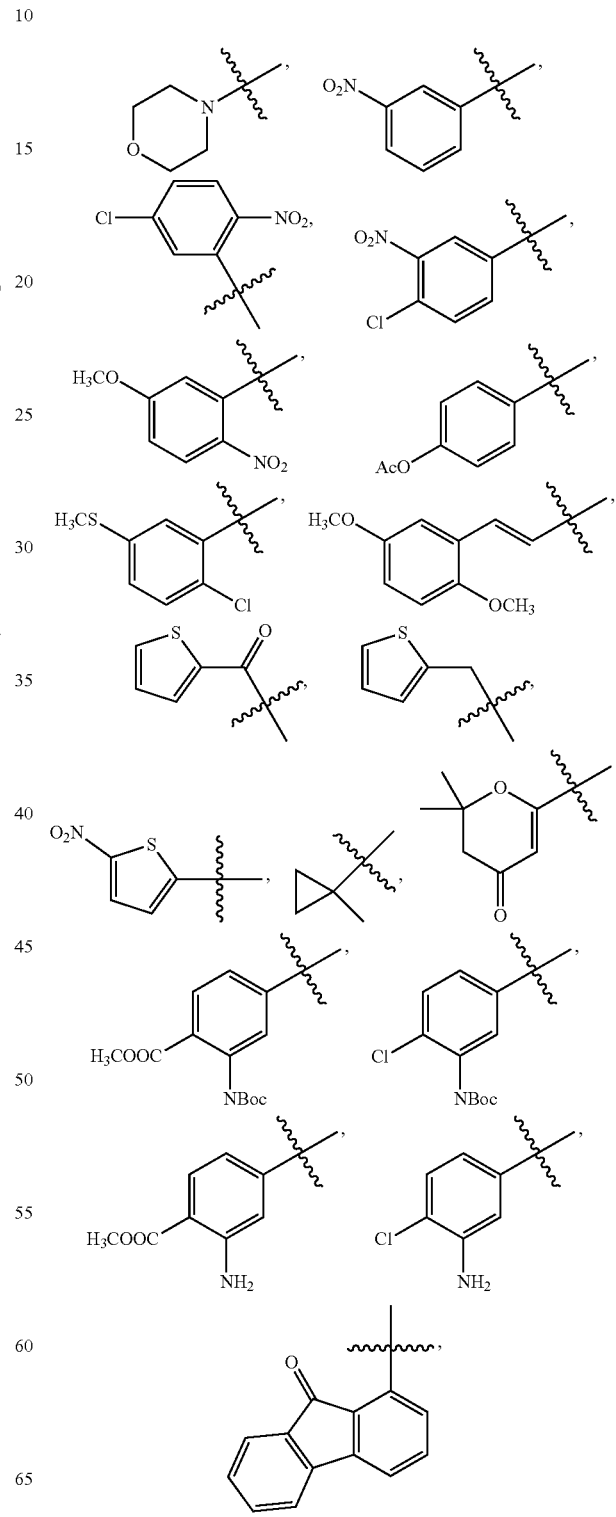

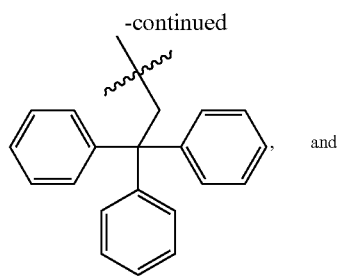

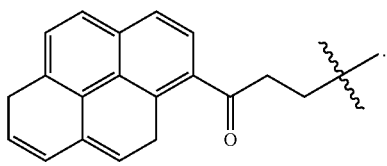

The term "alkyl" refers to a saturated, linear or branched hydrocarbon moiety, such as —CH$_3$ or —CH(CH$_3$)$_2$. The term "alkenyl" refers to a linear or branched hydrocarbon moiety that contains at least one double bond, such as —CH═CH—CH$_3$. The term "alkynyl" refers to a linear or branched hydrocarbon moiety that contains at least one triple bond, such as —C≡C—CH$_3$. The term "cycloalkyl" refers to a saturated, cyclic hydrocarbon moiety, such as cyclohexyl. The term "cycloalkenyl" refers to a non-aromatic, cyclic hydrocarbon moiety that contains at least one double bond, such as cyclohexenyl. The term "heterocycloalkyl" refers to a saturated, cyclic moiety having at least one ring heteroatom (e.g., N, O, or S), such as 4-tetrahydropyranyl. The term "heterocycloalkenyl" refers to a non-aromatic, cyclic moiety having at least one ring heteroatom (e.g., N, O, or S) and at least one ring double bond, such as pyranyl. The term "aryl" refers to a hydrocarbon moiety having one or more aromatic rings. Examples of aryl moieties include phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

Alkyl, alkenyl, alkynyl, cycloalkyl, cycloalkenyl, heterocycloalkyl, heterocycloalkenyl, aryl, and heteroaryl mentioned herein include both substituted and unsubstituted moieties, unless specified otherwise. Possible substituents on cycloalkyl, cycloalkenyl, heterocycloalkyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

In yet another aspect, this invention features a method for treating cancer or autoimmune/inflammatory disease. The method includes administering to a subject in need thereof an effective amount of one or more amide compounds of formula (I), (II), or (III) shown above. The term "cancer" refers to cellular tumor. Cancer cells have the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type, or stage of invasiveness. Examples of cancer include, but are not limited to, carcinoma and sarcoma such as leukemia, sarcoma, osteosarcoma, lymphomas, melanoma, glioma, pheochromocytoma, hepatoma, ovarian cancer, skin cancer, testicular cancer, gastric cancer, pancreatic cancer, renal cancer, breast cancer, prostate cancer, colorectal cancer, cancer of head and neck, brain cancer, esophageal cancer, bladder cancer, adrenal cortical cancer, lung cancer, bronchus cancer, endometrial cancer, nasopharyngeal cancer, cervical or liver cancer, and cancer of unknown primary site.

In addition, this invention encompasses a pharmaceutical composition that contains an effective amount of at least one of the above-mentioned amide compounds and a pharmaceutically acceptable carrier.

Also within the scope of this invention is a composition containing one or more of the amide compounds described above for use in treating an above-described disease, and the use of such a composition for the manufacture of a medicament for the just-mentioned treatment.

The details of one or more embodiments of the invention are set forth in the description below. Other features, objects, and advantages of the invention will be apparent from the description and from the claims.

DETAILED DESCRIPTION

Shown below are the exemplary compounds of this invention:

Compound 1

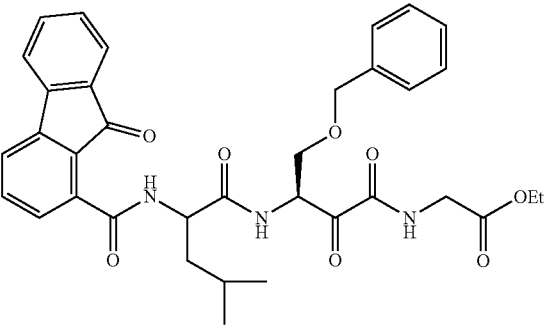

TABLE 1
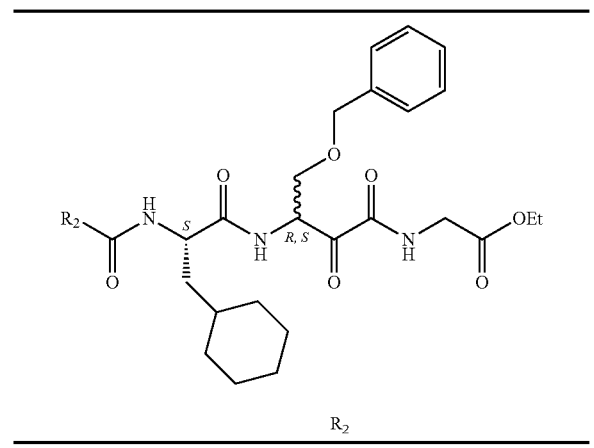
| | $R_2$ |
|---|---|
| 2 | 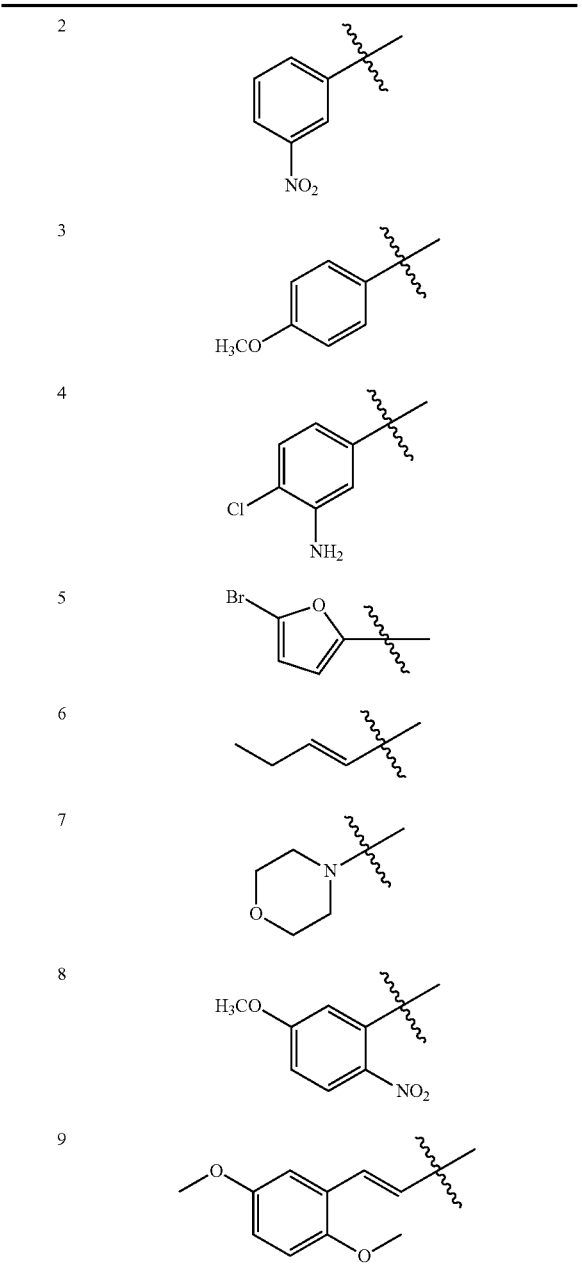 |
| 3 | |
| 4 | |
| 5 | |
| 6 | |
| 7 | |
| 8 | |
| 9 | |
TABLE 1-continued
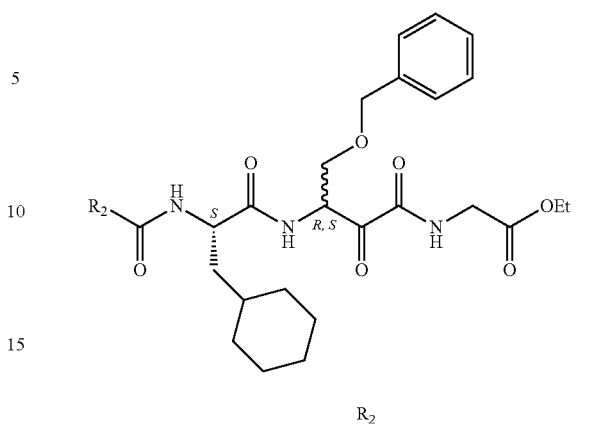
| | $R_2$ |
|---|---|
| 10 | 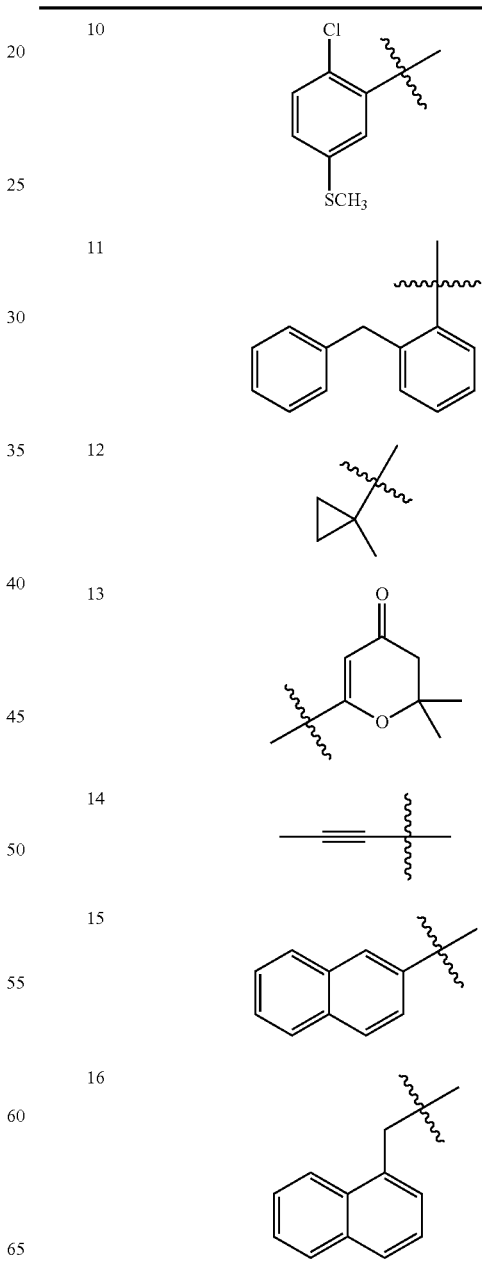 |
| 11 | |
| 12 | |
| 13 | |
| 14 | |
| 15 | |
| 16 | |

TABLE 1-continued
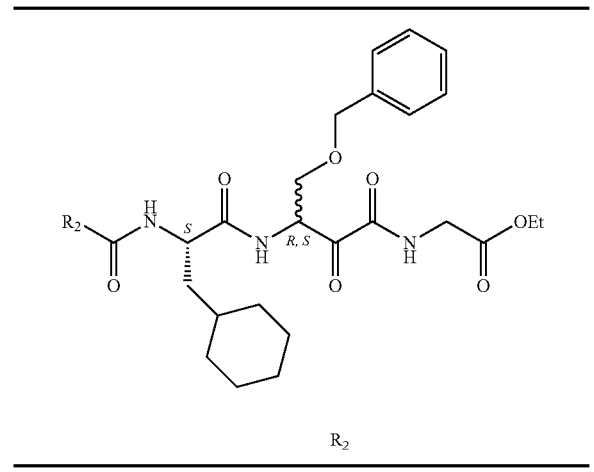
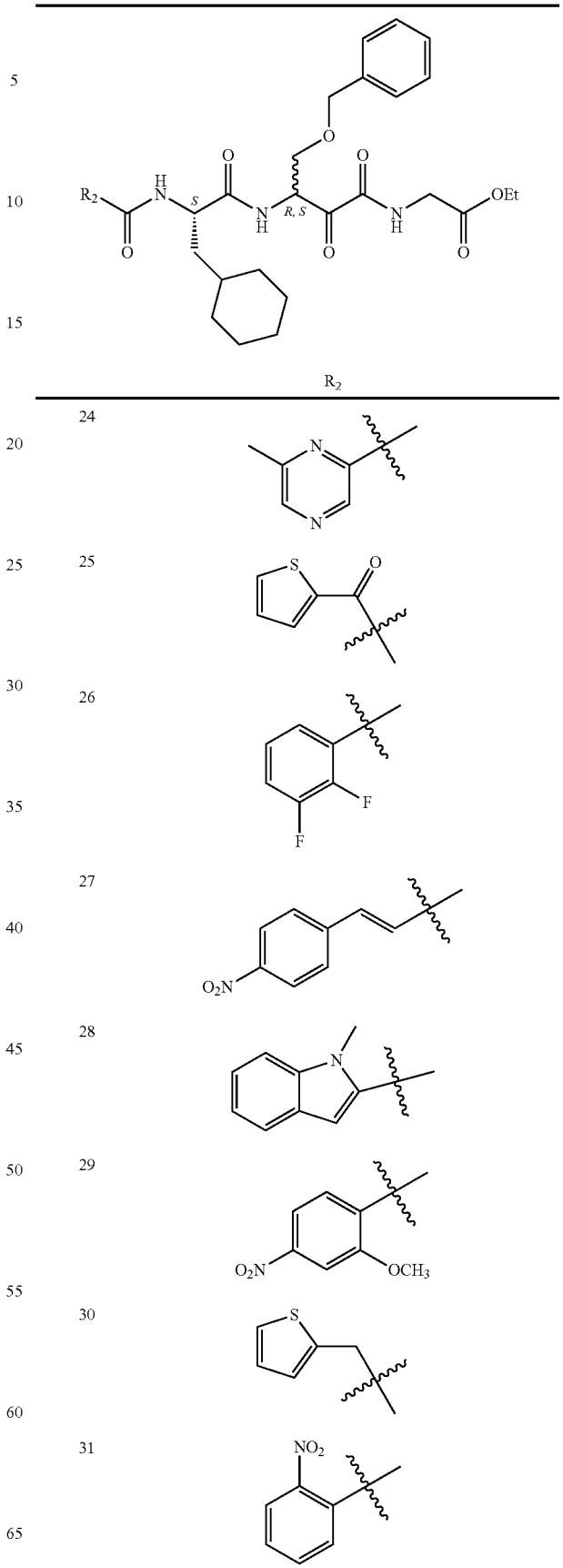

TABLE 1-continued
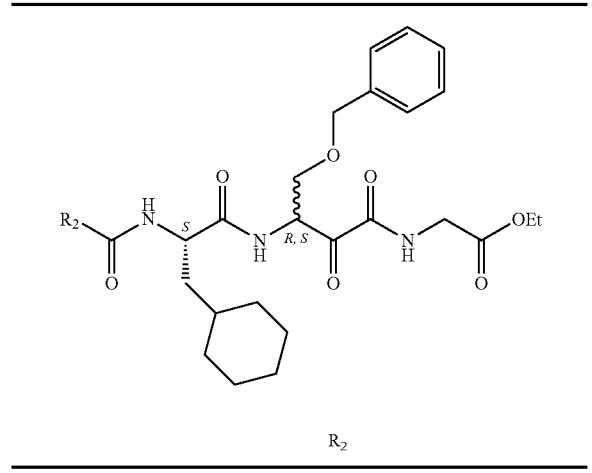
| | R₂ | |
|---|---|---|
| 32 | 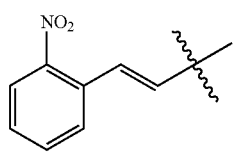 [SMILES: */C=C/c1ccccc1[N+](=O)[O-]] | |
| 33 | 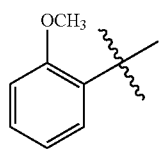 [SMILES: *c1ccccc1OC] | |
| 34 | 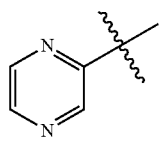 [SMILES: *c1cnccn1] | |
| 35 | 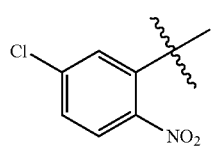 [SMILES: *c1cc(Cl)ccc1[N+](=O)[O-]] | |
| 36 | 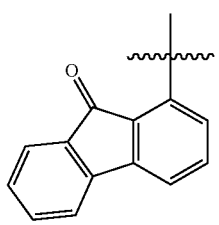 [SMILES: *c1cccc2c1C(=O)c1ccccc1-2] | |
| 37 | 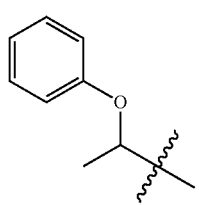 [SMILES: *C(C)Oc1ccccc1] | |
TABLE 1-continued
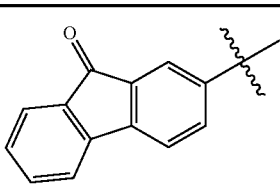
| | R₂ | |
|---|---|---|
| 38 | 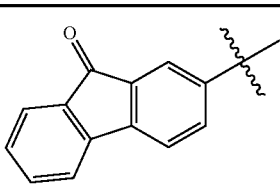 | |
| 39 |  | |
| 40 | 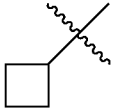 | |
| 41 | 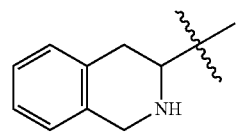 [SMILES: *C1Cc2ccccc2CN1] | |
| 42 | 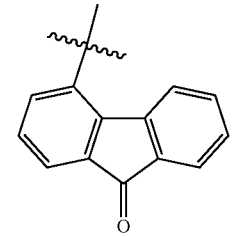 [SMILES: *c1cccc2c1-c1ccccc1C2=O] | |
| 43 | 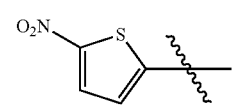 [SMILES: *c1ccc([N+](=O)[O-])s1] | |
| 44 | 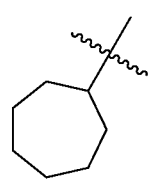 [SMILES: *C1CCCCCC1] | |

TABLE 1-continued
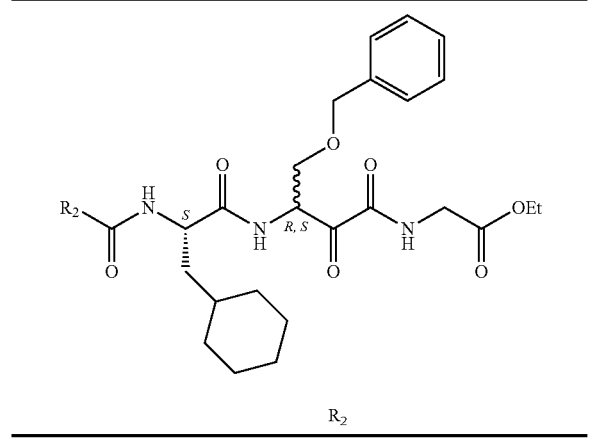
| | R₂ |
|---|---|
| 45 | 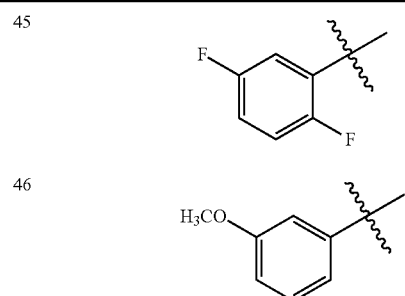 |
| 46 | 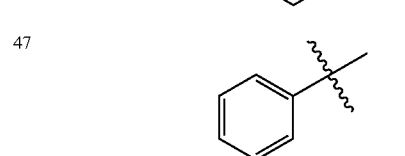 |
| 47 | 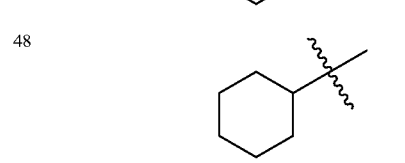 |
| 48 | 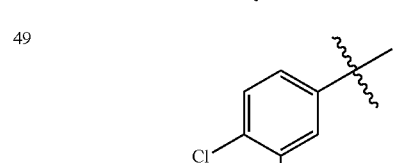 |
| 49 | 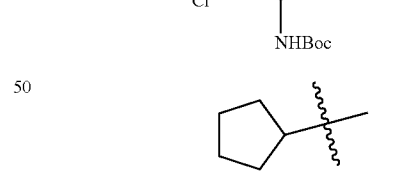 |
| 50 | 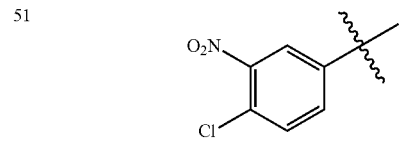 |
| 51 | 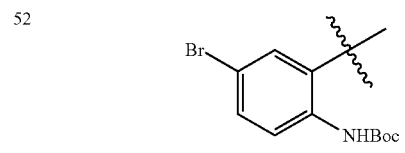 |
| 52 | |
TABLE 1-continued
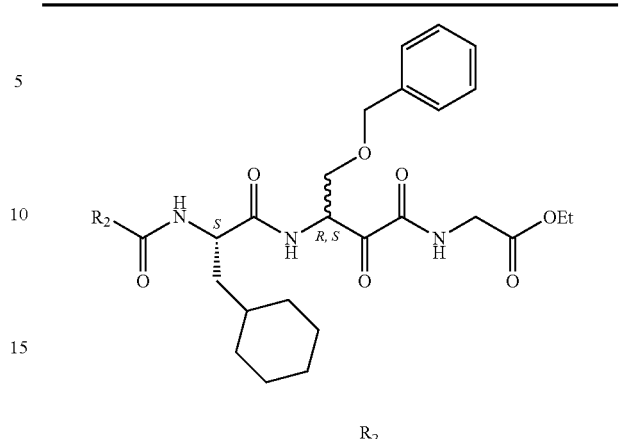
| | R₂ |
|---|---|
| 53 | 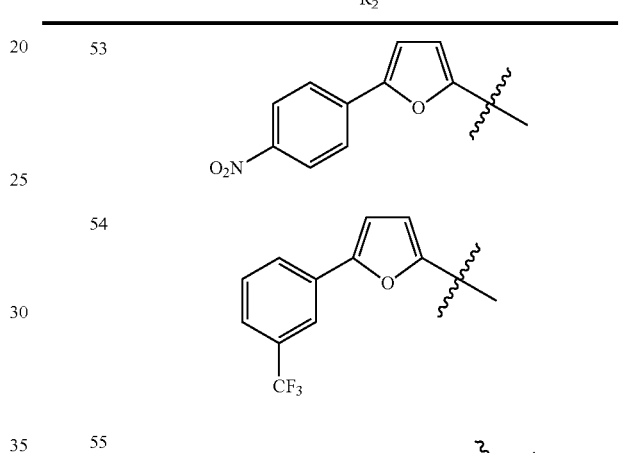 |
| 54 | |
| 55 | 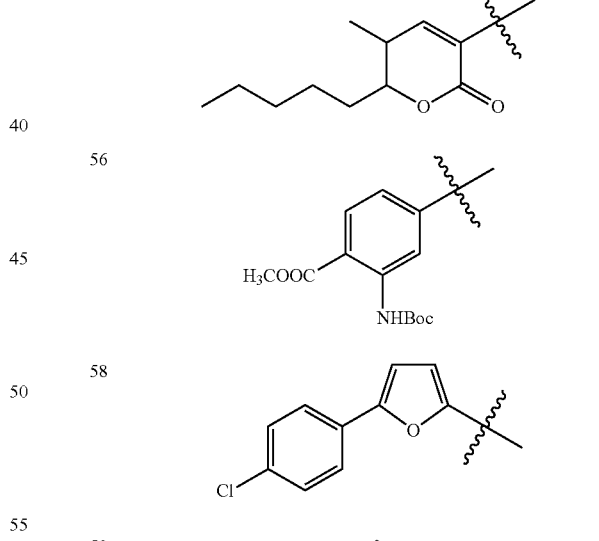 |
| 56 | |
| 58 | |
| 59 | 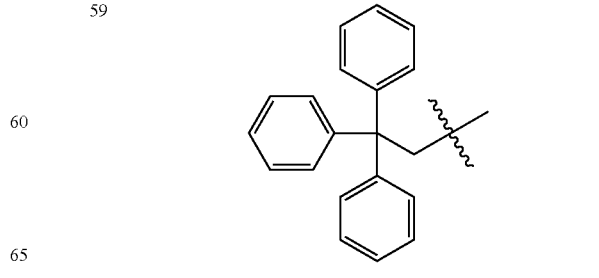 |

TABLE 1-continued
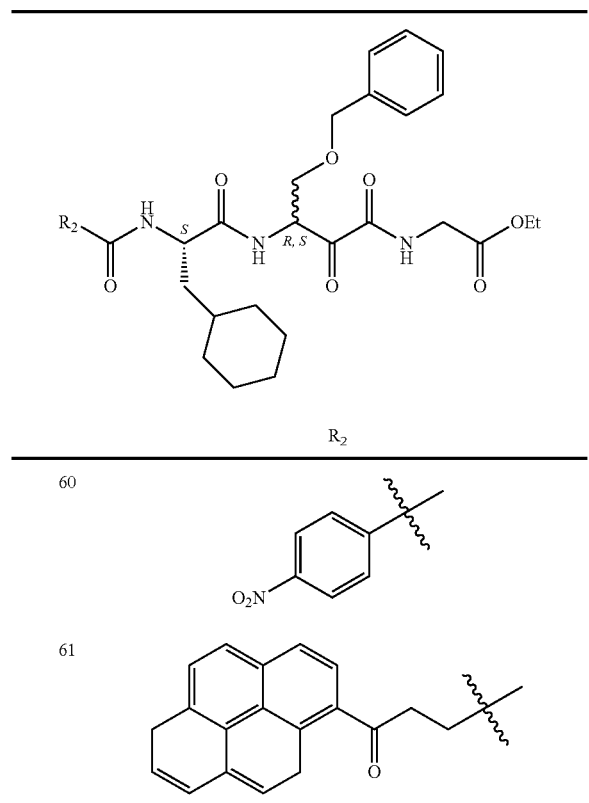
TABLE 2
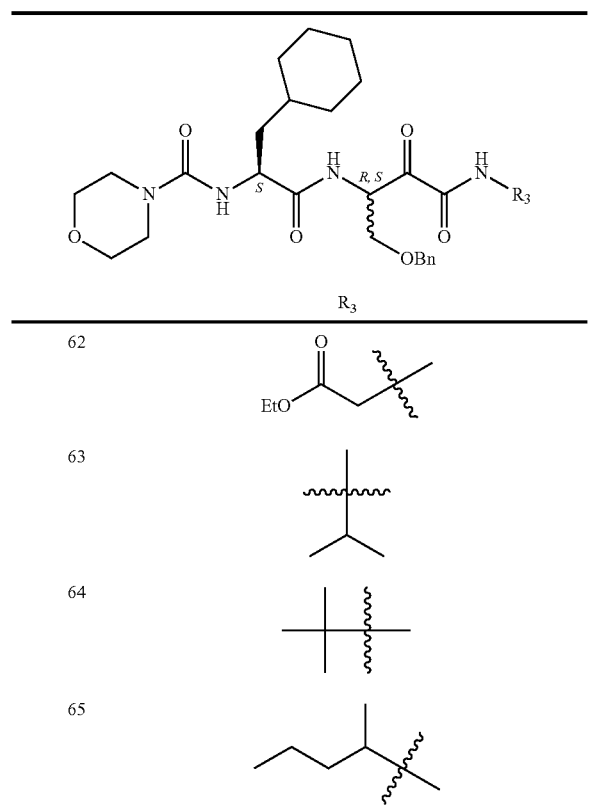
TABLE 2-continued
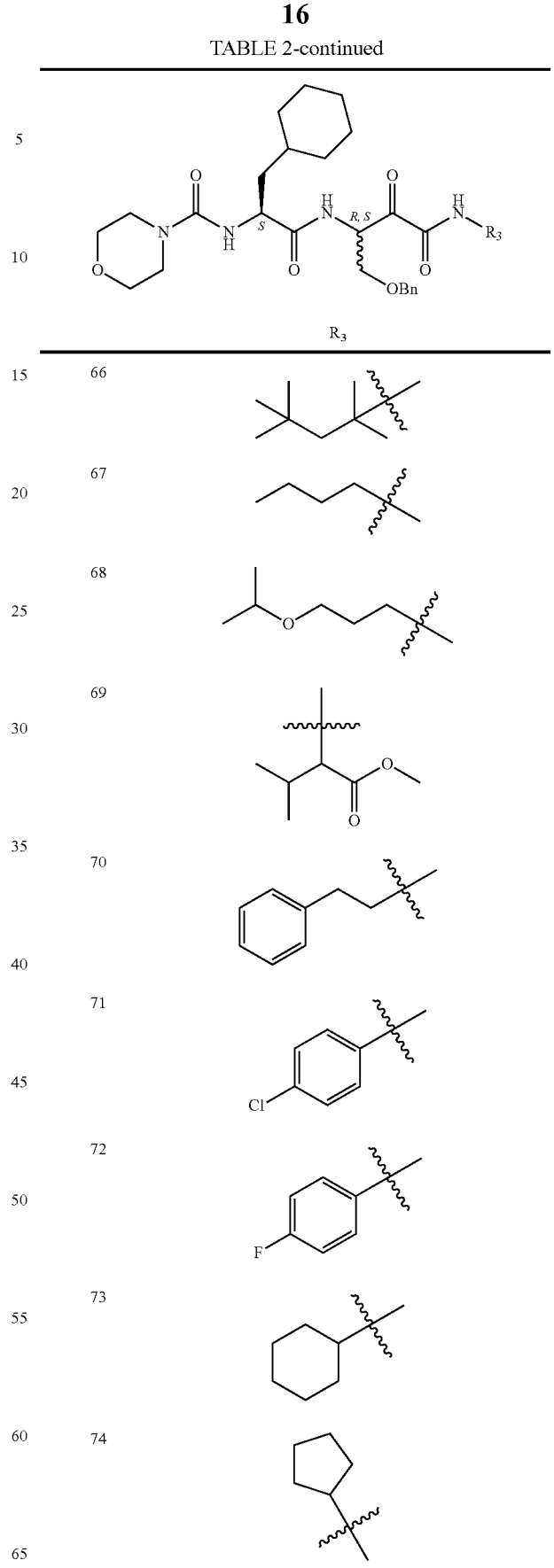

TABLE 2-continued
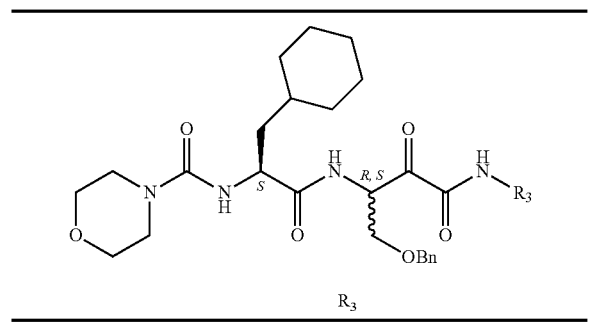
| | $R_3$ |
|---|---|
| 75 | 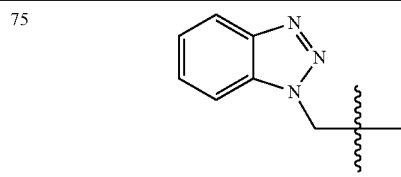 |
| 76 | 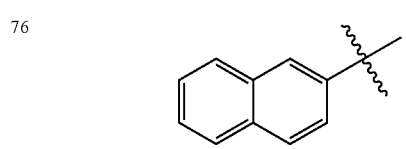 |
| 77 | 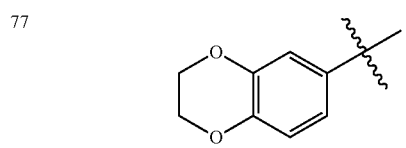 |
TABLE 2-continued
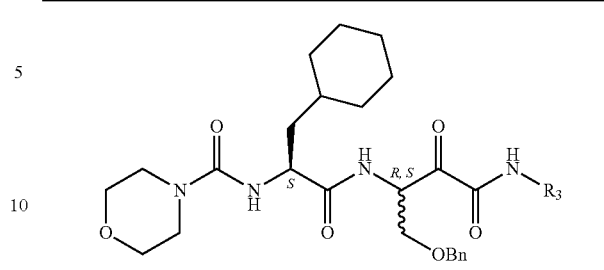
| | $R_3$ |
|---|---|
| 78 | 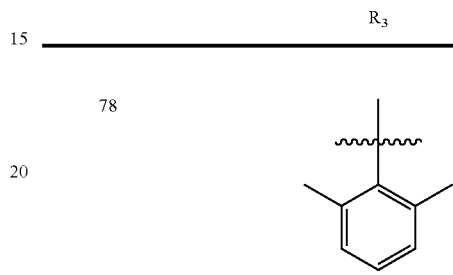 |
| 79 | 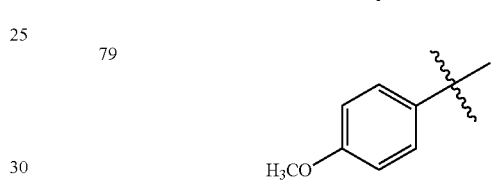 |
TABLE 3
| No. | Structure |
|---|---|
| 80 | 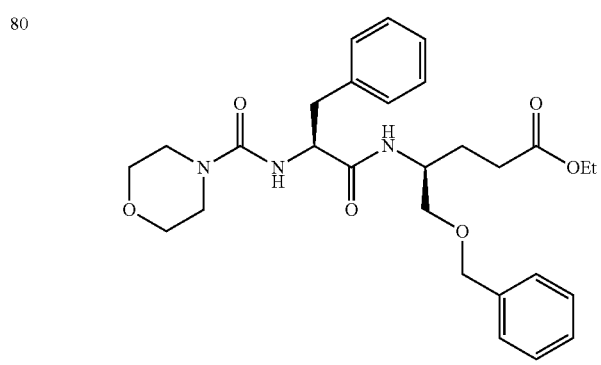 |
| 81 | 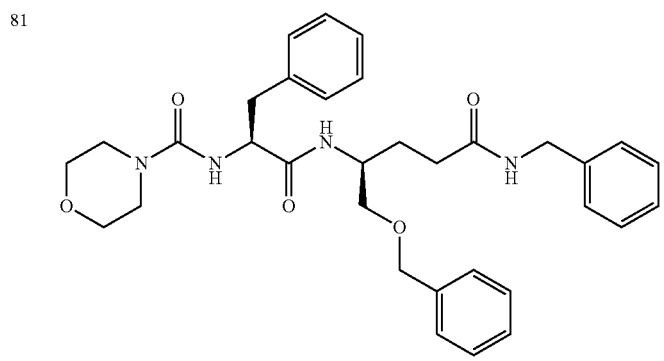 |

TABLE 3-continued

| No. | Structure |
| --- | --- |
| 82 | *(structure)* |
| 83 | *(structure)* |
| 84 | *(structure)* |
| 85 | *(structure)* |

TABLE 3-continued

| No. | Structure |
|-----|-----------|
| 86  | 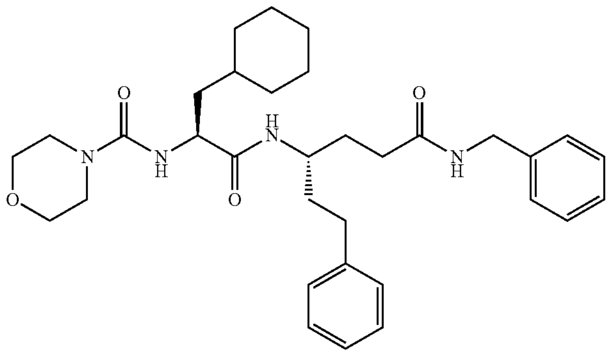 [SMILES: O=C(CC[C@H](CCc1ccccc1)NC(=O)[C@H](CC1CCCCC1)NC(=O)N1CCOCC1)NCc1ccccc1]          |
| 87  | 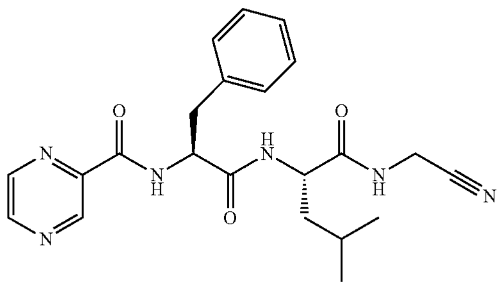 [SMILES: CC(C)C[C@H](NC(=O)[C@H](Cc1ccccc1)NC(=O)c1cnccn1)C(=O)NCC#N]          |
| 88  | 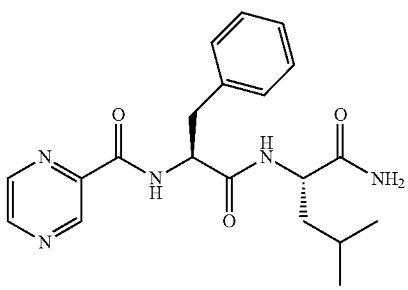 [SMILES: CC(C)C[C@H](NC(=O)[C@H](Cc1ccccc1)NC(=O)c1cnccn1)C(N)=O]          |
| 89  | 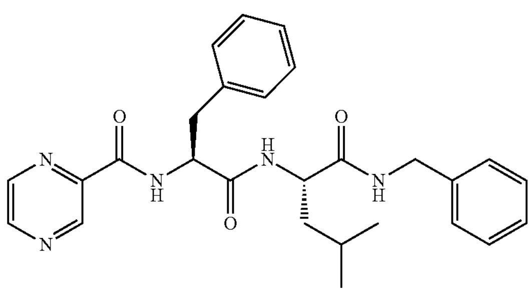 [SMILES: CC(C)C[C@H](NC(=O)[C@H](Cc1ccccc1)NC(=O)c1cnccn1)C(=O)NCc1ccccc1]          |
| 90  | 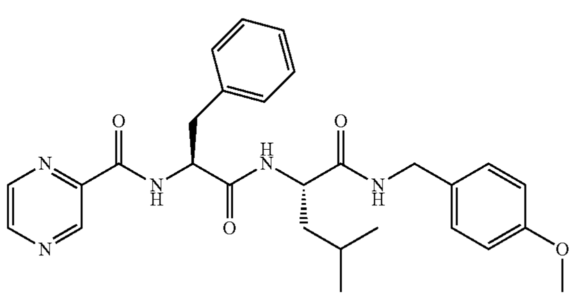 [SMILES: COc1ccc(CNC(=O)[C@H](CC(C)C)NC(=O)[C@H](Cc2ccccc2)NC(=O)c2cnccn2)cc1]          |

TABLE 3-continued

| No. | Structure |
|---|---|
| 91 | Pyrazine-2-carbonyl-Phe-Leu-NH-CH2-(4-fluorophenyl) |
| 92 | Pyrazine-2-carbonyl-Phe-Leu-NH-CH2-(4-trifluoromethylphenyl) |
| 93 | Boc-Leu-NH-CH2-CN |
| 94 | PhNH-C(O)-NH-Leu-NH-CH2-CN |
| 95 | PhNH-C(S)-NH-Leu-NH-CH2-CN |
| 96 | (4-MeO-C6H4)NH-C(S)-NH-Leu-NH-CH2-CN |

TABLE 3-continued

| No. | Structure |
|---|---|
| 97 | 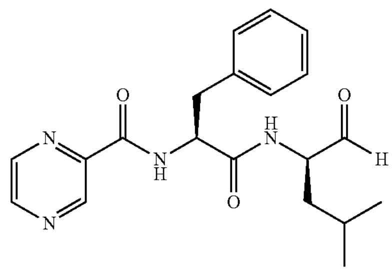 [SMILES: CC(C)C[C@H](C=O)NC(=O)[C@H](Cc1ccccc1)NC(=O)c1cnccn1] |
| 98 | 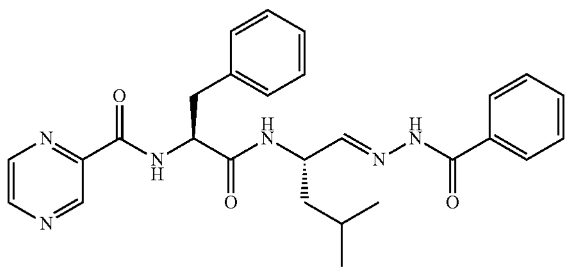 [SMILES: CC(C)C[C@@H](/C=N/NC(=O)c1ccccc1)NC(=O)[C@H](Cc1ccccc1)NC(=O)c1cnccn1] |
| 99 | 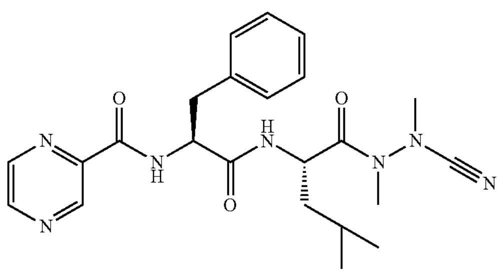 [SMILES: CC(C)C[C@H](NC(=O)[C@H](Cc1ccccc1)NC(=O)c1cnccn1)C(=O)N(C)N(C)C#N] |
| 100 | 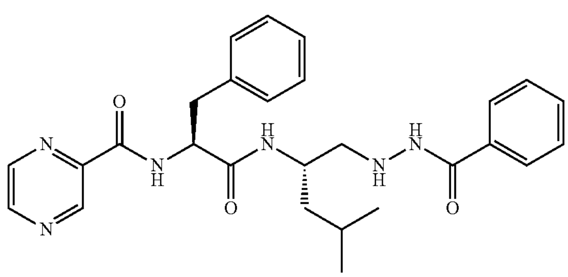 [SMILES: CC(C)C[C@@H](CNNC(=O)c1ccccc1)NC(=O)[C@H](Cc1ccccc1)NC(=O)c1cnccn1] |
| 101 | 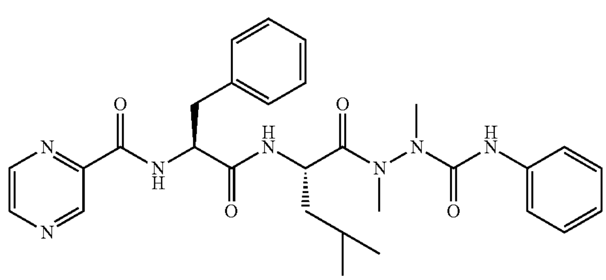 [SMILES: CC(C)C[C@H](NC(=O)[C@H](Cc1ccccc1)NC(=O)c1cnccn1)C(=O)N(C)N(C)C(=O)Nc1ccccc1] |

TABLE 3-continued
| No. | Structure |
|---|---|
| 102 | 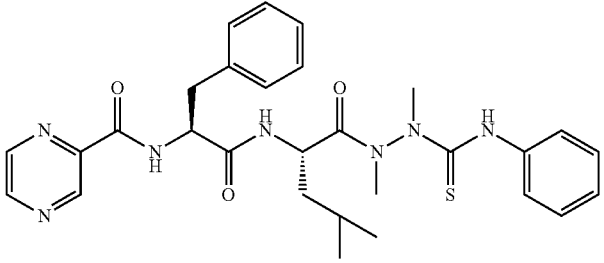 [SMILES: CC(C)C[C@H](NC(=O)[C@H](Cc1ccccc1)NC(=O)c1cnccn1)C(=O)N(C)N(C)C(=S)Nc1ccccc1] |
| 103 | 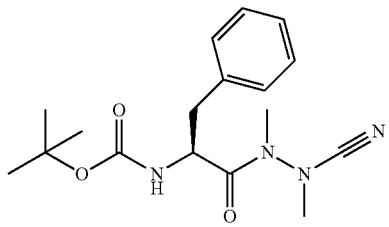 [SMILES: CN(C#N)N(C)C(=O)[C@H](Cc1ccccc1)NC(=O)OC(C)(C)C] |
| 104 | 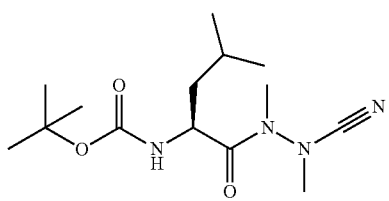 [SMILES: CC(C)C[C@H](NC(=O)OC(C)(C)C)C(=O)N(C)N(C)C#N] |
| 105 | 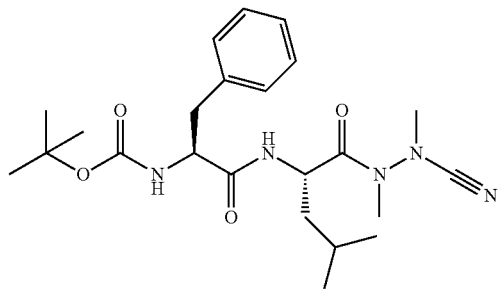 [SMILES: CC(C)C[C@H](NC(=O)[C@H](Cc1ccccc1)NC(=O)OC(C)(C)C)C(=O)N(C)N(C)C#N] |
| 106 | 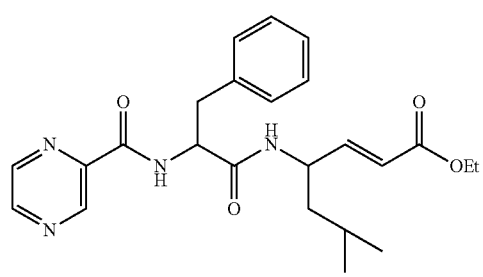 [SMILES: CCOC(=O)/C=C/C(CC(C)C)NC(=O)C(Cc1ccccc1)NC(=O)c1cnccn1] |
| 107 | 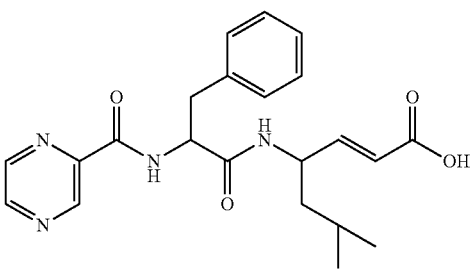 [SMILES: CC(C)CC(/C=C/C(=O)O)NC(=O)C(Cc1ccccc1)NC(=O)c1cnccn1] |

TABLE 3-continued

| No. | Structure |
|---|---|
| 108 | 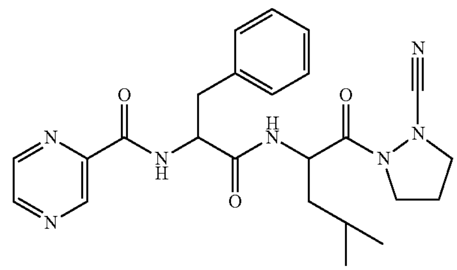 [SMILES: CC(C)CC(NC(=O)C(Cc1ccccc1)NC(=O)c1cnccn1)C(=O)N1CCCN1C#N] |
| 109 | 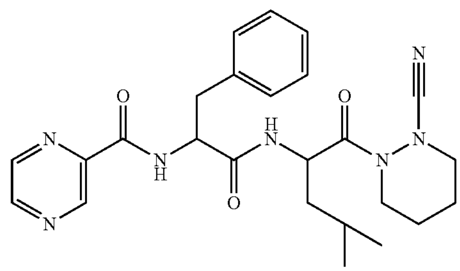 [SMILES: CC(C)CC(NC(=O)C(Cc1ccccc1)NC(=O)c1cnccn1)C(=O)N1CCCCN1C#N] |
| 110 | 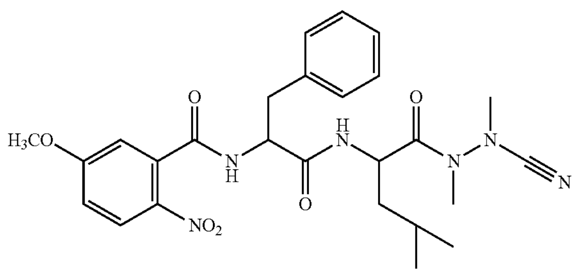 [SMILES: COc1ccc([N+](=O)[O-])c(C(=O)NC(Cc2ccccc2)C(=O)NC(CC(C)C)C(=O)N(C)N(C)C#N)c1] |
| 111 | 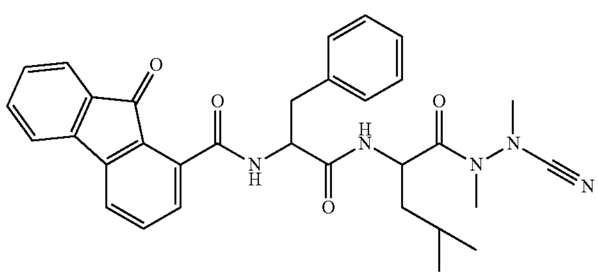 [SMILES: CC(C)CC(NC(=O)C(Cc1ccccc1)NC(=O)c1cccc2c1C(=O)c1ccccc1-2)C(=O)N(C)N(C)C#N] |
| 112 | 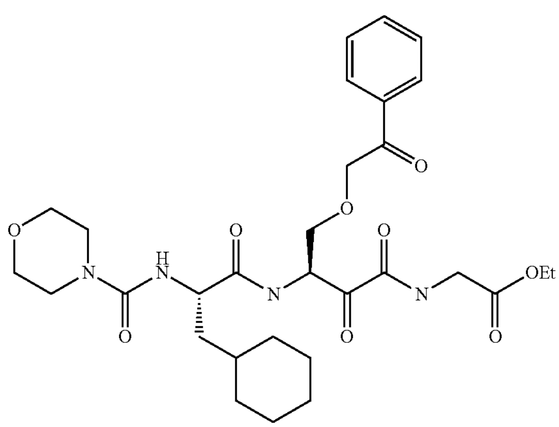 [SMILES: CCOC(=O)CNC(=O)C(=O)[C@H](COCC(=O)c1ccccc1)NC(=O)[C@H](CC1CCCCC1)NC(=O)N1CCOCC1] |

TABLE 3-continued
| No. | Structure |
|---|---|
| 113 | 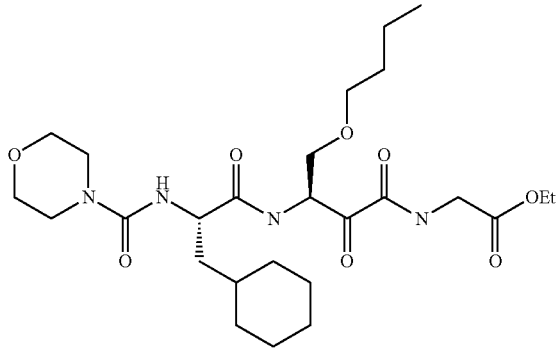 [SMILES: CCCCOC[C@H](NC(=O)[C@H](CC1CCCCC1)NC(=O)N1CCOCC1)C(=O)C(=O)NCC(=O)OCC] |
| 114 | 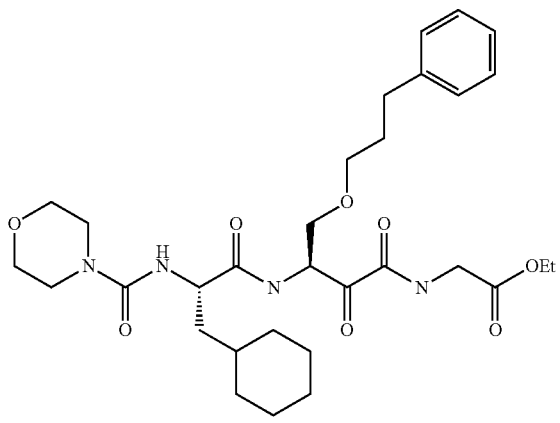 [SMILES: CCOC(=O)CNC(=O)C(=O)[C@H](COCCCc1ccccc1)NC(=O)[C@H](CC1CCCCC1)NC(=O)N1CCOCC1] |
| 115 | 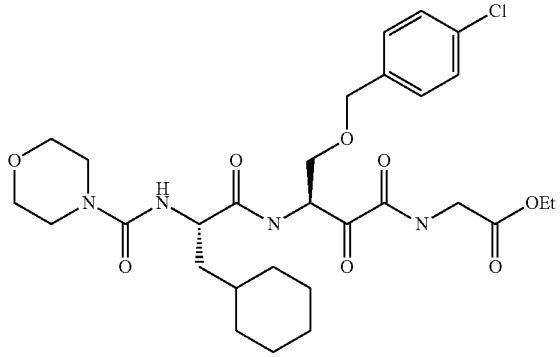 [SMILES: CCOC(=O)CNC(=O)C(=O)[C@H](COCc1ccc(Cl)cc1)NC(=O)[C@H](CC1CCCCC1)NC(=O)N1CCOCC1] |
| 116 | 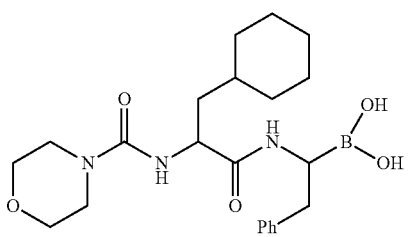 [SMILES: O=C(NC(Cc1ccccc1)B(O)O)C(CC1CCCCC1)NC(=O)N1CCOCC1] |

TABLE 4
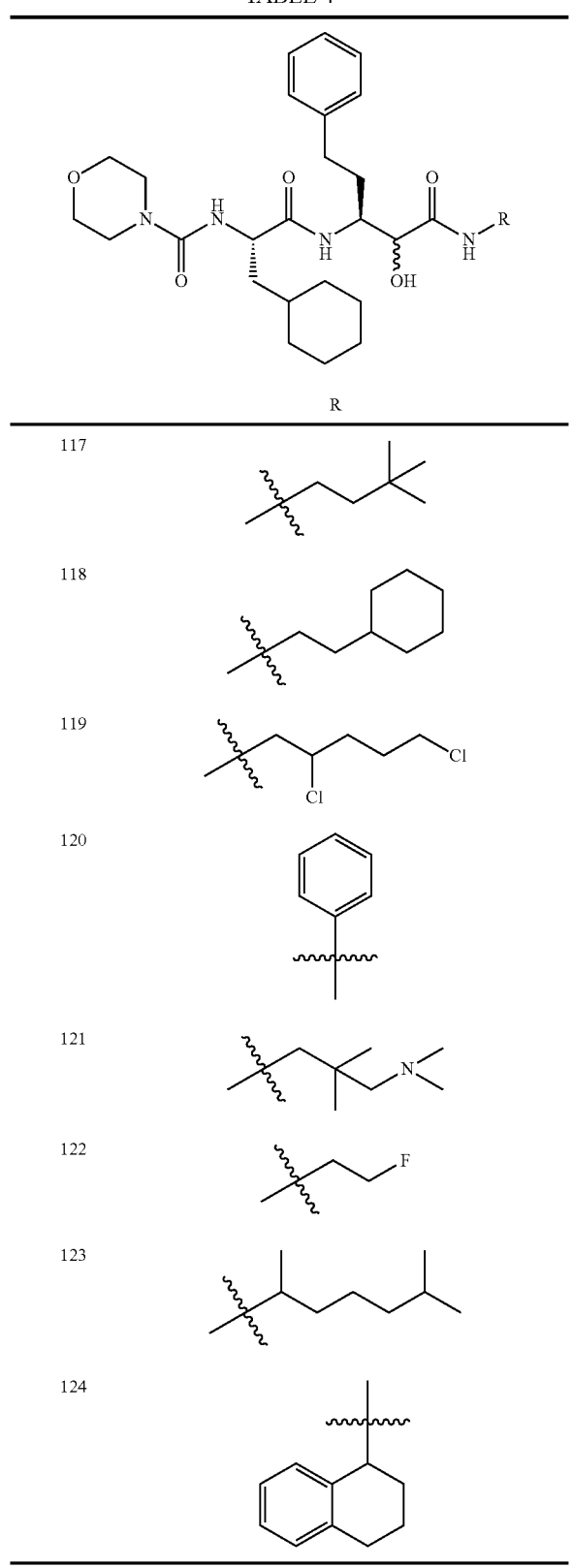
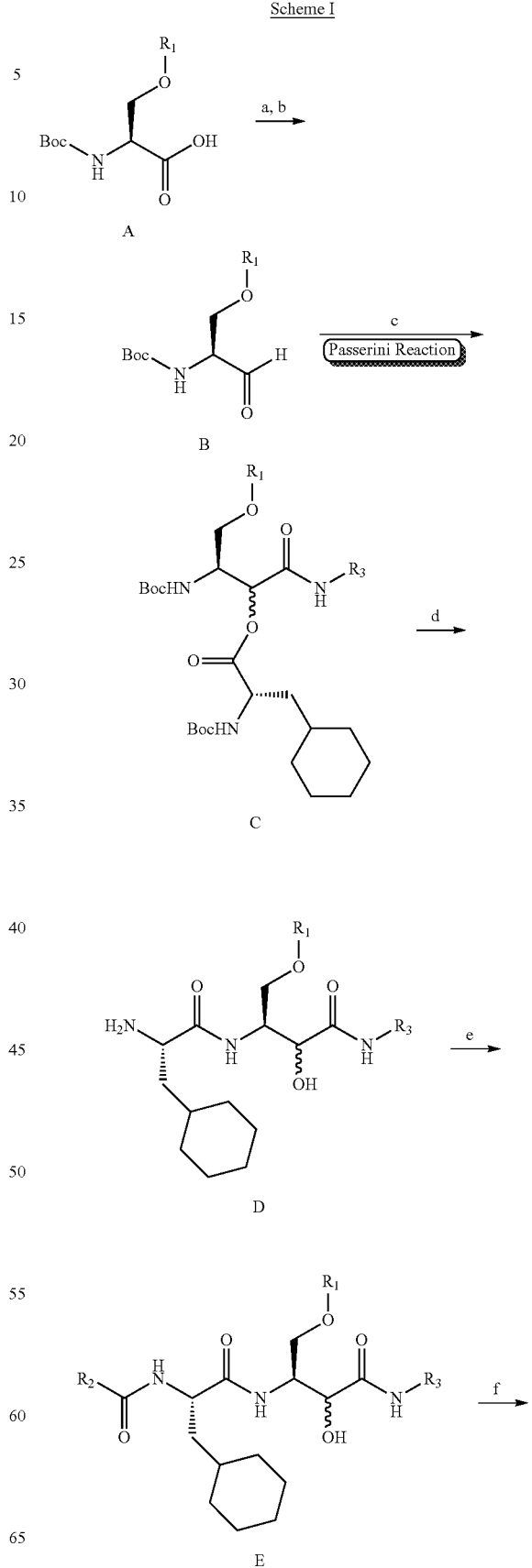
The amide compounds of this invention can be prepared by methods well known in the art. Scheme I shown below illustrates a synthetic route for synthesizing certain compounds of formula (I).

-continued

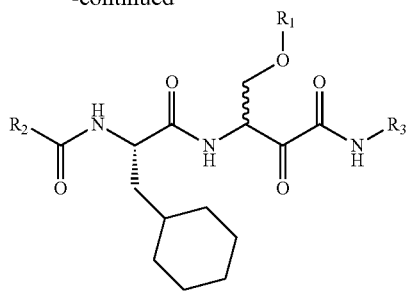

F (a) N-methylmorpholine, isobutyl chloroformate, DME, -20° C.; then NaBH₄, H₂O, 0° C.; (b) Dess-Martin periodinane, CH₂Cl₂, rt; (c) Boc-CHa-OH, R₃NC, CH₂Cl₂, rt; (d) TFA, CH₂Cl₂, rt; then Et₃N, CH₂Cl₂, rt; (e) R₂COOH, HBTU, Et₃N, DMF; (f) Dess-Martin periodinane, Hydroxy-protected Boc-L-Serine (Boc-Ser-OH) A, which is prepared from commercially available Boc-Ser-OH, is first reduced and then partially oxidized to form aldehyde B. The resulting aldehyde is reacted with N-Boc-protected cyclohexyl alanine and isocyanoacetate to undergo the Passerini reaction to form compound C, which is deprotected and followed by O- to N-acyl group migration to form α-hydroxy amide D. The amide is then coupled with an acid to form compound E, which is subject to Dess-Martin oxidation to α-ketone amide compound F, a compound of formula (I).

Compounds of formulas (II) and (III) can be synthesized by following the synthetic route shown in the scheme below:

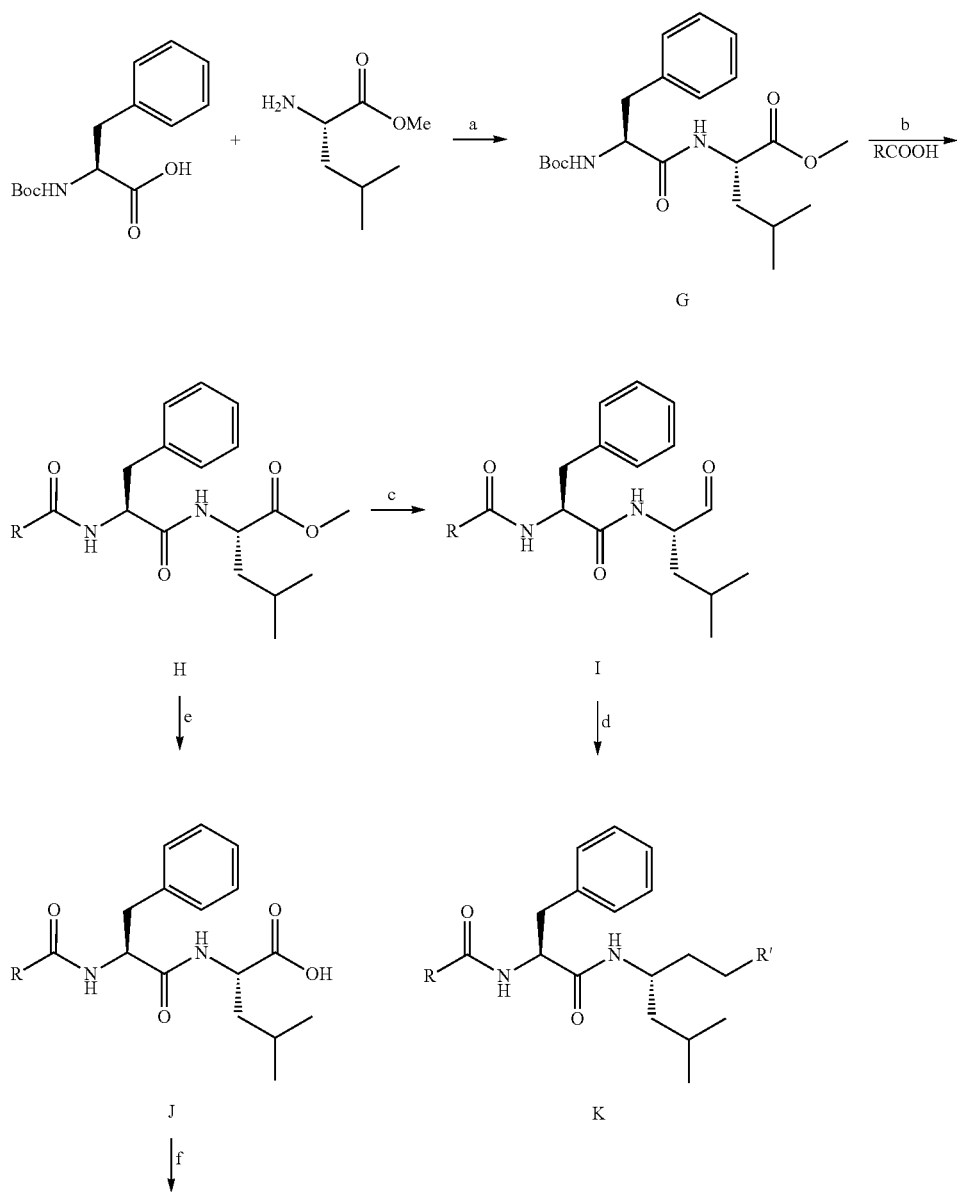

-continued

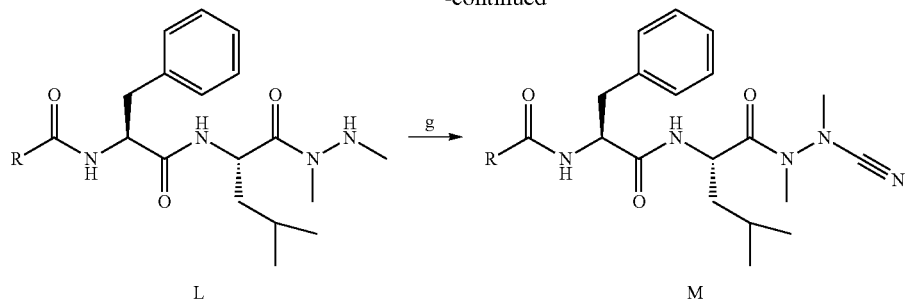

(a) HBTU, HOBt, DIPEA, DMF, 83%; (b) TFA, CH$_2$Cl$_2$; then RCOOH, IBCF, NMM, THF, 90% 2 steps; (c) NaBH$_4$, H2O, 0° C.; then Dess-Martin, CH$_2$Cl$_2$, rt; (d) Wittig reaction and then hydrogenation (e) 1M LiOH, THF, H$_2$O, 97%; (f) IBCF, NMM, THF; then N,N'-dimethylhydrazine hydrochloride salt, 3N NaOH, 89% steps; (g) BrCN, NaOAc, MeOH, r.t, 65%

As shown above, coupling two amino acids affords dipeptide G, which is reacted with an acid to give N-acyl dipeptide H. Dipeptide H is reduced to aldehyde I, which is subject to the Wittig reaction and hydrogenation to afford Compound J, a compound of formula (II). To synthesize a compound of formula (III), dipeptide H is hydrolyzed to afford an acid J, which is reacted with a hydrazine compound to give hydrozide compound L. Reacting compound L with BrCN affords desired amide compound M.

Amide compounds synthesized by the above methods can be purified by a suitable method such as column chromatography, high-pressure liquid chromatography, or recrystallization.

One skilled in the art can modify the above synthetic transformations to synthesize other amide compounds. These transformation methods may also additionally include steps, either before or after the steps described specifically herein, to add or remove suitable protecting groups in order to ultimately allow synthesis of the amide compounds. In addition, various synthetic steps may be performed in an alternate sequence or order to give the desired compounds. Synthetic transformations and protecting group methodologies (protection and deprotection) useful in synthesizing applicable amide compounds are known in the art and include, for example, those described in R. Larock, *Comprehensive Organic Transformations*, VCH Publishers (1989); T. W. Greene and P. G. M. Wuts, *Protective Groups in Organic Synthesis*, 2$^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The amide compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

The amide compounds mentioned herein include the compounds themselves, as well as their salts, prodrugs, and solvates, if applicable. A salt, for example, can be formed between an anion and a positively charged group (e.g., amino) on amide compound. Suitable anions include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate. Likewise, a salt can also be formed between a cation and a negatively charged group (e.g., carboxylate) on an amide compound. Suitable cations include sodium ion, potassium ion, magnesium ion, calcium ion, and an ammonium cation such as tetramethylammonium ion. The amide compounds also include those salts containing quaternary nitrogen atoms. Examples of prodrugs include esters and other pharmaceutically acceptable derivatives, which, upon administration to a subject, are capable of providing active amide compounds. A solvate refers to a complex formed between an active amide compound and a pharmaceutically acceptable solvent. Examples of pharmaceutically acceptable solvents include water, ethanol, isopropanol, ethyl acetate, acetic acid, and ethanolamine.

Also within the scope of this invention is a method of administering an effective amount of one or more of the amide compounds to a patient having a disease described in the summary section above. The term "treating" or "treatment" refers to administering one or more of the amide compounds to a subject, who has a disease, a symptom of such a disease, or a predisposition toward such a disease, with the purpose to confer a therapeutic effect, e.g., to cure, relieve, alter, affect, ameliorate, or prevent the disease, the symptom of it, or the predisposition toward it. "An effective amount" refers to the amount of an active amide compound that is required to confer a therapeutic effect on the treated subject. Effective doses will vary, as recognized by those skilled in the art, depending on the types of diseases treated, route of administration, excipient usage, and the possibility of co-usage with other therapeutic treatment.

To practice the method of this invention, a composition having one or more amide compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more active amide compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active amide compound. Examples of other carriers include colloidal silicon oxide, magnesium stearate, cellulose, sodium lauryl sulfate, and D&C Yellow # 10.

The amide compounds described above can be preliminarily screened for their efficacy in inhibiting cancer cells by an in vitro assay and then confirmed by animal experiments and clinic trials. Other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Chemical Synthesis

Compound 1 was synthesized as shown below:

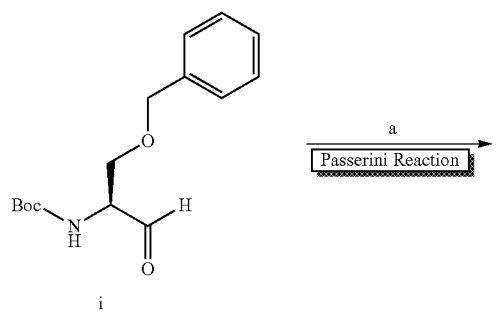

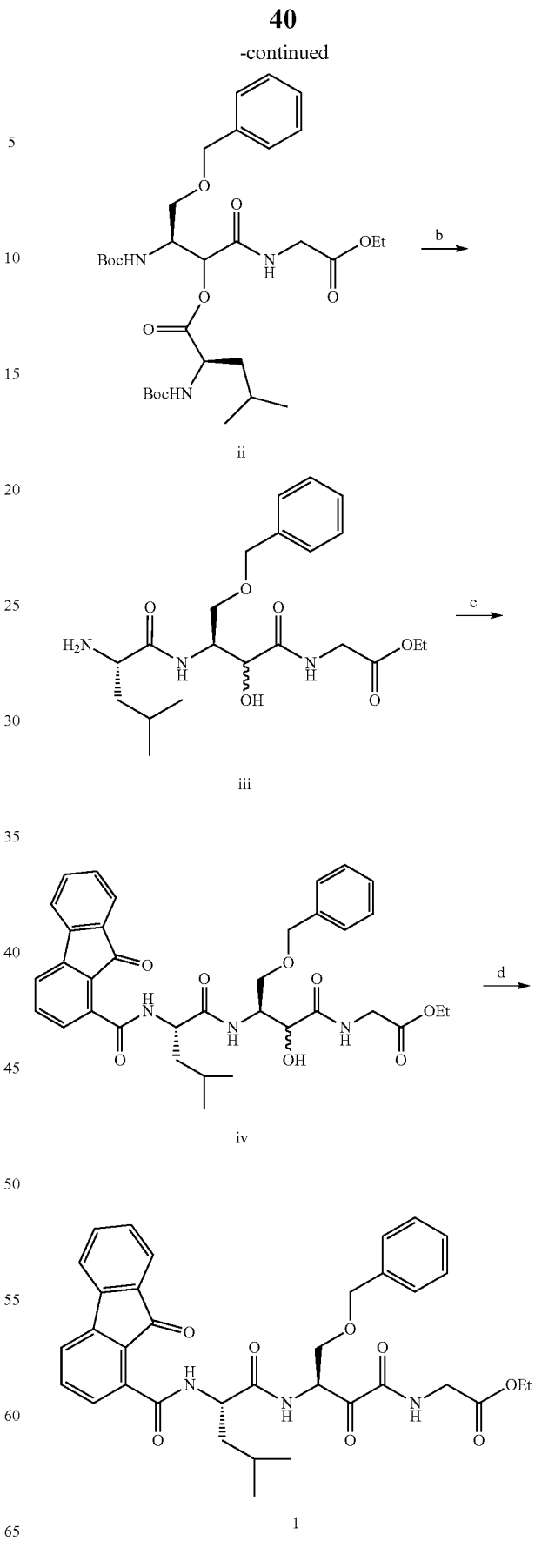

(S)-tert-butyl 1-(benzyloxy)-3-oxopropan-2-ylcarbamate (i)

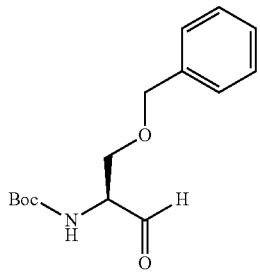 [SMILES: CC(C)(C)OC(=O)N[C@H](C=O)COCc1ccccc1]

Boc-Ser-OH (5 g, 24.4 mmole) was dissolved in dry DMF (150 mL). 60% NaH (2.1 g, 53.7 mmole) was added slowly at 0° C. under nitrogen. Benzyl Bromide (3.2 mL, 26.8 mmole) was added dropwise until no hydrogen was produced. The resulting solution was stirred at 25° C. overnight and then DMF was removed under reduced pressure. The residue was dissolved in EtOAc, washed with 1 N HCl, H$_2$O, and brine, dried over Na$_2$SO$_4$, and concentrated in vacuo. The crude product was dried under vacuum. It was used without further purification.

(2S)-3-(benzyloxy)-2-[(tert-butoxycarbonyl)amino]propanoic acid (7.2 g, 24.4 mmole) was dissolved in ethylene glycol dimethyl ether (50 mL). N-Methylmorpholine (2.7 ml, 24.4 mmole) was added, and the resulting clear solution was cooled to −20° C. Isobutyl chloroformate (3.19 ml, 24.4 mmole) was added dropwise to cause N-methylmorpholine HCl salt precipitation. Stirring was continued for 15 min and the supernatant was then transferred via a filter-tipped funnel into a rapidly stirred solution of NaBH$_4$ (2.93 g, 73.2 mmole) in ice water and washed with dry DME. After the mixture was stirred for 30 min, it was extracted with EtOAc and washed with H$_2$O. The organic layers were combined, dried over Na$_2$SO$_4$, and concentrated in vacuo. Purification by chromatography (silica, 4/1: Hexane/EtOAc, R$_f$=0.2) afforded tert-butyl N-[(1R)-2-(benzyloxy)-1-(hydroxymethyl)ethyl]carbamate as a white solid (6.3 g, 92%).

tert-Butyl N-[(1R)-2-(benzyloxy)-1-(hydroxymethyl)ethyl]carbamate (1.2 g, 4.3 mmole) was dissolved in CH$_2$Cl$_2$ (40 mL). Dess-Martin periodinane (2.4 g, 5.5 mmole) was added. The solution was stirred for 2 h at room temperature and then quenched with Na$_2$S$_2$O$_3$ and saturated bicarbonate solution. After extracting with CH$_2$Cl$_2$, the organic layer was dried over MgSO$_4$, filtered, and concentrated by rotary evaporation. Purification by chromatography (silica, 4/1: Hexane/EtOAc, R$_f$=0.4) afforded (S)-tert-butyl 1-(benzyloxy)-3-oxopropan-2-ylcarbamate as a white solid (1.1 g, 96%).

3-(Benzyloxy)-2-[(tert-butoxycarbonyl)amino]-1-[(2-ethoxy-2-oxoethyl)amino]carbonylpropyl(2R)-2-[(tert-butoxycarbonyl)amino]-4-methylpentanoate (ii) and ethyl 2-[(3S)-3-[(2S)-2-amino-4-methylpentanoyl]amino-4-(benzyloxy)-2-hydroxybutanoyl]aminoacetate (iii)

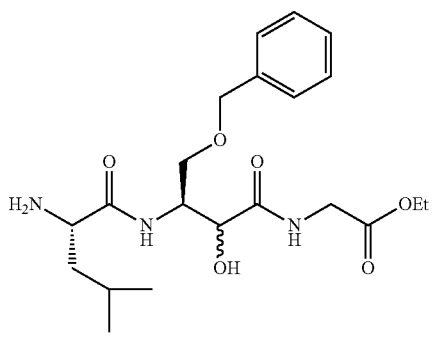 [SMILES: CCOC(=O)CNC(=O)C(O)[C@H](COCc1ccccc1)NC(=O)[C@@H](N)CC(C)C]

(S)-tert-Butyl 1-(benzyloxy)-3-oxopropan-2-ylcarbamate (630 mg, 2.3 mmole), Boc-Leu-OH (622 mg, 2.5 mmole), and ethyl isocyanoacetate (274 ul, 2.5 mmole) were dissolved in dry CH$_2$Cl$_2$ (20 mL). The solution was stirred for 48 h at room temperature, concentrated, and then purified by chromatography (silica, 2/1: Hexane/EtOAc, R$_f$=0.5) to give 3-(benzyloxy)-2-[(tert-butoxycarbonyl)amino]-1-[(2-ethoxy-2-oxoethyl)amino]carbonylpropyl (2R)-2-[(tert-butoxycarbonyl)amino]-4-methylpentanoate as a white solid (1.1 g, 75%).

3-(Benzyloxy)-2-[(tert-butoxycarbonyl)amino]-1-[(2-ethoxy-2-oxoethyl)amino]carbonylpropyl (2R)-2-[(tert-butoxycarbonyl)amino]-4-methylpentanoate was dissolved in 50% TFA in CH$_2$Cl$_2$. The solution was stirred for 30 min and then concentrated. The residue was redissolved in CH$_2$Cl$_2$ and neutralized with triethylamine. Stirring was continued for 10 min and then concentrated. Purification by chromatography (silica, 1/1: Hexane/EtOAc with 10% MeOH, R$_f$=0.2) afforded ethyl 2-[(3S)-3-[(2S)-2-amino-4-methylpentanoyl]amino-4-(benzyloxy)-2-hydroxy butanoyl]aminoacetate as a white solid.

Ethyl 2-(4-(benzyloxy)-2-hydroxy-3-[((2R)-4-methyl-2-[(9-oxo-9H-1-fluorenyl)carbonyl]aminopentanoyl)amino]butanoylamino)acetate (iv)

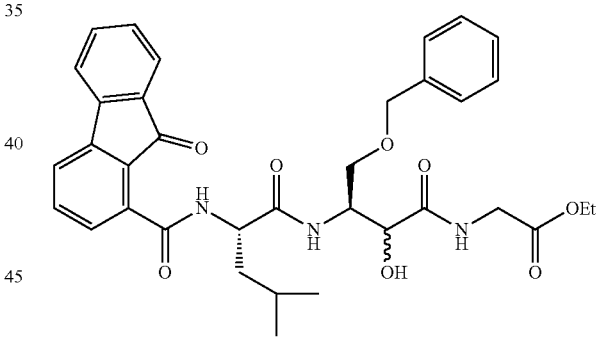

Ethyl 2-[(3S)-3-[(2S)-2-amino-4-methylpentanoyl]amino-4-(benzyloxy)-2-hydroxyl butanoyl]aminoacetate (500 mg, 1.2 mmole), 9-Fluorenone-1-Carboxylic acid (266 mg, 1.2 mmole), and HBTU (587 mg, 1.6 mmole) were dissolved in DMF (10 mL). Et$_3$N (330 ul, 2.4 mmole) was added and stirring was continued overnight. DMF was removed under reduced pressure. The residue was diluted with EtOAc and washed with water. The organic layer was dried over MgSO$_4$, filtered, and concentrated by rotary evaporation. Purification by chromatography (silica, EtOAc, R$_f$=0.3) afforded ethyl 2-(4-(benzyloxy)-2-hydroxy-3-[((2R)-4-methyl-2-[(9-oxo-9H-1-fluorenyl)carbonyl]aminopentanoyl)amino]butanoylamino)acetate as a white solid (641 mg, 85%).

Ethyl 2-(4-(benzyloxy)-3-[((2R)-4-methyl-2-[(9-oxo-9H-1-fluorenyl)carbonyl]aminopropanoyl)amino]-2-oxobutanoylamino)acetate (1)

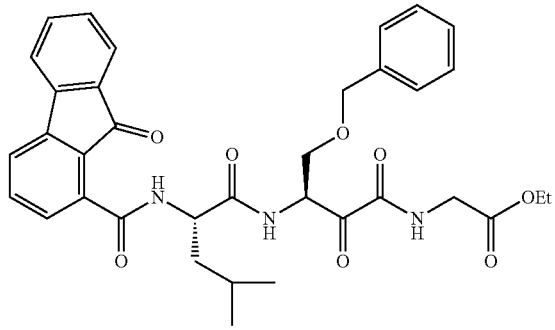 [SMILES: CCOC(=O)CNC(=O)C(=O)[C@H](COCc1ccccc1)NC(=O)[C@H](CC(C)C)NC(=O)c1cccc2c1C(=O)c1ccccc1-2]

α-Hydroxy (50 mg, 0.08 mmole) was dissolved in $CH_2Cl_2$ (1 mL). Dess-Martin periodinane (100 mg, 0.24 mmole) was added and the solution was stirred for 2 h at room temperature. The solution was quenched with $Na_2S_2O_3$ and saturated bicarbonate solution. After extracting with $CH_2Cl_2$, the organic layer was dried over $MgSO_4$, filtered, and concentrated by rotary evaporation. Purification by chromatography (silica, EtOAc, $R_f$=0.5) afforded ethyl-(4-(benzyloxy)-3-[((2R)-4-methyl-2-[(9-oxo-9H-1-fluorenyl)carbonyl]aminopropanoyl)amino]-2-oxobutanoylamino)acetate as a white solid (41 mg, 82%).

$^1$H NMR ($CDCl_3$, 400 MHz) δ 10.41 (d, J=6.8 Hz, 1H), 8.20 (d, J=7.6 Hz, 1H), 7.65-7.50 (m, 5H), 7.34-7.24 (m, 3H), 7.19-7.14 (m, 5H), 5.52-5.49 (m, 1H), 4.76-4.71 (m, 1H), 4.41 (s, 2H), 4.21 (q, J=14.0, 7.6 Hz, 2H), 4.16 (dd, J=9.6, 3.6 Hz, 1H), 4.00 (d, J=5.2 Hz, 2H), 3.80 (dd, J=10.0, 3.6 Hz, 1H), 1.90-1.80 (m, 3H), 1.26 (t, J=7.2 Hz, 3H), 1.00 (d, J=6.0 Hz, 3H), 0.95 (d, J=6.0 Hz, 3H); $^{13}$C NMR ($CDCl_3$, 100 MHz) δ195.70, 192.9, 171.97, 168.49, 164.3, 159.1, 145.7, 143.5, 137.4, 135.9, 135.2, 133.4, 132.9, 132.6, 130.3, 129.7, 128.3, 127.6, 127.5, 125.4, 123.2, 120.1, 73.3, 69.5, 61.8, 55.5, 52.9, 41.0, 40.3, 40.3, 24.9, 23.0, 22.0, 14.1; HRFABMS calcd for $C_{35}H_{37}N_3O_8Na$ 650.2478, found 650.2471.

Ethyl 2-[4-(benzyloxy)-3-((2R)-3-cyclohexyl-2-[(3-nitrobenzoyl)amino]propanoyl amino)-2-oxobutanoyl]aminoacetate (2)

The title compound, a white powder, was prepared in the same manner as was Compound 1.

$^1$H NMR ($CDCl_3$, 400 MHz, mixture of two diastereomers) δ 8.56 and 8.54 (t, J=1.9 Hz, 1H), 8.26 and 8.24 (dd, J=2.1, 0.8 Hz, 1H), 8.04 and 8.02 (t, J=1.1 and 1.2 Hz, 1H), 7.52-7.41 (m, 3H), 7.27-7.16 (m, 6H), 7.04 (d, J=7.8 Hz, 1H), 5.52-5.49 (m, 1H), 4.85-4.79 (m, 1H), 4.43 and 4.31 (s and dd, J=20.8, 12.0 Hz, 2H), 4.22 (q, J=7.2 Hz, 2H), 4.20-4.16 (m, 1H), 4.02 (dd, J=5.5, 2.5 Hz, 2H), 3.78 (dd, J=9.9, 3.3 Hz, 1H), 1.92-1.60 (m, 8H), 1.45-1.39 (m, 1H), 1.27 (t, J=7.1 Hz, 3H), 1.24-1.06 (m, 2H), 1.00-0.83 (m, 2H); $^{13}$C NMR ($CDCl_3$, 100 MHz, mixture of two diastereomers) δ 192.7, 172.3, 168.6, 164.7, 159.1, 148.1, 137.1, 135.3, 133.0, 129.6, 128.4, 127.9, 127.7, 127.6, 126.1, 122.3, 73.4, 69.2, 61.9, 55.7, 51.6, 41.0, 40.2, 34.1, 33.5, 32.8, 26.3, 26.1, 26.0, 14.1; HRFABMS calcd for $C_{31}H_{38}N_4O_9Na$ 633.2536, found 633.2518.

Ethyl 2-[4-(benzyloxy)-3-((2R)-2-[(5-chloro-2-nitrobenzoyl)amino]-3-cyclohexyl propanoylamino)-2-oxobutanoyl]aminoacetate (35)

The title compound, a white powder, was prepared in the same manner as was Compound 1.

$^1$H NMR ($CDCl_3$, 400 MHz, mixture of two diastereomers) δ 8.00 (d, J=8.7 Hz, 1H), 7.51-7.46 (m, 2H), 7.35 (m, 1H), 7.30-7.25 (m, 2H), 7.21-7.20 (m, 3H), 7.06 (d, J=7.8 Hz, 0.3H), 6.90 (d, J=7.8 Hz, 0.6H), 6.57 (d, J=8.4 Hz, 1H), 5.45-5.42 (m, 1H), 4.80-4.74 (m, 1H), 4.46 (s and dd, J=26.4, 12.0 Hz, 2H), 4.24-4.18 (m, 3H), 4.04-4.00 (m, 2H), 3.80 (dd, J=9.8, 3.2 Hz, 1H), 1.85 (d, J=13.0, 1H), 1.73-1.61 (m, 7H), 1.43 (m, 1H), 1.28 and 1.27 (t, J=7.1, 7.2 Hz, 3H), 1.20-1.13 (m, 1H), 1.04-0.90 (m, 2H); $^{13}$C NMR ($CDCl_3$, 100 MHz, mixture of two diastereomers) δ 192.7, 171.2, 168.5, 164.8, 159.1, 144.6, 140.3, 137.2, 134.0, 130.5, 129.0, 128.9, 128.4, 127.9, 127.8, 127.7, 126.0, 73.4, 69.3, 61.9, 55.7, 51.4, 41.1, 40.0, 34.0, 33.6, 33.5, 32.8, 26.4, 26.1, 26.0, 14.1; HRFABMS calcd for $C_{31}H_{38}N_4O_9Cl$ 645.2327, found 645.2323.

Ethyl 2-[4-(benzyloxy)-3-((2R)-2-[(4-chloro-3-nitrobenzoyl)amino]-3-cyclohexylpropanoylamino)-2-oxobutanoyl]aminoacetate (51)

The title compound, a white powder, was prepared in the same manner as was Compound 1.

$^1$H NMR ($CDCl_3$, 400 MHz, mixture of two diastereomers) δ 8.29 and 8.28 (d, J=2.1 and 2.0 Hz, 1H), 7.56 (d, J=8.4 Hz, 1H), 7.34 (t, J=5.4 Hz, 1H), 7.29-7.23 (m, 3H), 7.21-7.17 (m, 2H), 7.13 (d, J=8.3 Hz, 1H), 7.01 (d, J=7.6 Hz, 0.2H), 6.87 (d, J=7.8 Hz, 0.8H), 5.49-5.43 (m, 1H), 4.78-4.73 (m, 1H), 4.43 (dd, J=16.5, 11.9 Hz, 2H), 4.23 (q, J=7.1 Hz, 2H), 4.19 (dd, J=10.0, 3.6 Hz, 1H), 4.02 (dd, J=5.4, 3.7 Hz, 1H), 3.79 (dd, J=9.9, 3.4 Hz, 1H), 1.82-1.60 (m, 8H), 1.44-1.33 (m, 1H), 1.28 (t, J=7.2 Hz, 3H), 1.25-1.11 (m, 2H), 1.02-0.84 (m, 2H); $^{13}$C NMR ($CDCl_3$, 100 MHz, mixture of two diastereomers) δ 192.7, 172.4, 168.5, 163.8, 159.1, 147.7, 137.1, 133.4, 132.0, 131.4, 130.1, 128.4, 127.9, 127.7, 124.6, 73.4, 69.2, 61.9, 55.7, 51.7, 41.0, 40.1, 34.1, 33.5, 32.8, 26.3, 26.0, 25.9, 14.1.

Ethyl 2-[(3R)-4-(benzyloxy)-3-((2R)-3-cyclohexyl-2-[(5-methoxy-2-nitrobenzoyl)amino]propanoylamino)-2-oxobutanoyl]aminoacetate (8)

The title compound, a white powder, was prepared in the same manner as was Compound 1.

$^1$H NMR ($CDCl_3$, 400 MHz) δ 7.94 (d, J=8.9 Hz, 1H), 7.48 (t, J=5.5 Hz, 1H), 7.22-7.13 (m, 6H), 6.90 (d, J=8.7 Hz, 1H), 6.85-6.80 (m, 2H), 5.32-5.28 (m, 1H), 4.81-4.75 (m, 1H), 4.36 (dd, J=36.0, 12.0 Hz, 2H), 4.15 (dd, J=14.2, 7.2 Hz, 2H), 4.10 (dd, J=9.9, 3.6 Hz, 1H), 3.95 (t, J=5.7 Hz, 2H), 3.77 (s, 3H), 3.67 (dd, J=9.9, 3.2 Hz, 1H), 1.77 (d, J=12.3 Hz, 1H), 1.70-1.56 (m, 6H), 1.37 (m, 1H), 1.23-1.18 (m, 4H), 1.16-1.03 (m, 2H), 0.96-0.79 (m, 2H); $^{13}$C NMR ($CDCl_3$, 100 MHz) δ192.8, 171.5, 168.6, 166.4, 163.5, 159.3, 138.7, 137.3, 135.0, 128.3, 128.5, 127.7, 126.9, 73.3, 69.4, 61.7, 56.1, 55.6, 51.2, 41.0, 39.6, 33.9, 33.4, 32.8, 26.3, 26.1, 26.0, 14.1; HRFABMS calcd for $C_{32}H_{40}N_4O_{10}Na$ 663.2642, found 663.2637

Ethyl 2-[4-(benzyloxy)-3-((2R)-3-cyclohexyl-2-[(3-methyl-2-nitrobenzoyl)amino]propanoylamino)-2-oxobutanoyl]aminoacetate (20)

The title compound, a white powder, was prepared in the same manner as was Compound 1.

$^1$H NMR (CDCl$_3$, 400 MHz, mixture of two diastereomers) δ 7.26-7.23 (m, 4H), 7.15-7.05 (m, 5H), 6.85 (d, J=7.3 Hz, 0.4H), 6.71 (d, J=7.8 Hz, 0.6H), 6.45 (d, J=8.4 Hz, 0.6H), 6.40 (d, J=8.4 Hz, 0.4H), 5.35-5.29 (m, 1H), 4.63-4.55 (m, 1H), 4.31 and 4.31 (s and dd, J=28.8, 12.0 Hz, 2H), 4.11-4.02 (m, 3H), 4.89-3.86 (m, 2H), 3.65 (td, J=8.2, 3.3 Hz, 1H), 3.22 (s, 3H), 1.69 (d, J=11.5 Hz, 1H), 1.62-1.43 (m, 8H), 1.25-1.24 (m, 1H), 1.16-0.94 (m, 5H), 0.88-0.68 (m, 2H); $^{13}$C NMR (CDCl$_3$, 100 MHz, mixture of two diastereomers) δ193.0, 192.9, 171.7, 168.6, 165.4, 165.2, 159.4, 159.2, 149.4, 149.2, 137.3, 133.8, 131.2, 130.5, 130.4, 129.9, 129.7, 128.4, 127.8, 127.7, 125.7, 73.4, 73.3, 69.4, 69.3, 61.8, 55.8, 55.7, 51.3, 51.2, 41.1, 40.0, 39.8, 34.0, 33.7, 33.6, 32.7, 32.6, 26.4, 26.2, 26.0, 17.7, 14.1; HRFABMS calcd for C$_{32}$H$_{40}$N$_4$O$_9$Na 647.2693 found 647.2697.

Ethyl 2-[4-(benzyloxy)-3-((2R)-3-cyclohexyl-2-[(4-methoxybenzoyl)amino]propanoylamino)-2-oxobutanoyl]aminoacetate (3)

The title compound, a white powder, was prepared in the same manner as was Compound 1.

$^1$H NMR (CDCl$_3$, 400 MHz, mixture of two diastereomers) δ 7.75-7.72 (m, 2H), 7.46 and 7.43 (t, J=5.6 Hz, 1H), 7.24-7.08 (m, 5H), 7.04 and 7.03 (d, J=8.6 and 8.5 Hz, 2H), 6.91 and 6.87 (d, J=8.4 and 8.2 Hz, 1H), 5.43-5.39 (m, 1H), 4.80-4.75 (m, 1H), 4.37 and 4. (s and dd, J=19.0, 12.0 Hz, 2H), 4.15 and 4.12 (q, J=7.1 and 7.2 Hz, 2H), 4.08 (dd, J=9.6, 3.9 Hz, 1H), 3.95 and 3.90 (dd and d, J=5.7, 1.7 and 5.8 Hz, 1H), 3.72 and 3.67 (dd and d, J=9.8, 3.3 and 10.0, 3.3 Hz, 1H), 2.23 (s, 3H), 1.76-1.54 (m, 8H), 1.35-1.30 (m, 1H), 1.21 (t, J=7.2 Hz, 3H), 1.16-1.03 (m, 2H), 0.95-0.79 (m, 2H); $^{13}$C NMR (CDCl$_3$, 100 MHz, mixture of two diastereomers) δ192.9, 192.8, 172.2, 172.1, 168.9, 168.5, 166.5, 166.3, 159.3, 159.1, 153.2, 137.2, 137.1, 131.4, 128.6, 128.3, 127.8, 127.6, 127.5, 121.7, 73.3, 69.3, 61.7, 61.6, 55.7, 55.6, 51.3, 51.2, 41.0, 40.2, 39.8, 34.2, 34.1, 33.6, 33.5, 32.8, 32.7, 26.3, 26.1, 26.0, 21.0, 14.1; HRFABMS calcd for C$_{33}$H$_{41}$N$_3$O$_9$Na 646.2741 found 646.2744.

Ethyl 2-(4-(benzyloxy)-3-[((2R)-2-[2-chloro-5-(methylsulfanyl)benzoyl]amino-3-cyclohexylpropanoyl)amino]-2-oxobutanoylamino)acetate (10)

The title compound, a white powder, was prepared in the same manner as was Compound 1.

$^1$H NMR (CDCl$_3$, 400 MHz, mixture of two diastereomers) δ 7.46 and 7.44 (d, J=2.2 and 2.3 Hz, 1H), 7.40-7.36 (m, 1H), 7.28-7.22 (m, 4H), 7.21-7.17 (m, 3H), 7.02 (d, J=7.8 Hz, 1H), 6.67 and 6.66 (d, J=8.1 and 8.2 Hz, 1H), 5.49-5.47 (m, 1H), 4.82-4.74 (m, 1H), 4.43 and 4.42 (s and dd, J=18.3, 12.0 Hz, 2H), 4.20 (q, J=7.1 Hz, 2H), 4.17 (t, J=3.0 Hz, 1H), 4.01 and 3.99 (dd and d, J=5.5, 2.6 and 5.6 Hz, 2H), 3.77 (dd, J=9.8, 2.6, 1H), 2.44 and 2.43 (s, 3H), 1.85-1.57 (m, 7H), 1.43-1.41 (m, 1H), 1.27 (t, J=7.1 Hz, 3H), 1.23-1.11 (m, 3H), 1.02-0.84 (m, 2H); $^{13}$C NMR (CDCl$_3$, 100 MHz, mixture of two diastereomers) δ 192.8, 192.7, 171.4, 168.5, 166.2, 165.9, 159.0, 138.5, 137.2, 134.9, 134.8, 130.4, 130.3, 129.3, 128.4, 127.9, 127.8, 127.4, 127.3, 127.0, 126.9, 73.4, 73.3, 69.4, 69.3, 61.9, 55.7, 55.6, 51.6, 51.5, 41.1, 40.0, 39.4, 34.1, 33.6, 33.4, 32.7, 32.6, 26.4, 26.2, 26.1, 15.7, 15.6, 14.1; HRFABMS calcd for C$_{32}$H$_{41}$N$_3$O$_7$ClS 646.2354, found 646.2347.

Ethyl 2-[4-(benzyloxy)-3-((2R)-3-cyclohexyl-2-[(4-methylbenzoyl)amino]propanoylamino)-2-oxobutanoyl]aminoacetate (22)

The title compound, a white powder, was prepared in the same manner as was Compound 1.

$^1$H NMR (CDCl$_3$, 400 MHz, mixture of two diastereomers) δ 7.68-7.65 (m, 2H), 7.42 and 7.38 (t, J=5.2, 5.6 Hz, 1H), 7.28-7.15 (m, 7H), 7.05 (d, J=7.6 Hz, 0.5H), 6.66 (d, J=6.8 Hz, 1H), 5.48-5.44 (m, 1H), 4.83-4.76 (m, 1H), 4.42 and 4.39 (s and dd, J=18.6, 12.0 Hz, 2H), 4.24-4.12 (m, 3H), 4.00 (dd, J=5.6, 1.2 Hz, 1H), 3.97 (d, J=5.6 Hz, 1H), 3.77 and 3.73 (dd, J=9.8, 3.3 and 9.9, 3.4 Hz, 1H), 2.36 (s, 3H), 1.82-1.58 (m, 7H), 1.38-1.36 (m, 1H), 1.29-1.20 (m, 4H), 1.16-1.13 (m, 2H), 0.98-0.85 (m, 2H); $^{13}$C NMR (CDCl$_3$, 100 MHz, mixture of two diastereomers) δ192.8, 172.1, 172.0, 168.5, 167.4, 167.1, 159.1, 159.0, 142.2, 137.2, 131.1, 129.2, 128.4, 127.8, 127.7, 127.6, 127.1, 73.4, 69.3, 61.8, 55.6, 55.5, 51.2, 41.1, 40.2, 39.8, 34.3, 34.2, 33.6, 32.9, 32.8, 26.4, 26.1, 26.0, 21.4, 14.1; HRFABMS calcd for C$_{32}$H$_{41}$N$_3$O$_7$Na 602.2842, found 602.2838.

Ethyl 2-[4-(benzyloxy)-3-((2R)-3-cyclohexyl-2-[(2,3-difluorobenzoyl)amino]propanoylamino)-2-oxobutanoyl]aminoacetate (26)

The title compound, a white powder, was prepared in the same manner as was Compound 1.

$^1$H NMR (CDCl$_3$, 400 MHz, mixture of two diastereomers) δ 7.73 (tt, J=8.0, 1.7 Hz, 1H), 7.36-7.26 (m, 4H), 7.23-7.12 (m, 3H), 7.05 (d, J=8.0 Hz, 1H), 6.98-6.90 (m, 2H), 5.50-5.46 (m, 1H), 4.80-4.73 (m, 1H), 4.48-4.39 (m, 2H), 4.25-4.16 (m, 3H), 4.00 (t, J=6.3 Hz, 2H), 3.80 and 3.55 (dd, J=5.6, 3.4 Hz and 5.6, 3.3 Hz, 1H), 1.81-1.59 (m, 7H), 1.42-1.36 (m, 1H), 1.30-1.25 (m, 3H), 1.23-1.11 (m, 3H), 1.03-0.84 (m, 2H); $^{13}$C NMR (CDCl$_3$, 100 MHz, mixture of two diastereomers) δ192.8, 171.5, 168.5, 162.2, 159.0, 151.6 (d, J=14.1 Hz), 150.1 (d, J=14.1 Hz), 149.1 (d, J=14.2 Hz), 147.6 (d, J=14.0 Hz), 137.1, 128.3, 127.8, 127.7, 127.6, 126.2, 124.5, 123.1 (d, J=13.2 Hz), 120.3 (d, J=17.1 Hz), 73.3, 69.3, 61.8, 55.6, 51.5, 41.0, 40.0, 34.0, 33.5, 32.7, 26.3, 26.1, 26.0, 14.1; HRFABMS calcd for C$_{31}$H$_{37}$N$_3$O$_7$NaF$_2$ 624.2497, found 624.2489.

Ethyl 2-[4-(benzyloxy)-3-((2R)-3-cyclohexyl-2-[(2,5-difluorobenzoyl)amino]propanoylamino)-2-oxobutanoyl]aminoacetate (45)

The title compound, a white powder, was prepared in the same manner as was Compound 1.

$^1$H NMR (CDCl$_3$, 400 MHz) δ 7.71 (ddd, J=8.6, 5.8, 3.1 Hz, 1H), 7.35 (t, J=5.5 Hz, 1H), 7.28-7.22 (m, 3H), 7.21-7.16 (m, 2H), 7.15-7.05 (m, 3H), 6.94 (d, J=7.7 Hz, 1H), 5.50-5.46 (m, 1H), 4.78-4.72 (m, 1H), 4.42 (dd, J=14.1, 12.1 Hz, 2H), 4.22 (q, J=7.2 Hz, 2H), 4.18 (dd, J=9.9, 3.6 Hz, 1H), 4.01 (d, J=5.6 Hz, 2H), 3.77 (dd, J=9.9, 3.3 Hz, 1H), 1.81-1.59 (m, 7H), 1.42-1.37 (m, 1H), 1.28 (t, J=7.1 Hz, 3H), 1.25-1.10 (m, 3H), 1.04-0.86 (m, 2H); $^{13}$C NMR (CDCl$_3$, 100 MHz,) δ192.9, 171.5, 168.5, 161.9, 159.2, 158.7 (d, J=242.7 Hz), 156.4 (d, J=243.7 Hz), 137.1, 128.3, 127.7, 127.6, 122.2 (dd, J=14.3, 7.2 Hz), 120 (dd, J=24.0, 10.0 Hz), 118.0 (d, J=24.8 Hz), 117.46 (dd, J=27.7, 8.2 Hz), 73.3, 69.4, 61.7, 55.6, 51.5, 41.0, 40.0, 34.0, 33.4, 32.8, 26.3, 26.0, 25.9, 14.0; HRFABMS calcd for $C_{31}H_{37}N_3O_7NaF_2$ 624.2497, found 624.2502.

Methyl 4-([(1R)-2-((1R)-1-[(benzyloxy)methyl]-3-[(2-ethoxy-2-oxoethyl)amino]-2,3-dioxopropylamino)-1-(cyclohexylmethyl)-2-oxoethyl]aminocarbonyl)-2-[(tert-butoxycarbonyl)amino]benzoate (56)

The title compound, a white powder, was prepared in the same manner as was Compound 1.

$^1$H NMR (CDCl$_3$, 400 MHz) δ 10.23 (s, 1H), 8.79 (d, J=1.5 Hz, 1H), 7.99 (d, J=8.3 Hz, 1H), 7.42 (t, J=5.5 Hz, 1H), 7.39 (dd, J=8.3, 1.7 Hz, 1H), 7.26-7.16 (m, 5H), 7.04 (d, J=7.7 Hz, 1H), 6.89 (d, J=8.2 Hz, 1H), 5.49-5.45 (m, 1H), 4.80-4.75 (m, 1H), 4.43 and 4.41 (s and dd, J=21.2, 12.0, 2H), 4.21 (q, J=7.2 Hz, 2H), 4.16 (dd, J=9.8, 3.5 Hz, 1H), 4.01 (dd, J=5.4, 1.2 Hz, 2H), 3.91 (s, 3H), 3.76 (dd, J=9.9, 3.3 Hz, 1H), 1.81-1.74 (m, 3H), 1.68-1.60 (m, 4H), 1.50 (s, 9H), 1.44-1.38 (m, 1H), 1.26 (t, J=7.1 Hz, 3H), 1.23-1.10 (m, 3H), 1.02-0.87 (m, 2H); $^{13}$C NMR (CDCl$_3$, 100 MHz) δ 192.8 171.8, 168.5, 167.9, 166.4, 159.1, 152.6, 142.4, 139.3, 137.2, 131.3, 128.4, 127.8, 127.7, 120.0, 116.9, 116.4, 80.9, 73.3, 69.3, 61.8, 55.6, 52.4, 51.4, 41.0, 40.0, 34.1, 33.5, 32.9, 18.2, 26.4, 26.1, 26.0, 14.1; HRFABMS calcd for $C_{38}H_{51}N_4O_{11}$ 739.3554, found 739.3562.

Ethyl 2-[((3R)-4-(benzyloxy)-3-[(2R)-2-(5-bromo-2-[(tert-butoxycarbonyl)amino]benzoylamino)-3-cyclohexylpropanoyl]amino-2-oxobutanoyl)amino]acetate (52)

The title compound, a white powder, was prepared in the same manner as was Compound 1.

$^1$H NMR (CDCl$_3$, 400 MHz) δ 9.99 and 9.93 (s, 1H), 8.23 (d, J=9.0 Hz, 1H), 7.56 (d, J=2.1 Hz, 1H), 7.45 (d, J=9.0, 2.0 Hz, 1H), 7.36 (t, J=5.2 Hz, 1H), 7.29-7.17 (m, 5H), 6.98 (d, J=8.0 Hz, 1H), 6.76 (d, J=7.8 Hz, 1H), 5.50-5.46 (m, 1H), 4.74-4.69 (m, 1H), 4.43 (dd, J=17.6, 12.2 Hz, 2H), 4.22 (q, J=7.1 Hz, 2H), 4.19 (dd, J=5.5, 4.1 Hz, 1H), 4.01 (d, J=5.6 Hz, 2H), 3.79 (dd, J=9.9, 3.2 Hz, 1H), 1.83 (d, J=12.0 Hz, 1H), 1.74-1.58 (m, 7H), 1.47 (s, 9H), 1.36-1.31 (m, 1H), 1.28 (t, J=7.1 Hz, 3H), 1.24-1.11 (m, 2H), 1.01-0.86 (m, 2H); $^{13}$C NMR (CDCl$_3$, 100 MHz) δ 192.7, 171.8, 168.5, 167.2, 159.0, 152.7, 139.4, 137.0, 135.2, 129.4, 128.4, 128.0, 127.8, 121.4, 120.7, 113.6, 80.5, 73.4, 69.2, 61.9, 55.7, 51.2, 41.0, 40.5, 34.1, 33.6, 32.8, 28.3, 26.3, 26.1, 26.0, 14.1; HRFABMS calcd for $C_{37}H_{48}N_3O_9Br$ 757.2574, found 757.2571.

Ethyl 2-[(4-(benzyloxy)-3-[(2R)-2-(3-[(tert-butoxycarbonyl)amino]-4-chloro benzoylamino)-3-cyclohexylpropanoyl]amino-2-oxobutanoyl)amino]acetate (49)

The title compound, a white powder, was prepared in the same manner as was Compound 1.

$^1$H NMR (CDCl$_3$, 400 MHz, mixture of two diastereomers) δ 8.53 (s, 1H), 7.44-7.38 (m, 2H), 7.34 (d, J=8.3 and 8.4 Hz, 1H), 7.27-7.15 (m, 5H), 7.05 (d, J=7.7 Hz, 0.7H), 7.01 (s, 1H), 6.87 (d, J=8.2 Hz, 0.3H), 6.82 (d, J=8.2 Hz, 0.7H), 5.49-5.43 (m, 1H), 4.81-4.74 (m, 1H), 4.42 and 4.36 (s and dd, J=21.2, 12.1 Hz, 2H), 4.40 (q, J=7.2 Hz, 2H), 4.15 (dd, J=10.0, 3.8 Hz, 1H), 4.01 and 3.98 (dd and d, J=5.5, 1.0 and 5.6 Hz, 2H), 3.75 (dd, J=9.9, 3.3 Hz, 1H), 1.81-1.73 (m, 3H), 1.66-1.59 (m, 4H), 1.50 (s, 9H), 1.44-1.35 (m, 1H), 1.26 (t, J=7.1 Hz, 3H), 1.23-1.09 (m, 2H), 1.01-0.86 (m, 2H); $^{13}$C NMR (CDCl$_3$, 100 MHz, mixture of two diastereomers) δ 192.8, 171.9, 168.5, 166.5, 166.3, 159.1, 152.1, 137.2, 135.3, 133.6, 129.2, 128.4, 127.8, 127.7, 127.6, 125.0, 122.4, 122.3, 117.9, 81.5, 73.3, 69.3, 61.8, 55.6, 51.4, 41.0, 40.0, 39.6, 34.2, 34.1, 33.5, 32.9, 28.2, 26.4, 26.1, 26.0, 14.1; HRFABMS calcd for $C_{36}H_{48}N_4O_9Cl$ 715.3110, found 715.3113.

Methyl 2-amino-4-([(1R)-2-(1-[(benzyloxy)methyl]-3-[(2-ethoxy-2-oxoethyl)amino]-2,3-dioxopropylamino)-1-(cyclohexylmethyl)-2-oxoethyl]aminocarbonyl)benzoate (21)

Compound 56 was dissolved in CH$_2$Cl$_2$, and TFA was added under 0° C. The solution was stirred for 30 min and then concentrated. Purification by chromatography (silica, 1/1: Hexane/EtOAc, R$_f$=0.3) afforded compound 21 as a white solid.

$^1$H NMR (CDCl$_3$, 400 MHz, mixture of two diastereomers) δ 7.84 and 7.82 (d, J=8.3 and 8.2 Hz, 1H), 7.42 (t, J=5.4 Hz, 1H), 7.27-7.15 (m, 5H), 7.05 and 7.04 (s, 1H), 7.03 (d, J=7.8 Hz, 1H), 6.89 and 6.88 (dd, J=8.3 Hz, 1H), 6.77 (d, J=8.1 Hz, 1H), 5.48-5.44 (m, 1H), 4.77 (dd and, J=6.0 and 21.0, 5.9 Hz, 1H), 4.43 and 4.40 (s and dd, J=18.3, 12.0, 2H), 4.22 (q, J=7.1 Hz, 2H), 4.15 (dd, J=10.0, 3.7 Hz, 1H), 4.01 and 3.97 (dd and d, J=5.5, 3.6 and 5.6 Hz, 2H), 3.86 and 3.85 (s, 3H), 3.78 and 3.73 (dd, J=9.9, 3.3 and 9.9, 3.3 Hz, 1H), 1.81-1.57 (m, 7H), 1.37-1.35 (m, 1H), 1.27 (t, J=7.1 Hz, 3H), 1.24-1.10 (m, 3H), 1.00-0.86 (m, 2H); HRFABMS calcd for $C_{33}H_{43}N_4O_9$ 639.3030, found 639.3026.

Ethyl 2-[3-((2R)-2-[(2-amino-5-bromobenzoyl)amino]-3-cyclohexylpropanoyl amino)-4-(benzyloxy)-2-oxobutanoyl]aminoacetate (23)

The title compound, a white powder, was prepared in the same manner as was Compound 21.

$^1$H NMR (CDCl$_3$, 400 MHz) δ 7.42 (d, J=2.2 Hz, 1H), 7.32 (t, J=5.2 Hz, 1H), 7.29-7.23 (m, 5H), 7.1-7.18 (m, 2H), 6.86 (d, J=7.8 Hz, 1H), 6.53 (d, J=8.8 Hz, 1H), 6.43 (d, J=7.9 Hz, 1H), 5.48-5.44 (m, 1H), 4.71-5.65 (m, 1H), 4.43 (s, 2H), 4.23 (q, J=7.1 Hz, 2H), 4.17 (dd, J=10.0, 3.6 Hz, 1H), 4.02 (dd, J=5.5, 2.2 Hz, 2H), 3.78 (dd, J=9.8, 3.4 Hz, 1H), 1.82-1.56 (m, 8H), 1.39-1.36 (m, 1H), 1.28 (t, J=7.0 Hz, 3H), 1.25-1.12 (m, 2H), 1.03-0.86 (m, 2H); HRFABMS calcd for $C_{31}H_{40}N_4O_7Br$ 659.2080, found 659.2078.

Ethyl 2-[3-((2R)-2-[(3-amino-4-chlorobenzoyl)amino]-3-cyclohexylpropanoyl amino)-4-(benzyloxy)-2-oxobutanoyl]aminoacetate (4)

The title compound, a white powder, was prepared in the same manner as was Compound 21.

$^1$H NMR (CDCl$_3$, 400 MHz, mixture of two diastereomers) δ 7.36 (t, J=5.1 Hz, 1H), 7.28-7.21 (m, 5H), 7.19-7.17 (m, 2H), 7.10 (d, J=7.2 Hz, 0.3H), 6.99 (dd, J=8.2, 2.0 Hz, 1H), 6.95 (d, J=7.6 Hz, 1H), 6.64 (d, J=8.1 Hz, 1H), 5.47-5.44 (m, 1H), 4.77-4.70 (m, 1H), 4.43 and 4.41 (s and dd, J=17.3, 11.9 Hz, 2H), 4.22 (q, J=7.2 Hz, 2H), 4.16 (dd, J=9.8, 3.5 Hz, 1H), 4.01 and 3.98 (dd and d, J=5.4, 3.2 and 5.6 Hz, 2H), 3.78 and 3.76 (dd, J=9.9, 3.3 Hz, 1H), 1.81-1.56 (m, 7H), 1.35 (s, 1H), 1.28 (t, J=7.2 Hz, 3H), 1.25-1.14 (m, 3H), 1.01-0.86 (m, 2H). HRFABMS calcd for $C_{31}H_{40}N_4O_7Cl$ 615.2586, found 615.2592.

Ethyl 2-(4-(benzyloxy)-3-[((2R)-3-cyclohexyl-2-[(E)-3-(2,5-dimethoxyphenyl)-2-propenoyl]amino-propanoyl)amino]-2-oxobutanoylamino)acetate (9)

The title compound, a white powder, was prepared in the same manner as was Compound 1.

$^1$H NMR (CDCl$_3$, 400 MHz, mixture of two diastereomers) δ 7.84 and 7.83 (d, J=15.8 Hz, 1H), 7.40-7.39 (m, 1H), 7.28-7.17 (m, 5H), 7.11 (d, J=7.4 Hz, 0.4H), 7.01-6.92 (m, 1.6H), 6.86 and 6.84 (d, J=2.6 Hz, 1H), 6.82 and 6.79 (s, 1H), 6.55 and 6.53 (d, J=15.8 Hz, 1H), 6.14 (s, 1H), 5.48-5.46 (m, 1H), 4.76-4.70 (m, 1H), 4.43 and 4.41 (s and dd, J=20.5, 12.0 Hz, 2H), 4.22 (q, J=7.2 Hz, 2H), 4.16 (dd, J=10.2, 3.4 Hz, 1H), 3.01 (dd, J=5.4, 1.8 Hz, 1H), 3.99 (d, J=5.6 Hz, 1H), 3.79 (s, 3H), 3.77-3.73 (m, 4H), 1.81-1.52 (m, 7H), 1.36-1.35 (m, 1H), 1.27 (t, J=7.0 Hz, 2H), 1.24-1.06 (m, 2H), 1.00-0.87 (m, 2H); $^{13}$C NMR (CDCl$_3$, 100 MHz, mixture of two diastereomers) δ 192.8, 172.1, 168.5, 166.2, 159.1, 153.5, 152.8, 137.2, 137.0, 128.4, 127.8, 127.7, 127.6, 73.3, 69.3, 61.8, 55.5, 55.4, 51.0, 50.9, 41.0, 40.1, 39.5, 38.6, 34.1, 33.4, 32.9, 26.4, 26.1, 26.0, 14.1; HRFABMS calcd for C$_{35}$H$_{45}$N$_3$O$_9$Na 674.3054, found 674.3070.

Ethyl 2-(4-(benzyloxy)-3-[(2R)-(2-[(5-bromo-2-furyl)carbonyl]amino-3-cyclohexylpropanoyl)amino]-2-oxobutanoylamino)acetate (5)

The title compound, a white powder, was prepared in the same manner as was Compound 1.

$^1$H NMR (CDCl$_3$, 400 MHz, mixture of two diastereomers) δ 7.34-7.25 (m, 4H), 7.21-7.17 (m, 2H), 7.07-7.05 (m, 1H), 6.94 (d, J=7.5 Hz, 0.4H), 6.82 (d, J=8.0 Hz, 0.6H), 6.68-6.64 (m, 1H), 6.42 (d, J=3.2 Hz, 1H), 5.49-5.45 (m, 1H), 4.72-4.66 (m, 1H), 4.43 and 4.42 (s and dd, J=15.8, 11.8 Hz, 2H), 4.26-4.15 (m, 3H), 4.01 (t, J=5.6 Hz, 2H), 3.80-3.74 (m, 1H), 1.82-1.56 (m, 8H), 1.36-1.35 (m, 1H), 1.31-1.25 (m, 3H), 1.23-1.11 (m, 2H), 0.99-0.81 (m, 2H); $^{13}$C NMR (CDCl$_3$, 100 MHz, mixture of two diastereomers) δ192.8, 171.6, 168.5, 159.0, 158.9, 149.0, 137.1, 128.4, 127.8, 127.7, 124.8, 117.1, 117.0, 114.1, 73.3, 69.3, 61.8, 55.6, 50.5, 41.0, 40.3, 40.0, 34.0, 33.9, 33.5, 32.7, 32.6, 26.3, 26.1, 26.0, 14.1; HRFABMS calcd for C$_{29}$H$_{37}$N$_3$O$_8$Br 634.1764, found 634.1768.

Ethyl 2-(4-(benzyloxy)-3-[((2R)-3-cyclohexyl-2-[2,3-dioxo-3-(2-thienyl)propanoyl]aminopropanoyl)amino]-2-oxobutanoylamino)acetate (25)

The title compound, a white powder, was prepared in the same manner as was Compound 1.

$^1$H NMR (CDCl$_3$, 400 MHz) δ 8.38 (dd, J=4.0, 1.2 Hz, 1H), 7.80 (dd, J=4.8, 1.2 Hz, 1H), 7.64 (d, J=8.6 Hz, 1H), 7.35 (t, J=5.6 Hz, 1H), 7.30-7.26 (m, 1H), 7.23-7.15 (m, 4H), 6.86 (d, J=7.8 Hz, 1H), 5.48-5.44 (m, 1H), 4.57 (td, J=8.8, 5.8 Hz, 1H), 4.42 (dd, J=13.9, 12.2 Hz, 2H), 4.22 (q, J=7.1 Hz, 2H), 4.18 (dd, J=9.9, 3.6 Hz, 2H), 4.00 (dd, J=5.8, 0.6 Hz, 2H), 3.77 (dd, J=9.9, 3.3 Hz, 1H), 1.80-1.72 (m, 2H), 1.69-1.58 (m, 5H), 1.37-1.31 (m, 1H), 1.30-1.23 (m, 4H), 1.22-1.10 (m, 2H), 1.02-0.84 (m, 2H); $^{13}$C NMR (CDCl$_3$, 100 MHz) δ 192.8, 177.7, 170.8, 168.5, 160.6, 159.1, 138.5, 138.1, 137.1, 136.9, 128.4, 128.3, 127.8, 127.7, 73.3, 69.3, 61.8, 58.7, 55.7, 51.2, 41.0, 39.8, 34.0, 33.5, 32.7, 26.3, 26.0, 25.9, 14.1; HRFABMS calcd for C$_{30}$H$_{38}$N$_3$O$_8$S 600.2380, found 600.2372.

Ethyl 2-(4-(benzyloxy)-3-[(2R)-(3-cyclohexyl-2-[2-(2-thienyl)acetyl]amino-propanoyl)amino]-2-oxobutanoylamino)acetate (30)

The title compound, a white powder, was prepared in the same manner as was Compound 1.

$^1$H NMR (CDCl$_3$, 400 MHz, mixture of two diastereomers) δ 7.34-7.25 (m, 3H), 7.22-7.19 (m, 3H), 6.98-6.95 (m, 1H), 6.93-6.91 (m, 1H), 6.82 (d, J=7.7 Hz, 1H), 6.02-5.07 (m, 1H), 5.45-5.41 (m, 1H), 4.54-4.50 (m, 1H), 4.43 and 4.42 (s and dd, J=18.3, 12.0 Hz, 2H), 4.23 (q, J=7.3 Hz, 2H), 4.16 (dd, J=9.8, 3.6 Hz, 1H), 4.01 (d, J=5.5 Hz, 2H), 3.78-3.72 (m, 3H), 1.63-1.57 (m, 8H), 1.44-1.36 (m, 1H), 1.30-1.26 (m, 3H), 1.19-1.11 (m, 2H), 0.93-0.82 (m, 2H); $^{13}$C NMR (CDCl$_3$, 100 MHz, mixture of two diastereomers) δ192.7, 171.6, 169.7, 168.5, 159.0, 137.2, 135.8, 128.5, 127.9, 127.7, 127.5, 127.4, 125.6, 73.4, 69.3, 61.9, 55.6, 55.5, 51.0, 50.9, 41.1, 39.7, 37.5, 34.0, 33.5, 32.7, 29.7, 26.3, 26.2, 26.0, 14.1; HRFABMS calcd for C$_{30}$H$_{39}$N$_3$O$_7$NaS 608.2406, found 608.2415.

Ethyl 2-(4-(benzyloxy)-3-[((2R)-3-cyclohexyl-2-[(5-nitro-2-thienyl)carbonyl]aminopropanoyl)amino]-2-oxobutanoylamino)acetate (43)

The title compound, a white powder, was prepared in the same manner as was Compound 1.

$^1$H NMR (CDCl$_3$, 400 MHz, mixture of two diastereomers) δ 7.87 (d, J=7.9 Hz, 1H), 7.72 and 7.70 (d, J=4.6 and 4.8 Hz, 1H), 7.52 and 7.46 (t, J=5.6 and 5.5 Hz, 1H), 7.41 and 7.35 (d, J=4.0 and 7.5 Hz, 1H), 7.29-7.22 (m, 3H), 7.21-7.16 (m, 2H), 7.09 (d, J=7.8 Hz, 1H), 5.49-5.46 (m, 1H), 4.83-4.72 (m, 1H), 4.43 and 4.41 (s and dd, J=22.1, 12.1 Hz, 2H), 4.22 and 4.19 (q, J=7.1 and 7.3 Hz, 2H), 4.17-4.13 (m, 1H), 4.03-3.96 (m, 2H), 3.76 and 3.73 (dd, J=10.0, 3.1 Hz, 1H), 1.76-1.60 (m, 7H), 1.41-1.31 (m, 1H), 1.27 (t, J=7.1 Hz, 3H), 1.24-1.07 (m, 2H), 0.96-0.85 (m, 2H); $^{13}$C NMR (CDCl$_3$, 100 MHz, mixture of two diastereomers) δ 192.6, 172.5, 168.6, 160.1, 159.1, 154.4, 144.5, 137.0, 128.4, 128.3, 127.9, 127.7, 127.6, 126.6, 73.4, 69.0, 61.9, 55.7, 51.8, 41.0, 34.1, 33.5, 32.7, 26.3, 26.0, 25.9, 14.1; HRFABMS calcd for C$_{29}$H$_{36}$N$_4$O$_9$NaS 639.2101 found 639.2108.

Ethyl 2-[(4-(benzyloxy)-3-[(2R)-2-(2-butynoy-lamino)-3-cyclohexylpropanoyl]amino-2-oxobu-tanoyl)amino]acetate (14)

The title compound, a white powder, was prepared in the same manner as was Compound 1.

$^1$H NMR (CDCl$_3$, 400 MHz, mixture of two diastereomers) δ 7.37 (t, J=5.2 Hz, 1H), 7.31-7.26 (m, 3H), 7.22-7.18 (m, 2H), 6.94 (d, J=7.6 Hz, 0.2 H), 6.83 (d, J=7.7 Hz, 0.7H), 6.32 (d, J=8.5 Hz, 1H), 5.46-5.44 (m, 1H), 4.61-4.54 (m, 1H), 4.43 and 4.42 (s and dd, J=19.5, 12.1 Hz, 2H), 4.22 (q, J=7.1 Hz, 2H), 4.18-4.13 (m, 1H), 4.02-3.99 (m, 2H), 3.74 (dd, J=9.9, 3.3 Hz, 1H), 1.92 (s, 3H), 1.75 (d, J=12.2 Hz, 1H), 1.68-1.61 (m, 6H), 1.53-1.46 (m, 1H), 1.34-1.31 (m, 1H), 1.27 (t, J=7.2 Hz, 3H), 1.23-1.09 (m, 2H), 0.98-0.82 (m, 2H); $^{13}$C NMR (CDCl$_3$, 100 MHz, mixture of two diastereomers) δ 192.7, 171.3, 168.5, 159.1, 153.1, 137.2, 128.4, 127.9, 127.7, 84.5, 74.5, 73.4, 69.3, 61.8, 55.6, 51.0, 41.0, 40.1, 34.0, 33.9, 33.5, 32.8, 32.7, 26.3, 26.1, 25.9, 14.1, 3.65; HRFABMS calcd for C$_{28}$H$_{38}$N$_3$O$_7$ 528.2710, found 528.2710.

Ethyl 2-(4-(benzyloxy)-3-[((2R)-3-cyclohexyl-2-[(1-methylcyclopropyl)carbonyl]aminopropanoyl)amino]-2-oxobutanoylamino)acetate (12)

The title compound, a white powder, was prepared in the same manner as was Compound 1.

$^1$H NMR (CDCl$_3$, 400 MHz, mixture of two diastereomers) δ 7.44 (t, J=5.4 Hz, 1H), 7.30-7.23 (m, 3H), 7.21-7.17 (m, 2H), 7.00 (d, J=7.3 Hz, 1H), 6.18 (d, J=8.1 Hz, 1H), 5.48-5.42 (m, 1H), 4.60 and 4.55 (dd, J=8.4, 6.5 and 8.3, 6.4 Hz, 1H), 4.42 and 4.41 (s and dd, J=20.0, 12.0 Hz, 2H), 4.21 (q, J=7.2 Hz, 2H), 4.15 and 4.13 (dd, J=3.6, 2.3 and 3.7, 2.4 Hz, 1H), 4.01-3.98 (m, 2H), 3.76 and 3.73 (dd, J=5.0, 3.6 and 5.0, 3.4 Hz, 1H), 1.74-1.63 (m, 7H), 1.53-1.46 (m, 1H), 1.30-1.25 (m, 7H), 1.22-1.09 (m, 3H), 0.98-0.82 (m, 2H), 0.55 (s, 3H); $^{13}$C NMR (CDCl$_3$, 100 MHz, mixture of two diastereomers) δ 192.8 175.0, 172.2, 168.5, 159.1, 137.2, 128.4, 127.8, 127.7, 127.6, 73.3, 69.3, 61.8, 55.5, 55.4, 51.0, 50.9, 41.0, 40.1, 39.5, 38.6, 34.1, 33.4, 32.9, 26.3, 26.1, 26.0, 19.4, 19.0, 16.2, 16.1, 14.1; HRFABMS calcd for C$_{29}$H$_{41}$N$_3$O$_7$Na 566.2842, found 566.2834.

Ethyl 2-(4-(benzyloxy)-3-[(2R)-(3-cyclohexyl-2-[(2,2-dimethyl-4-oxo-3,4-dihydro-2H-6-pyranyl)carbonyl]aminopropanoyl)amino]-2-oxobutanoyl amino)acetate (13)

The title compound, a white powder, was prepared in the same manner as was Compound 1.

$^1$H NMR (CDCl$_3$, 400 MHz, mixture of two diastereomers) δ 7.38 (t, J=5.4 Hz, 1H), 7.31-7.25 (m, 3H), 7.20-7.17 (m, 2H), 7.10-7.05 (m, 1H), 6.96 (d, J=7.6 Hz, 0.3H), 6.85 (d, J=7.8 Hz, 0.6H), 6.27 and 6.26 (s, 1H), 5.50-5.46 (m, 1H), 4.66-4.60 (m, 1H), 4.43 and 4.42 (s and dd, J=15.0, 12.0 Hz, 2H), 4.23 (q, J=7.1 Hz, 2H), 4.20-4.15 (m, 1H), 4.02-3.99 (m, 2H), 3.75 (dd, J=9.8, 3.2 Hz, 1H), 2.55-2.45 (m, 2H), 1.98 (s, 1H), 1.76-1.53 (m, 8H), 1.46-1.44 (m, 6H), 1.30-1.10 (m, 5H), 1.01-0.78 (m, 2H); $^{13}$C NMR (CDCl$_3$, 100 MHz, mixture of two diastereomers) δ193.0, 192.6, 171.1, 168.5, 160.8, 160.6, 159.0, 158.9, 158.5, 158.4, 137.1, 137.0, 128.5, 128.0, 127.7, 127.6, 105.2, 105.1, 83.4, 73.4, 69.2, 61.9, 55.7, 55.6, 51.1, 47.7, 41.1, 40.3, 39.8, 34.2, 34.1, 33.4, 33.0, 32.9, 29.7, 26.3, 26.0, 25.9, 25.8, 25.8, 14.1; HRFABMS calcd for C$_{32}$H$_{43}$N$_3$O$_9$Na 636.2897 found 636.2906.

Ethyl 2-(4-(benzyloxy)-3-[((2R)-3-cyclohexyl-2-[(6-methyl-2-pyrazinyl)carbonyl]aminopropanoyl)amino]-2-oxobutanoylamino)acetate (24)

The title compound, a white powder, was prepared in the same manner as was Compound 1.

$^1$H NMR (CDCl$_3$, 400 MHz, mixture of two diastereomers) δ 9.23 and 9.22 (s, 1H), 8.37 (s, 1H), 8.06 (d, J=8.3 Hz, 1H), 7.34 (t, J=5.0 Hz, 1H), 7.29-7.15 (m, 5H), 7.05 (d, J=7.7 Hz, 0.3H), 6.94 (d, J=7.6 Hz, 0.7H), 5.50-5.47 (m, 1H), 4.74 (dd and d, J=17.3, 5.9 and 5.7 Hz, 1H), 4.42 and 4.40 (s and dd, J=14.1, 12.5 Hz, 2H), 4.22 (q, J=7.2 Hz, 2H), 4.17 (dd, J=9.9, 3.5 Hz, 1H), 3.01 and 3.99 (d, J=5.5 and 5.6 Hz, 2H), 3.78 and 3.76 (dd, J=11.0, 3.3 and 10.0, 3.3 Hz, 1H), 2.62 (s, 3H), 1.84-1.61 (m, 8H), 1.36-1.35 (m, 1H), 1.28 (t, J=7.0 Hz, 3H), 1.24-1.10 (m, 2H), 1.03-0.84 (m, 2H); $^{13}$C NMR (CDCl$_3$, 100 MHz, mixture of two diastereomers) δ 192.7, 171.5, 168.5, 163.5, 163.3, 159.0, 157.3, 143.4, 142.5, 137.2, 128.4, 127.8, 127.7, 127.6, 73.4, 69.3, 61.9, 55.6, 50.9, 41.1, 39.9, 34.1, 33.6, 32.7, 26.3, 26.1, 26.0, 14.1; HRFABMS calcd for C$_{30}$H$_{40}$N$_5$O$_7$ 582.2928, found 582.2950.

Ethyl 2-[4-(benzyloxy)-3-((2R)-3-cyclohexyl-2-[(2-phenoxypropanoyl)amino]propanoylamino)-2-oxobutanoyl]aminoacetate (37)

The title compound, a white powder, was prepared in the same manner as was Compound 1.

HRFABMS calcd for C$_{33}$H$_{43}$N$_3$O$_8$Na 632.2948, found 632.2939.

Ethyl 2-(4-(benzyloxy)-3-[((2R)-3-cyclohexyl-2-[(2-oxo-6-pentyl-2H-3-pyranyl)carbonyl]aminopropanoyl)amino]-2-oxobutanoylamino)acetate (55)

The title compound, a white powder, was prepared in the same manner as was Compound 1.

$^1$H NMR (CDCl$_3$, 400 MHz, mixture of two diastereomers) δ 8.93 and 8.91 (s, 1H), 8.36 and 8.36 (d, J=7.1 and 7.0 Hz, 1H), 7.36 (t, J=5.5 Hz, 1H), 7.27-7.20 (m, 3H), 7.20-7.15 (m, 2H), 6.20 and 6.19 (d, J=7.1 Hz, 1H), 5.48-5.44 (m, 1H), 4.66-4.60 (m, 1H), 4.41 and 4.39 (s, 2H), 4.20 and 4.19 (q, J=7.1 Hz, 2H), 4.16-4.13 (m, 1H), 4.00-3.97 (m, 2H), 3.77 and 3.75 (dd, J=8.3, 3.3 Hz, 1H), 2.54 (t, J=7.6 Hz, 2H), 1.80-1.58 (m, 11H), 1.32-1.22 (m, 7H), 1.20-1.08 (m, 2H), 0.99-0.82 (m, 5H); $^{13}$C NMR (CDCl$_3$, 100 MHz, mixture of two diastereomers) δ 192.8, 192.7, 171.7, 171.6, 171.1, 168.5, 162.7, 162.5, 162.3, 159.0, 149.1, 137.4, 137.3, 128.3, 127.6, 127.5, 127.4, 114.8, 104.2, 73.2, 69.4, 61.7, 55.5, 51.5, 41.0, 39.0, 38.6, 34.0, 33.9, 33.6, 32.4, 31.0, 26.5, 26.3, 26.1, 25.9, 22.2, 14.1, 13.8; HRFABMS calcd for C$_{35}$H$_{47}$N$_3$O$_9$Na 676.3210, found 676.3200.

Ethyl 2-(4-(benzyloxy)-3-[(2R)-(3-cyclohexyl-2-[2-(1-naphthyl)acetyl]amino propanoyl)amino]-2-oxobutanoylamino)acetate (16)

The title compound, a white powder, was prepared in the same manner as was Compound 1.

$^1$H NMR (CDCl$_3$, 400 MHz, mixture of two diastereomers) δ 7.92-7.87 (m, 1H), 7.81-7.79 (m, 1H), 7.75 (d, J=8.0 Hz, 1H), 7.46-7.40 (m, 2H), 7.39-7.31 (m, 2H), 7.27-7.14 (m, 6H), 6.97 (d, J=7.6 Hz, 0.5H), 6.82 (d, J=7.6 Hz, 0.5H), 5.64-5.92 (m, 1H), 5.34-5.31 (m, 1H), 4.46-4.39 (m, 1H), 4.38 and 4.35 (s and dd, J=14.8, 12.2 Hz, 2H), 4.17 (dd, J=21.3, 5.0 and 7.1, 4.9 Hz, 2H), 4.10-4.00 (m, 2H), 3.95 and 3.94 (d, J=5.5 Hz, 2H), 3.92 and 3.88 (d, J=6.5 and 6.4 Hz, 2H), 3.67 and 3.64 (dd, J=10.1, 3.3 and 10.1, 3.4 Hz, 1H), 1.69-1.35 (m, 5H), 1.26-1.09 (m, 7H), 0.90-0.56 (m, 5H); $^{13}$C NMR (CDCl$_3$, 100 MHz, mixture of two diastereomers) δ192.7, 171.7, 171.1, 168.5, 159.0, 137.2, 133.9, 131.9, 130.7, 128.8, 128.5, 128.4, 127.8, 127.7, 126.8, 126.1, 125.6, 123.6, 120.1, 73.3, 69.3, 61.8, 55.5, 50.9, 41.5, 41.0, 33.7, 33.4, 32.3, 29.6, 26.2, 25.9, 25.8, 14.1; HRFABMS calcd for C$_{36}$H$_{44}$N$_3$O$_7$ 630.3188, found 0.630.3179.

Ethyl 2-(4-(benzyloxy)-3-[((2R)-3-cyclohexyl-2-[(1-methyl-1H-2-indolyl)carbonyl]aminopropanoyl)amino]-2-oxobutanoylamino)acetate (28)

The title compound, a white powder, was prepared in the same manner as was Compound 1.

$^1$H NMR (CDCl$_3$, 400 MHz, mixture of two diastereomers) δ 7.61 and 7.59 (d, J=0.6 and 0.7 Hz, 1H), 7.38-7.28 (m, 3H), 7.25-7.10 (m, 5H), 7.01 (d, J=7.7 Hz, 1H), 6.91 and 6.90 (m, 1H), 6.68 (t, J=7.8 Hz, 1H), 5.51-5.45 (m, 1H), 4.79-4.72 (m, 1H), 4.43 and 4.41 (s, and dd, J=15.7, 12.1 Hz, 2H), 4.25-4.16 (m, 3H), 4.01 and 3.98 (dd and d, J=5.5, 0.9 and 5.5 Hz, 2H), 3.96 (s, 3H), 3.81 and 3.78 (t, J=2.9 and 2.8

Hz, 1H), 1.84-1.60 (m, 8H), 1.41-1.39 (m, 1H), 1.29-1.24 (m, 3H), 1.22-1.10 (m, 2H), 1.05-0.86 (m, 2H); $^{13}$C NMR (CDCl$_3$, 100 MHz, mixture of two diastereomers) δ192.8, 192.7, 172.0, 171.9, 168.5, 162.6, 162.4, 159.1, 139.1, 137.2, 131.3, 128.4, 127.8, 127.7, 127.6, 126.3, 126.0, 124.2, 121.9, 120.5, 110.1, 104.4, 73.4, 69.3, 61.9, 55.7, 55.6, 50.9, 50.8, 41.0, 40.1, 39.5, 34.3, 34.2, 33.6, 32.8, 32.7, 31.5, 26.4, 26.2, 26.0, 14.1; HRFABMS calcd for C$_{34}$H$_{42}$N$_4$O$_7$Na 641.2951, found 641.2933.

Ethyl 2-[4-(benzyloxy)-3-((2R)-3-cyclohexyl-2-[(3,3,3-triphenylpropanoyl)amino]propanoylamino)-2-oxobutanoyl]aminoacetate (59)

The title compound, a white powder, was prepared in the same manner as was Compound 1.

$^1$H NMR (CDCl$_3$, 400 MHz, mixture of two diastereomers) δ 7.30-7.17 (m, 21H), 6.81 (d, J=7.7 Hz, 0.1H), 6.68 (d, J=7.5 Hz, 0.8H), 5.37-5.34 (m, 1H), 5.13 (d, J=7.6 Hz, 0.8H), 5.03 (d, J=7.7 Hz, 0.2H), 4.41 (dd, J=17.5, 12.0 Hz, 1H), 4.26-4.19 (m, 3H), 4.10 (dd, J=9.8, 3.8 Hz, 1H), 4.00 (d, J=5.4 Hz, 2H), 3.70 (dd, J=7.0, 3.4 Hz, 1H), 3.66 (d, J=15.0 Hz, 2H), 3.51 (d, J=15.2 Hz, 1H), 1.61 (m, 5H), 1.41 (d, J=10.3 Hz, 1H), 1.34-1.21 (m, 5H), 1.07-1.06 (m, 2H), 0.93-0.82 (m, 1H), 0.77-0.70 (m, 2H); $^{13}$C NMR (CDCl$_3$, 100 MHz, mixture of two diastereomers) δ 192.7, 171.6, 170.9, 170.7, 168.5, 159.1, 146.1, 137.3, 129.1, 128.4, 128.3, 128.2, 128.1, 127.6, 126.5, 73.3, 69.4, 61.8, 55.9, 55.4, 55.3, 50.5, 50.5, 48.8, 48.7, 41.0, 39.2, 38.8, 33.4, 33.3, 32.3, 32.2, 26.3, 26.0, 25.8, 14.1; HRFABMS calcd for C$_{45}$H$_{51}$N$_3$O$_7$Na 768.3625, found 768.3638.

Compound 66 was synthesized as shown below:

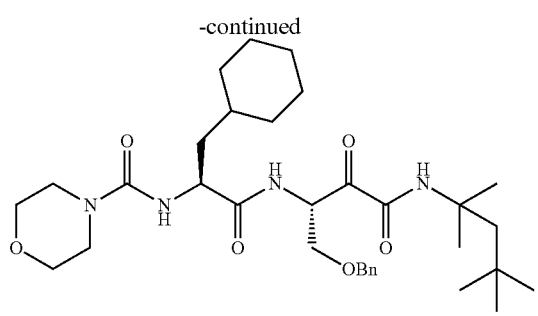

66

3-(Benzyloxy)-2-[(tert-butoxycarbonyl)amino]-1-[(1,1,3,3-tetramethylbutyl)amino]carbonylpropyl 2R)-2-[(tert-butoxycarbonyl)amino]-3-cyclohexylpropanoate (i)

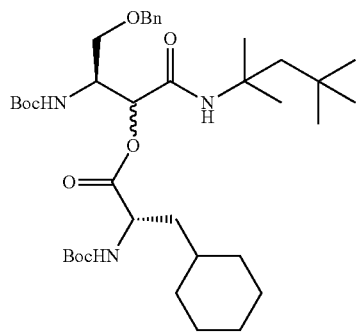 [SMILES: CC(C)(C)CC(C)(C)NC(=O)C(OC(=O)[C@H](CC1CCCCC1)NC(=O)OC(C)(C)C)[C@H](COCc1ccccc1)NC(=O)OC(C)(C)C]

tert-Butyl N-[(1R)-2-(benzyloxy)-1-(hydroxymethyl)ethyl]carbamate (450 mg, 1.6 mmole), Boc-Cha-OH (405 mg, 1.8 mmole), and 1,1,3,3-Tetramethylbutyl isocyanide (304 ul, 1.8 mmole) were dissolved in dry CH$_2$Cl$_2$ (16 mL). The solution was stirred for 48 h at room temperature, concentrated, and purified by chromatography (silica, : 1/4 Hexane/EtOAc, R$_f$=0.4) to give 3-(benzyloxy)-2-[(tert-butoxycarbonyl)amino]-1-[(1,1,3,3-tetramethylbutyl)amino]carbonylpropyl 2R)-2-[(tert-butoxy carbonyl)amino]-3-cyclohexylpropanoate as a white solid (914 mg, 83%).

N4-[(1S)-2-((1S)-1-[(benzyloxy)methyl]-2-hydroxy-3-oxo-3-[(1,1,3,3-tetramethylbutyl)amino]propylamino)-1-(cyclohexylmethyl)-2-oxoethyl]-4-morpholinecarboxamide (ii)

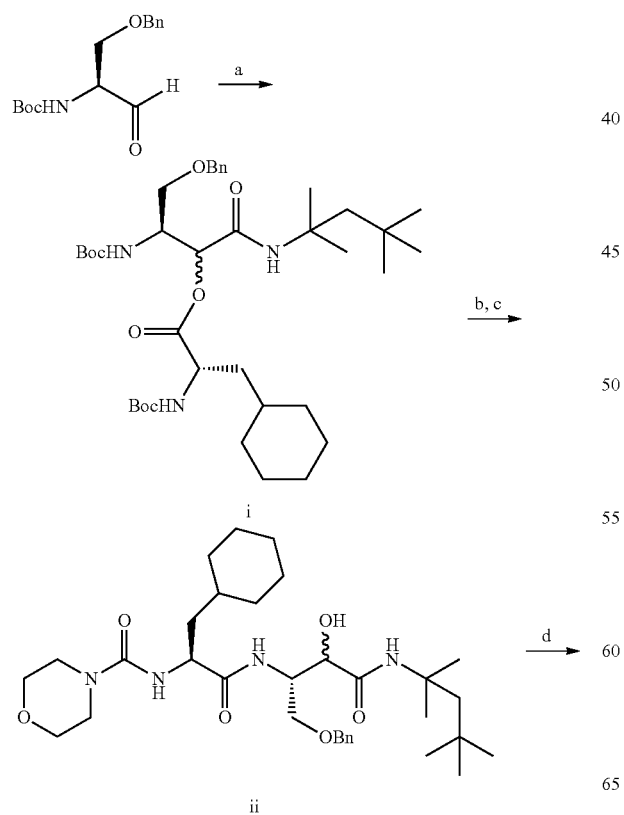

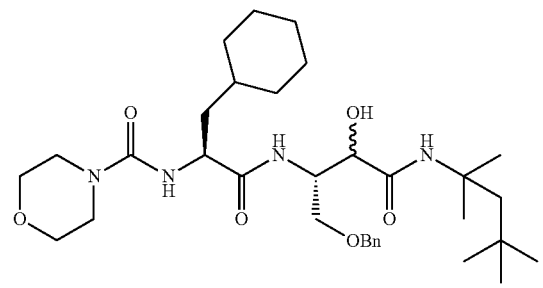 [SMILES: CC(C)(C)CC(C)(C)NC(=O)C(O)[C@H](COCc1ccccc1)NC(=O)[C@H](CC1CCCCC1)NC(=O)N1CCOCC1]

3-(Benzyloxy)-2-[(tert-butoxycarbonyl)amino]-1-[(1,1,3,3-tetramethylbutyl)amino]carbonylpropyl 2R)-2-[(tert-butoxy carbonyl)amino]-3-cyclohexylpropanoate was dissolved in 50% TFA in CH$_2$Cl$_2$. The solution was stirred for 30 min and then concentrated. The residue was redissolved in CH$_2$Cl$_2$ and neutralized with triethylamine. Stirring was continued for 10 min and then concentrated. Purification by chromatography (silica: Hexane/EtOAc with 10% MeOH, R$_f$=0.2) afforded N1-(1,1,3,3-tetramethylbutyl)-(3S)-3-[(2S)-2-amino-3-cyclohexylpropanoyl]amino-4-(benzyloxy)-2-hydroxybutanamide as a white solid.

N1-(1,1,3,3-tetramethylbutyl)-(3S)-3-[(2S)-2-amino-3-cyclohexylpropanoyl]amino-4-(benzyloxy)-2-hydroxybutanamide (360 mg, 0.7 mmole) was dissolved in DMF (7 mL), followed by addition of addition of triethylamine (205 ul, 1.5 mmole) and stirring under N$_2$ for 15 min. 4-Morpholinecarbonyl chloride (93 ul, 0.8 mmole) was added. Stirring was continued overnight and DMF was removed under reduced pressure. The solution was diluted with EtOAc and washed with water. The organic layer was dried over MgSO$_4$, filtered, and concentrated by rotary evaporation. Purification by chromatography (silica, Hexane/EtOAc with 10% MeOH, R$_f$=0.5) afforded N4-[(1S)-2-((1S)-1-[(benzyloxy)methyl]-2-hydroxy-3-oxo-3-[(1,1,3,3-tetramethylbutyl)amino]propylamino)-1-(cyclohexylmethyl)-2-oxoethyl]-4-Morpholinecarboxamide as a white solid (280 mg, 63%).

N4-[(1S)-2-((1S)-1-[(benzyloxy)methyl]-2,3-dioxo-3-[(1,1,3,3-tetramethylbutyl)amino]propylamino)-1-(cyclohexylmethyl)-2-oxoethyl]-4-morpholinecarboxamide (66a)

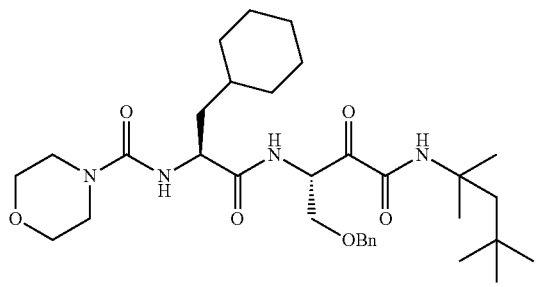 [SMILES: CC(C)(C)CC(C)(C)NC(=O)C(=O)[C@H](COCc1ccccc1)NC(=O)[C@H](CC1CCCCC1)NC(=O)N1CCOCC1]

N4-[(1S)-2-((1S)-1-[(benzyloxy)methyl]-2-hydroxy-3-oxo-3-[(1,1,3,3-tetramethyl butyl)amino]propylamino)-1-(cyclohexylmethyl)-2-oxoethyl]-4-Morpholinecarboxamide (260 mg, 0.4 mmole) was dissolved in CH$_2$Cl$_2$ (4 mL). Dess-Martin periodinane (550 mg, 1.2 mmole) was added. The solution was stirred for 2 h at room temperature and quenched with Na$_2$S$_2$O$_3$ and saturated bicarbonate solution. After extracting with CH$_2$Cl$_2$, the organic layer was dried over MgSO$_4$, filtered, and concentrated by rotary evaporation. Purification by chromatography (silica, 1/3: Hexane/EtOAc, R$_f$=0.6) afforded N4-[(1S)-2-((1S)-1-[(benzyloxy)methyl]-2,3-dioxo-3-[(1,1,3,3-tetramethylbutyl)amino]propylamino)-1-(cyclohexyl-methyl)-2-oxoethyl]-4-morpholinecarboxamide as a white solid (170 mg, 71%).

$^1$H NMR (CDCl$_3$, 400 MHz) δ 7.30-7.21 (m, 3H), 7.19-7.17 (m, 2H), 6.98 (d, J=7.2 Hz, 1H), 6.78 (s, 1H), 5.47 (ddd, J=7.8, 3.3, 1.7 Hz, 1H), 5.13 (d, J=6.8 Hz, 1H), 4.47-4.44 (m, 1H), 4.40 (dd, J=26.9, 12.1 Hz, 2H), 4.19 (dd, J=9.8, 3.6 Hz, 1H), 3.72 (dd, J=9.8, 3.4 Hz, 1H), 3.64-3.57 (m, 4H), 3.36-3.26 (m, 4H), 1.78-1.58 (m, 8H), 1.52-1.43 (m, 1H), 1.40 (s, 3H), 1.39 (s, 3H), 1.36-1.09 (m, 4H), 0.95 (s, 9H), 0.92-0.82 (m, 2H); $^{13}$C NMR (CDCl$_3$) δ194.6, 173.3, 157.9, 157.3, 137.2, 128.2, 127.6, 127.4, 73.2, 69.8, 66.3, 55.3, 55.1, 52.1, 51.5, 43.9, 40.3, 33.9, 33.4, 32.7, 31.5, 31.2, 28.4, 28.3, 26.3, 26.0, 25.9; HRFABMS calcd for C$_{33}$H$_{53}$N$_4$O$_6$ 601.3965, found 601.3963.

N4-[(1R)-2-((1R)-1-[(benzyloxy)methyl]-2,3-dioxo-3-[(1,1,3,3-tetramethylbutyl)amino]propylamino)-1-(cyclohexylmethyl)-2-oxoethyl]-4-morpholinecarboxamide (66b)

$^1$H NMR (CDCl$_3$, 400 MHz) δ 7.30-7.24 (m, 3H), 7.23-7.18 (m, 2H), 7.05 (d, J=7.6 Hz, 1H), 6.77 (s, 1H), 5.47 (ddd, J=7.7, 3.4, 1.6 Hz, 1H), 4.95 (d, J=7.9 Hz, 1H), 4.48-4.44 (m, 1H), 4.42 (s, 2H), 4.20 (dd, J=9.8, 3.5 Hz, 1H), 3.76 (dd, J=9.7, 3.3 Hz, 1H), 3.64-3.61 (m, 4H), 3.34-3.31 (m, 4H), 1.75-1.59 (m, 7H), 1.49-1.43 (m, 1H), 1.40 (s, 3H), 1.39 (s, 3H), 1.35-1.07 (m, 4H), 0.95 (s, 9H), 0.98-0.79 (m, 3H); $^{13}$C NMR (CDCl$_3$) δ194.6, 173.1, 157.8, 157.4, 137.3, 128.4, 127.8, 127.5, 73.3, 69.9, 66.4, 55.4, 55.3, 52.1, 51.7, 44.1, 40.1, 34.2, 33.5, 32.9, 31.6, 31.3, 28.5, 26.3, 26.1, 26.0; HRFABMS calcd for C$_{33}$H$_{53}$N$_4$O$_6$ 601.3965, found 601.3962.

N4-[(1R)-2-[1-[(benzyloxy)methyl]-3-(butylamino)-2,3-dioxopropyl]amino-1-(cyclohexylmethyl)-2-oxoethyl]-4-morpholinecarboxamide (67)

67

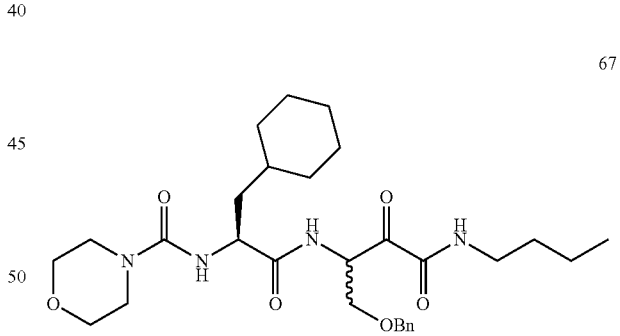

$^1$H NMR (CDCl$_3$, 400 MHz, mixture of two diastereomers) δ 7.32-7.25 (m, 3H), 7.21-7.18 (m, 2H), 7.12 and 6.94 (d, J=7.7 and 7.6 Hz, 1H), 6.89 (t, J=5.6 Hz, 1H), 5.49-5.45 (m, 1H), 4.99 and 4.96 (d, J=8.0 and 8.1 Hz, 1H), 4.50-4.38 (m, 3H), 4.21 and 4.19 (dd, J=9.8, 3.4 and 9.7, 3.2 Hz, 1H), 3.79 and 3.76 (dd, J=9.8, 3.2 and 10.0, 3.0 Hz, 1H), 3.64-3.62 (m, 4H), 3.34-3.31 (m, 4H), 3.29-3.22 (m, 2H), 1.77-1.59 (m, 7H), 1.53-1.44 (m, 3H), 1.37-1.27 (m, 2H), 1.23-1.09 (m, 3H), 0.96-0.85 (m, 5H); $^{13}$C NMR (CDCl$_3$, 100 MHz, mixture of two diastereomers) δ194.0, 193.9, 173.3, 159.0, 158.9, 157.4, 157.2, 137.3, 128.3, 127.7, 127.5, 127.4, 73.2, 69.7, 69.6, 66.3, 55.5, 55.4, 52.1, 51.9, 44.0, 43.9, 40.4, 40.0, 39.0, 34.1, 34.0, 33.5, 33.4, 32.7, 31.1, 26.3, 26.1, 26.0, 19.9, 13.6; HRESIMS calcd for $C_{29}H_{44}N_4O_6Na$ 567.3159, found 567.3162.

N4-[(1R)-2-[1-[(benzyloxy)methyl]-3-(cyclohexylamino)-2,3-dioxopropyl]amino-1-(cyclohexylmethyl)-2-oxoethyl]-4-morpholinecarboxamide (73)

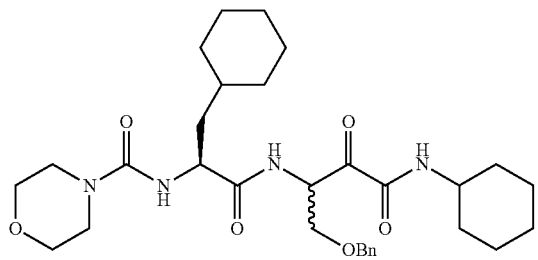

73

$^1$H NMR (CDCl$_3$, 400 MHz, mixture of two diastereomers) δ 7.32-7.22 (m, 3H), 7.21-7.17 (m, 2H), 7.13 and 6.95 (d, J=7.8 and 7.7 Hz, 1H), 6.76 (d, J=8.1 Hz, 1H), 5.49-5.45 (m, 1H), 5.05 and 5.01 (d, J=8.0 and 8.2 Hz, 1H), 4.47-4.37 (m, 3H), 4.20 (dd, J=9.8, 3.7 Hz, 1H), 3.78-3.74 (m, 1H), 3.72-3.67 (m, 1H), 3.64-3.61 (m, 4H), 3.37-3.28 (m, 4H), 1.86-1.59 (m, 12H), 1.54-1.45 (m, 1H), 1.35-1.16 (m, 8H), 0.98-0.85 (m, 2H); $^{13}$C NMR (CDCl$_3$, 100 MHz, mixture of two diastereomers) δ 194.1, 173.1, 158.0, 157.4, 157.2, 137.3, 128.4, 127.9, 127.6, 127.5, 73.4, 69.7, 66.4, 55.6, 52.2, 48.5, 44.0, 40.7, 34.2, 34.1, 33.6, 32.9, 32.6, 32.5, 26.4, 26.1, 26.0, 25.3, 24.6; HRESIMS calcd for $C_{31}H_{46}N_4O_6Na$ 593.3315, found 593.3318.

N4-[(1R)-2-[1-[(benzyloxy)methyl]-3-(4-fluoroanilino)-2,3-dioxopropyl]amino-1-(cyclohexylmethyl)-2-oxoethyl]-4-morpholinecarboxamide (72)

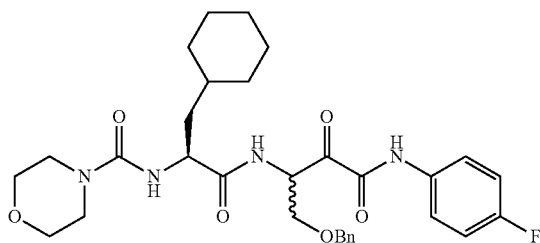

72

$^1$H NMR (CDCl$_3$, 400 MHz, mixture of two diastereomers) δ 8.60 (s, 1H), 7.57-7.54 (m, 2H), 7.24-7.16 (m, 5H), 7.05 (t, J=7.8 Hz, 2H), 6.95 (d, J=6.8 Hz, 1H), 5.57-5.53 (m, 1H), 4.90-4.85 (m, 1H), 4.50-4.39 (m, 3H), 4.25-4.22 (m, 1H), 3.82 (dd, J=9.7, 3.3 Hz, 1H), 3.66-3.61 (m, 4H), 3.34-3.33 (m, 4H), 1.78-1.65 (m, 8H), 1.53-1.46 (m, 1H), 1.40-1.30 (m, 1H), 1.23-1.14 (m, 1H), 1.00-0.84 (m, 2H); $^{13}$C NMR (CDCl$_3$, 100 MHz, mixture of two diastereomers) δ 193.9, 173.2, 157.4, 157.3, 156.7, 137.1, 132.1, 128.4, 127.9, 127.7, 127.6, 121.7, 121.6, 116.1, 115.9, 73.4, 69.5, 69.4, 66.4, 55.4, 55.3, 52.1, 51.9, 44.1, 44.0, 40.5, 34.2, 34.1, 33.6, 32.9, 26.4, 26.2, 26.1; HRESIMS calcd for $C_{31}H_{39}N_4O_6NaF$ 605.2751, found 605.2768.

N4-[(1R)-2-[1-[(benzyloxy)methyl]-3-(4-chloroanilino)-2,3-dioxopropyl]amino-1-(cyclohexylmethyl)-2-oxoethyl]-4-morpholinecarboxamide (71)

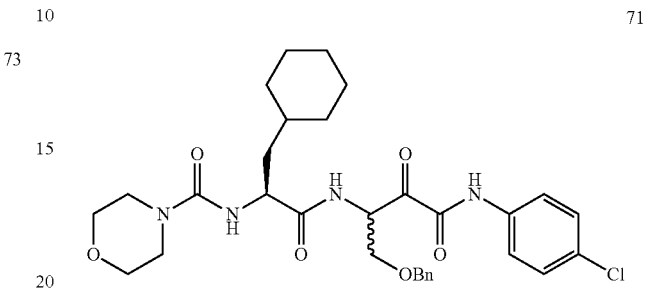

71

$^1$H NMR (CDCl$_3$, 400 MHz, mixture of two diastereomers) δ 8.80 and 8.77 (s, 1H), 7.55-7.50 (m, 2H), 7.41 (d, J=7.5 Hz, 0.4H), 7.31-7.26 (m, 2H), 7.23-7.15 (m, 5H), 5.57-5.51 (m, 1H), 5.11 and 5.10 (d, J=5.2 and 5.3 Hz, 1H), 4.56-4.36 (m, 3H), 4.22-4.17 (m, 1H), 3.81-3.77 (m, 1H), 3.62-3.58 (m, 4H), 3.37-3.27 (m, 4H), 2.02-1.60 (m, 7H), 1.53-1.46 (m, 1H), 1.37-1.28 (m, 1H), 1.25-1.06 (m, 2H), 0.97-0.83 (m, 2H); $^{13}$C NMR (CDCl$_3$, 100 MHz, mixture of two diastereomers) δ193.8, 173.5, 157.5, 157.3, 156.7, 156.6, 137.0, 134.7, 130.5, 129.2, 128.4, 127.9, 127.7, 127.6, 121.3, 121.2, 73.4, 69.5, 69.4, 66.4, 55.3, 55.2, 52.1, 51.9, 44.1, 44.0, 40.3, 40.0, 34.2, 34.1, 33.5, 32.8, 26.4, 26.1, 26.0; HRESIMS calcd for $C_{31}H_{39}N_4O_6NaCl$ 621.2456, found 621.2444.

N4-[(1R)-2-[1-[(benzyloxy)methyl]-3-(5,8-dihydro-2-naphthalenylamino)-2,3-dioxopropyl]amino-1-(cyclohexylmethyl)-2-oxoethyl]-4-morpholinecarboxamide (76)

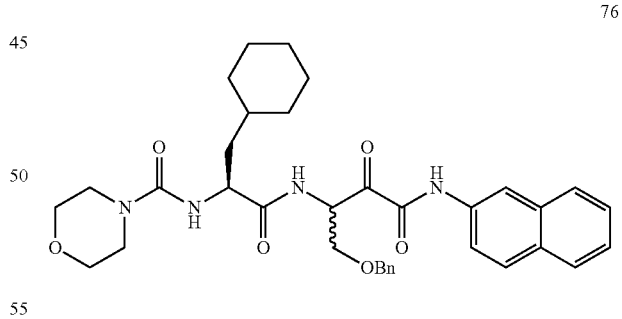

76

$^1$H NMR (CDCl$_3$, 400 MHz) δ 8.77 (s, 1H), 8.28 (d, J=1.8 Hz, 1H), 7.83-7.76 (m, 3H), 7.51-7.41 (m, 3H), 7.22-7.17 (m, 5H), 5.61 (ddd, J=7.6, 3.4, 1.7 Hz, 1H), 4.88 (d, J=8.1 Hz, 1H), 4.54-4.49 (m, 1H), 4.46 (d, J=5.5 Hz, 1H), 4.29 (dd, J=9.8, 3.7 Hz, 1H), 3.85 (d, J=9.8, 3.3 Hz, 1H), 3.68-3.63 (m, 4H), 3.38-3.31 (m, 4H), 1.79-1.61 (m, 7H), 1.54-1.46 (m, 1H), 1.35-1.31 (m, 1H), 1.23-1.10 (m, 2H), 0.99-0.84 (m, 2H); $^{13}$C NMR (CDCl$_3$, 100 MHz, mixture of two diastereomers) δ194.1, 173.6, 173.5, 157.5, 157.4, 156.9, 156.8, 137.1, 137.0 133.5, 131.1, 129.0, 128.9, 128.4, 127.8, 127.7, 127.6, 127.5, 126.7, 126.6, 126.5, 119.5, 119.4, 117.4, 117.3, 73.4, 73.3, 69.7, 69.5, 66.4, 55.4, 55.3, 52.1, 52.0, 44.1, 44.0, 40.3, 40.0, 34.2, 34.1, 33.6, 33.5, 32.8, 32.7, 26.4, 26.1, 26.0; HRESIMS calcd for C$_{35}$H$_{42}$N$_4$O$_6$Na 637.3002, found 637.3004.

Methyl 2-[4-(benzyloxy)-3-(((2R)-3-cyclohexyl-2-[(morpholinocarbonyl)amino]propanoylamino)-2-oxobutanoyl]amino-3-methylbutanoate (69)

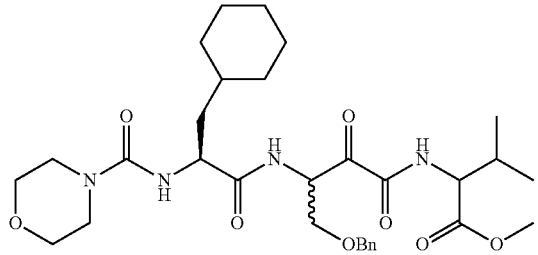

69

$^1$H NMR (CDCl$_3$, 400 MHz, mixture of two diastereomers) δ 7.35-7.30 (m, 1H), 7.27-7.26 (m, 1H), 7.23-7.15 (m, 3H), 5.47-5.41 (m, 1H), 5.11 (s, 1H), 4.46-4.35 (m, 3H), 4.19 and 4.12 (ddd and dd, J=9.7, 3.5, 2.3 and 9.8, 3.7 Hz, 1H), 3.76-3.73 (m, 1H), 3.71 and 3.70 (s, 3H), 3.66-3.57 (m, 4H), 3.40-3.18 (m, 4H), 2.23-2.12 (m, 1H), 1.74-1.44 (m, 7H), 1.38-1.04 (m, 4H), 0.97-0.82 (m, 8H); $^{13}$C NMR (CDCl$_3$, 100 MHz, mixture of two diastereomers) δ193.0, 173.3, 171.0, 158.8, 158.7, 157.4, 137.1, 128.3, 127.8, 127.6, 127.5, 127.4, 73.3, 73.2, 69.8, 69.4, 66.3, 57.2, 57.1, 55.5, 52.3, 52.2, 52.1, 52.0, 44.0, 40.4, 39.8, 34.1, 34.0, 33.5, 32.7, 31.4, 31.3, 29.6, 26.3, 26.1, 26.0, 18.8, 17.7, 17.6; HRESIMS calcd for C$_{31}$H$_{46}$N$_4$O$_8$Na 625.3213, found 625.3222.

N4-[(1R)-2-[1-[(benzyloxy)methyl]-3-(isopropylamino)-2,3-dioxopropyl]amino-1-(cyclohexylmethyl)-2-oxoethyl]-4-morpholinecarboxamide (63)

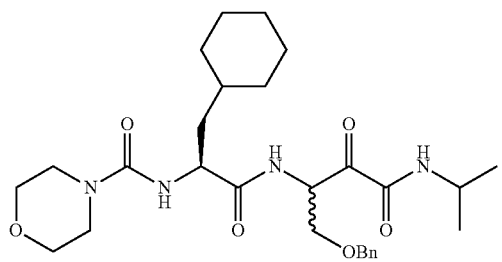

63

$^1$H NMR (CDCl$_3$, 400 MHz, mixture of two diastereomers) δ7.31-7.21 (m, 3H), 7.20-7.15 (m, 2H), 6.80-6.78 (m, 1H), 5.48-5.43 (m, 1H), 5.22 (s, 1H), 4.47-4.34 (m, 3H), 4.17 and 4.16 (dd, J=9.7, 3.1 and 9.6, 3.0 Hz, 1H), 4.02-3.95 (m, 1H), 3.76-3.68 (m, 1H), 3.60-3.59 (m, 4H), 3.35-3.27 (m, 4H), 1.74-1.45 (m, 7H), 1.38-1.31 (m, 1H), 1.25-1.05 (m, 3H), 1.15 and 1.14 (d, J=6.2 and 6.5 Hz, 6H), 0.99-0.81 (m, 2H); $^{13}$C NMR (CDCl$_3$, 100 MHz, mixture of two diastereomers) δ194.0, 173.4, 158.2, 158.0, 157.4, 157.3, 137.3, 128.3, 127.7, 127.5, 127.4, 73.3, 73.2, 69.6, 69.5, 66.3, 55.5, 55.4, 52.1, 52.0, 44.0, 41.6, 40.4, 40.0, 34.1, 34.0, 33.5, 32.8, 29.6, 26.3, 26.1, 26.0, 22.2; LRFABMS calcd for C$_{28}$H$_{43}$N$_4$O$_6$ 531.31, found 531.31.

N4-[(1R)-2-[1-[(benzyloxy)methyl]-3-(cyclopentylamino)-2,3-dioxopropyl]amino-1-(cyclohexylmethyl)-2-oxoethyl]-4-morpholinecarboxamide (74)

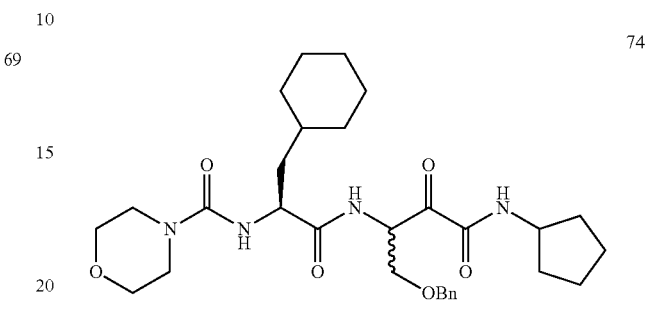

74

$^1$H NMR (CDCl$_3$, 400 MHz, mixture of two diastereomers) δ 7.31-7.25 (m, 3H), 7.21-7.19 (m, 2H), 7.03 and 6.82 (d, J=7.7 and 7.9 Hz, 1H), 6.78 (d, J=7.4 Hz, 1H), 4.48-5.46 (m, 1H), 4.90 and 4.85 (d, J=7.9 and 7.9 Hz, 1H), 4.49-4.39 (m, 1H), 4.21 (dd, J=9.8, 3.4 Hz, 1H), 4.17-4.09 (m, 1H), 3.78 (dd, J=9.7, 3.2 Hz, 1H), 3.66-3.63 (m, 4H), 3.34-3.32 (m, 4H), 2.04-1.95 (m, 2H), 1.77-1.59 (m, 12H), 1.52-1.39 (m, 2H), 1.33-1.09 (m, 3H), 1.00-0.84 (m, 2H); $^{13}$C NMR (CDCl$_3$, 100 MHz, mixture of two diastereomers) δ193.9 173.4, 158.6, 158.4, 157.4, 157.3, 137.2, 128.2, 127.7, 127.4, 127.3, 73.2, 73.1, 69.6, 69.5, 66.4, 66.3, 55.4, 55.3, 52.1, 52.0, 51.0, 47.1, 44.0, 40.3, 39.9, 34.0, 33.9, 33.5, 32.6, 26.3, 26.0, 25.9, 23.6; LRFABMS calcd for C$_{30}$H$_{45}$N$_4$O$_6$ 557.33, found 557.33.

N4-[(1R)-2-[1-[(benzyloxy)methyl]-3-(tert-butylamino)-2,3-dioxopropyl]amino-1-(cyclohexylmethyl)-2-oxoethyl]-4-morpholinecarboxamide (64)

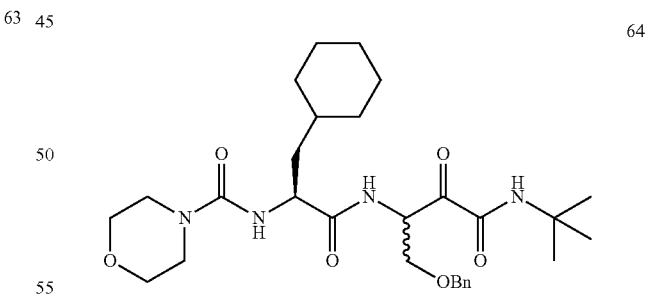

64

$^1$H NMR (CDCl$_3$, 400 MHz, mixture of two diastereomers) δ 7.30-7.24 (m, 3H), 7.21-7.17 (m, 2H), 7.11 and 6.94 (d, J=7.2 and 7.7 Hz, 1H), 6.69 (s, 1H), 5.48-5.43 (m, 1H), 5.08 and 5.04 (d, J=8.0 and 8.0 Hz, 1H), 4.48-4.35 (m, 3H), 4.17 (dd, J=9.7, 3.5 Hz, 1H), 3.75 and 3.73 (dd, J=9.5, 3.4 and 9.4, 3.1 Hz, 1H), 3.65-3.57 (m, 4H), 3.36-3.26 (m, 4H), 1.76-1.58 (m, 6H), 1.51-1.43 (m, 1H), 1.33 and 1.32 (s, 9H), 1.29-1.07 (m, 4H), 0.97-0.83 (m, 2H); $^{13}$C NMR (CDCl$_3$, 100 MHz, mixture of two diastereomers) δ194.5, 173.3, 158.2, 158.1, 157.3, 137.3, 128.3, 127.8, 127.5, 127.4, 73.3, 69.7, 66.4, 55.2, 52.1, 52.0, 51.5, 44.0, 34.1, 34.0, 33.5, 32.8, 28.2, 26.3, 26.1, 26.0; HRESIMS calcd for $C_{29}H_{44}N_4O_6Na$ 567.3159, found 567.3156.

N4-[(1R)-2-[1-[(benzyloxy)methyl]-3-(2,6-dimethylanilino)-2,3-dioxopropyl]amino-1-(cyclohexylmethyl)-2-oxoethyl]-4-morpholinecarboxamide (78)

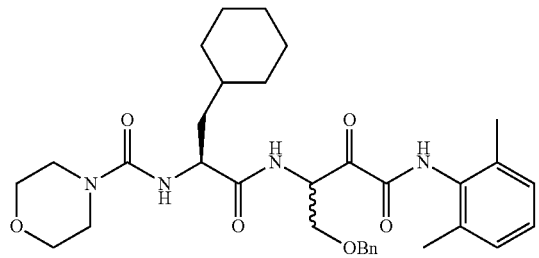

78

$^1$H NMR (CDCl$_3$, 400 MHz, mixture of two diastereomers) δ 8.18 (s, 1H), 7.32-7.25 (m, 3H), 7.23-7.21 (m, 2H), 7.17 and 6.98 (d, J=7.0 and 6.2 Hz, 1H), 7.13 and 7.11 (d, J=6.2 and 6.1 Hz, 1H), 7.07-7.06 (m, 2H), 5.58-5.55 (m, 1H), 4.89 (d, J=8.5 Hz, 1H), 4.52-4.43 (m, 3H), 4.31 and 4.29 (t, J=3.5 and 3.6 Hz, 1H), 3.83 and 3.80 (dd, J=3.1, 1.7 and 3.0, 1.6 Hz, 1H), 3.67-3.63 (m, 4H), 3.35-3.32 (m, 4H), 2.15 (s, 6H), 1.75-1.63 (m, 6H), 1.55-1.46 (m, 1H), 1.39-1.10 (m, 4H), 1.02-0.84 (m, 2H); $^{13}$C NMR (CDCl$_3$, 100 MHz, mixture of two diastereomers) δ194.3, 194.1, 173.5, 157.5, 157.4, 157.2, 137.2, 135.0, 132.0, 128.3, 128.2, 127.8, 127.7, 127.4, 73.4, 70.1, 66.6, 66.3, 55.8, 55.7, 52.2, 52.0, 43.9, 43.9 40.4, 40.1, 34.1, 34.0, 33.6, 33.5, 32.8, 32.7, 26.3, 26.1, 26.0, 18.2; HRESIMS calcd for $C_{33}H_{44}N_4O_6Na$ 615.3159, found 615.3157.

N4-[(1R)-2-[1-[(benzyloxy)methyl]-3-(4-methoxyanilino)-2,3-dioxopropyl]amino-1-(cyclohexylmethyl)-2-oxoethyl]-4-morpholinecarboxamide (79)

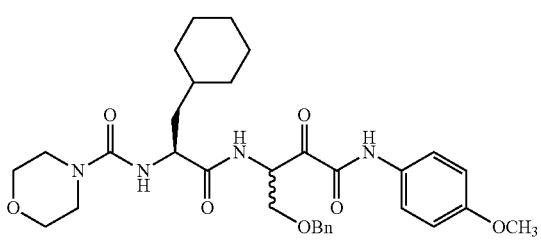

79

$^1$H NMR (CDCl$_3$, 400 MHz, mixture of two diastereomers) δ 8.56 (s, 1H), 7.51 and 7.50 (d, J=9.0 and 9.1 Hz, 2H), 7.23-7.15 (m, 5H), 7.88 and 6.87 (d, J=9.0 and 9.2 Hz, 2H), 5.58-5.55 (m, 1H), 5.95 (s, 1H), 4.52-4.39 (m, 3H), 4.26 and 4.24 (d, =3.5 and 3.4 Hz, 1H), 3.83-3.81 (m, 1H), 3.79 (s, 3H), 3.68-3.61 (m, 4H), 3.34-3.33 (m, 4H), 1.78-1.62 (m, 6H), 1.51-1.46 (m, 1H), 1.38-1.11 (m, 4H), 1.00-0.84 (m, 2H); $^{13}$C NMR (CDCl$_3$, 100 MHz, mixture of two diastereomers) δ194.2, 173.4, 157.5, 157.1, 156.3, 156.2, 137.1, 129.2, 128.4, 127.8, 127.6, 127.5, 121.6, 121.5, 114.3, 73.3, 69.6, 69.5, 66.4, 55.4, 55.1, 52.0, 44.1, 34.1, 34.0, 33.5, 32.8, 32.7, 26.3, 26.1, 26.0; HRFABMS calcd for $C_{32}H_{43}N_4O_7$ 595.3132, found 595.3134.

N4-[(1R)-2-[1-[(benzyloxy)methyl]-3-(4-methoxyanilino)-2,3-dioxopropyl]amino-1-(cyclohexylmethyl)-2-oxoethyl]-4-morpholinecarboxamide (77)

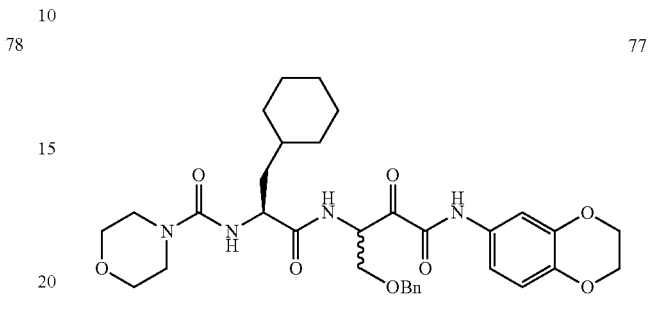

77

$^1$H NMR (CDCl$_3$, 400 MHz, mixture of two diastereomers) δ 8.52 (s, 1H), 7.26-7.18 (m, 6H), 7.00-6.97 (m, 2H), 6.82 and 6.81 (d, J=8.7 and 8.7 Hz, 1H), 4.97 and 4.95 (d, J=8.0 and 8.0 Hz, 1H), 4.50-4.38 (m, 3H), 4.23-4.21 (m, 5H), 3.81 and 3.79 (t, =3.8 and 3.6 Hz, 1H), 3.64-3.62 (m, 4H), 3.33-3.32 (m, 4H), 1.79-1.61 (m, 6H), 1.53-1.45 (m, 1H), 1.38-1.34 (m, 1H), 1.29-1.08 (m, 3H), 0.99-0.85 (m, 2H); $^{13}$C NMR (CDCl$_3$, 100 MHz, mixture of two diastereomers) δ194.1, 173.3, 157.4, 157.3, 156.3, 156.2, 143.6, 141.2, 137.2, 137.1, 129.8, 128.4, 127.9, 127.6, 127.5, 117.4, 113.5, 109.6, 73.4, 69.6, 69.5, 66.4, 64.4, 64.3, 55.4, 55.3, 52.1, 52.0, 44.1, 44.0, 40.4, 40.0, 34.2, 34.1, 33.5, 32.9, 32.8, 26.4, 26.1, 26.0; HRESIMS calcd for $C_{33}H_{42}N_4O_8Na$ 645.2900, found 645.2886.

N4-[(1R)-2-(1-[(benzyloxy)methyl]-3-[(1-methylbutyl)amino]-2,3-dioxopropyl amino)-1-(cyclohexylmethyl)-2-oxoethyl]-4-morpholinecarboxamide (65)

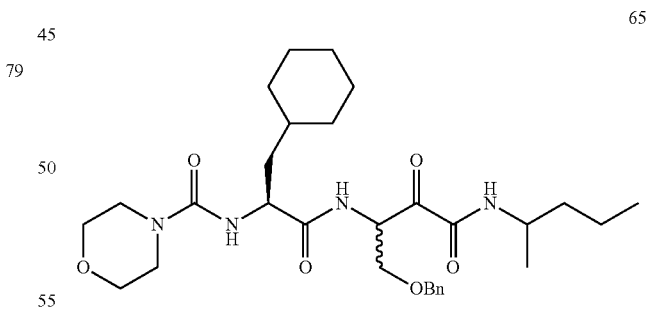

65

1H NMR (CDCl3, 400 MHz, mixture of two diastereomers) δ 7.31-7.26 (m, 3H), 7.20-7.18 (m, 3H), 7.04 and 6.84 (d, J=7.5 and 7.6 Hz, 1H), 6.65 and 6.58 (d, J=8.4 and 8.8 Hz, 1H), 5.51-5.46 (m, 1H), 4.92 and 4.88 (d, J=7.6 and 8.5 Hz, 1H), 4.48-4.38 (m, 3H), 4.25-4.20 (m, 1H), 3.95-3.88 (m, 1H), 3.76 (dd, J=9.8, 3.4 Hz, 1H), 3.65-3.61 (m, 4H), 3.34-3.32 (m, 4H), 1.78-1.54 (m, 7H), 1.52-1.06 (m, 10H), 1.00-0.82 (m, 6H); 13C NMR (CDCl3, 100 MHz, mixture of two diastereomers) δ194.1, 173.3, 158.3, 157.4, 157.3, 137.3, 128.3, 127.8, 127.5, 127.4, 73.3, 69.8, 66.4, 55.6, 55.5, 52.5, 52.1, 52.0, 45.3, 44.0, 40.5, 40.0, 38.6, 34.1, 34.0, 33.5, 32.8, 27.1, 26.3, 26.1, 26.0, 20.4, 19.1, 19.0, 13.7, 10.1; HRMS (ESI) calcd for C30H46N4O6Na 581.3315, found 581.3325.

N4-[(1R)-2-[1-[(benzyloxy)methyl]-2,3-dioxo-3-(phenethylamino)propyl]amino-1-(cyclohexylmethyl)-2-oxoethyl]-4-morpholinecarboxamide (70)

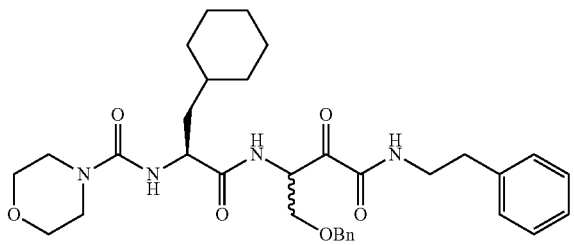

70

¹H NMR (CDCl₃, 400 MHz, mixture of two diastereomers) δ 7.31-7.24 (m, 4H), 7.23 7.14 (m, 6H), 7.08 (d, J=7.7 Hz, 0.4H), 6.96-6.89 (m, 1.6H), 5.49-5.45 (m, 1H), 4.94 and 4.90 (d, J=7.9 and 8.0 Hz, 1H), 4.49-4.37 (m, 3H), 4.20 and 4.18 (d, J=3.5, 2.5 and 3.5, 2.6 Hz, 1H), 3.78 and 3.76 (t, J=3.0 and 3.0 Hz, 1H), 3.66-3.59 (m, 4H), 3.52 and 3.52 (dd, J=13.5, 7.0 and 13.5, 7.0 Hz, 2H), 3.37-3.31 (m, 4H), 2.81 (t, J=7.3 Hz, 2H), 1.77-1.60 (m, 6H), 1.51-1.43 (m, 1H), 1.36-1.27 (m, 1H), 1.25-1.10 (m, 3H), 0.98-0.86 (m, 2H); ¹³C NMR (CDCl₃, 100 MHz, mixture of two diastereomers) δ193.7, 173.4, 159.0, 158.9, 157.4, 157.3, 138.0, 137.2, 128.6, 128.5, 128.3, 127.7, 127.5, 127.4, 126.6, 73.2, 69.6, 69.5, 66.5, 66.3, 55.5, 55.3, 52.0, 51.9, 47.1, 43.9, 40.4, 40.3, 39.9, 38.3, 35.2, 34.0, 33.9, 33.5, 32.7, 26.3, 26.1, 25.9; HRESIMS calcd for C33H44N4O6Na 615.3159, found 615.3149.

N4-[(1R)-2-(1-[(benzyloxy)methyl]-3-[(3-isopropoxypropyl)amino]-2,3-dioxopropylamino)-1-(cyclohexylmethyl)-2-oxoethyl]-4-morpholinecarboxamide (68)

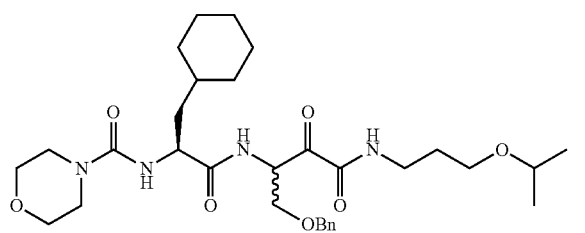

68

¹H NMR (CDCl₃, 400 MHz, mixture of two diastereomers) δ 7.72 and 7.68 (t, J=5.4 and 5.6 Hz, 1H), 7.30-7.22 (m, 3H), 7.20-7.18 (m, 2H), 7.06 and 6.89 (d, J=7.8 and 7.8 Hz, 1H), 5.50-5.46 (m, 1H), 5.01 and 4.97 (d, J=7.9 and 8.1 Hz, 1H), 4.48-4.38 (m, 3H), 4.19 (dd, J=9.8, 3.5 Hz, 1H), 3.78 and 3.76 (t, J=3.1 and 3.2 Hz, 1H), 3.69-3.62 (m, 4H), 3.56-3.49 (m, 3H), 3.40-3.32 (m, 6H), 1.79-1.58 (m, 8H), 1.50-1.43 (m, 1H), 1.38-1.26 (m, 1H), 1.24-1.14 (m, 9H), 0.98-0.84 (m, 2H); ¹³C NMR (CDCl₃, 100 MHz, mixture of two diastereomers) δ193.6, 193.5, 173.4, 158.9, 158.8, 157.4, 157.2, 137.3, 128.3, 127.7, 127.5, 127.4, 73.2, 71.9, 69.6, 69.5, 67.0, 66.8, 66.6, 66.5, 66.4, 55.5, 55.4, 52.1, 52.0, 44.0, 40.4, 40.0, 38.5, 38.4, 34.1, 34.0, 33.5, 33.4, 32.9, 32.7, 28.7, 28.6, 26.3, 26.1, 25.9; HRESIMS calcd for C31H48N4O7Na 611.3421, found 611.3422.

N4-[(1R)-2-(3-[(1H-1,2,3-benzotriazol-1-ylmethyl)amino]-1-[(benzyloxy)methyl]-2,3-dioxopropylamino)-1-(cyclohexylmethyl)-2-oxoethyl]-4-morpholinecarboxamide (75)

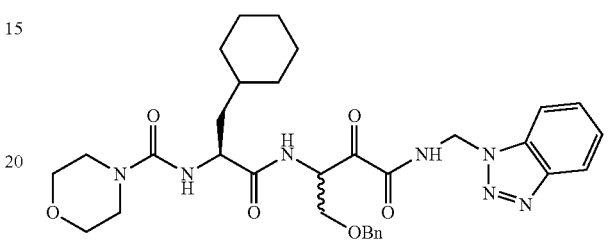

¹H NMR (CDCl3, 400 MHz, mixture of two diastereomers) δ 8.21-8.18 (m, 1H), 8.02-8.00 (m, 1H), 7.80 (dd, J=8.5, 0.6 Hz, 1H), 7.51-7.46 (m, 1H), 7.36 (t, J=7.8 Hz, 1H), 7.19-7.14 (m, 3H), 7.06-6.98 (m, 2H), 6.09 and 6.06 (d, J=7.0 Hz, 2H), 5.49-5.42 (m, 1H), 4.92 (d, J=7.8 Hz, 1H), 4.51-4.40 (m, 1H), 4.30 and 4.29 (dd and s, J=20.5, 12.0 Hz, 2H), 4.15-4.09 (m, 1H), 3.75 and 3.73 (dd, J=5.2, 3.4 and 5.3, 3.4 Hz, 1H), 3.67-3.58 (m, 4H), 3.37-3.28 (m, 4H), 1.66-1.52 (m, 7H), 1.46-1.37 (m, 1H), 1.30-1.20 (m, 1H), 1.19-1.06 (m, 2H), 0.92-0.81 (m, 2H); ¹³C NMR (CDCl₃, 100 MHz, mixture of two diastereomers) δ193.1, 173.7, 173.6, 159.9, 159.6, 157.5, 157.3, 145.9, 136.9, 136.8, 132.3, 128.4, 128.3, 128.1, 127.8, 127.5, 127.4, 124.4, 119.7, 110.4, 73.3, 69.5, 66.4, 55.5, 55.4, 52.0, 51.9, 50.5, 44.0, 40.2, 39.8, 34.1, 33.9, 33.5, 33.4, 32.7, 32.6, 26.3, 26.1, 25.9; HRMS (FAB) calcd for C32H42N7O6 620.3197, found 620.3194.

Compound 99 was synthesized as show below:

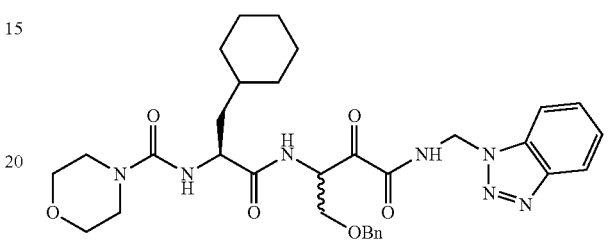

i

-continued

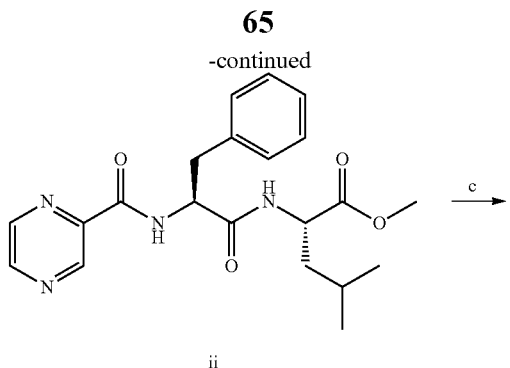

ii

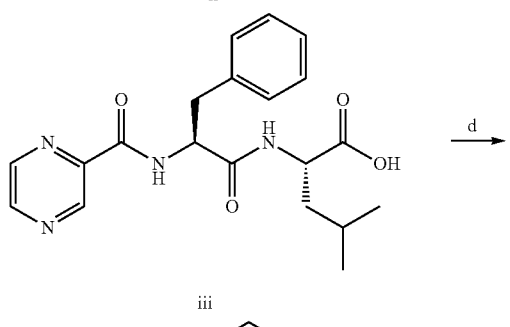

iii

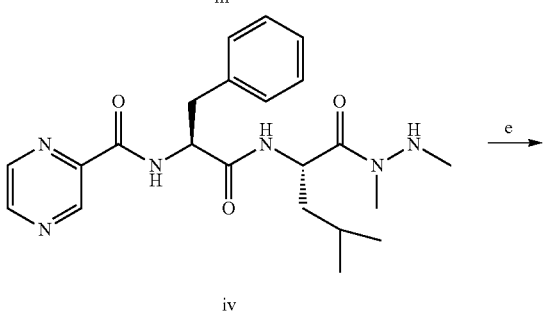

99

Methyl 2-(2-[(tert-butoxycarbonyl)amino]-3-phenyl-propanoylamino)-4-methyl pentanoate (i)

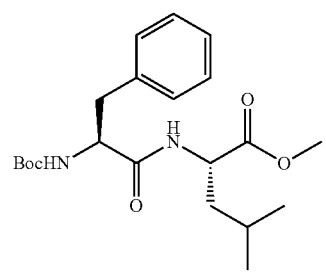

i

Boc-Phe-OH (2 g, 13.77 mmol), H-Leu-OMe (11 g, 41.32 mmol), HOBt (5.58 g, 41.32 mmol), and HBTU (15.67 g, 41.32 mmol) were dissolved in DMF (69 mL) and then DIPEA (7.2 mL, 41.32 mmol) was added under argon. The reaction was stirred for 8 hrs at room temperature. The reaction was extracted by EtOAc and wash with 5% NaHSO₃, sat. NaHCO₃ and brine. The organic layer was dried over Na₂SO₄, and concentrated by rotary evaporation. The crude was purified by chromatography (silica, 4/1: Hexane/EtOAc, Rf=0.3) to give methyl 2-(2-[(tert-butoxycarbonyl)amino]-3-phenylpropanoylamino)-4-methylpentanoate as white solid (4.5 g, 8%).

Methyl 4-methyl-2-(3-phenyl-2-[(2-pyrazinylcarbonyl)amino]propanoylamino) pentanoate (ii)

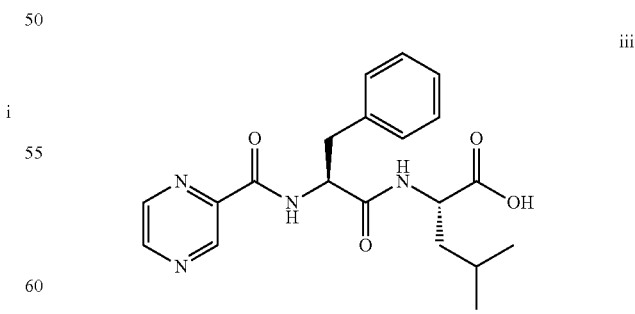

ii

Methyl 2-(2-[(tert-butoxycarbonyl)amino]-3-phenylpropanoylamino)-4-methyl pentanoate (2.24 g, 5.69 mmol) was dissolved in 33% TFA in DCM. The solution was stirred for 2 h and then concentrated to remove TFA. 2-Pyrazinecarboxylic acid (1.06 g, 8.55 mmol) was dissolved in THF (43 mL) and then cooled to −10° C. N-Methylmorpholine (2.19 mL, 19.95 mmol) and isobutyl chloroformate (1.12 mL, 8.55 mmol) were added dropwise. After N-Methylmorpholine HCl salt was precipitated, the crude compound was dissolved in THF (29 mL). The solution was stirred for 2 h at r.t. The solution was extracted by EtOAc and washed with water, saturated sodium bicarbonate solution, and brine. The organic layer was dried over Na₂SO₄, filtered, and concentrated by rotary evaporation. Purification by chromatography (silica, 2/1: Hexane/EtOAc, Rf=0.3) afforded methyl 4-methyl-2-(3-phenyl-2-[(2-pyrazinylcarbonyl)amino]propanoylamino) pentanoate (1.9 g, 90%).

4-Methyl-2-(3-phenyl-2-[(2-pyrazinylcarbonyl)amino]propanoylamino) pentanoic acid (iii)

iii

Methyl 4-methyl-2-(3-phenyl-2-[(2-pyrazinylcarbonyl)amino]propanoylamino) pentanoate (1.7 g, 4.27 mmol) was dissolved in THF (21 mL). 1 M LiOH (21 mL) was added. The solution was stirred for 6 h and concentrated by rotary evaporation. The pH value of water layer was adjusted to 2 by using HCl aqueous solution. The solution was extracted by EtOAc and washed with water and brine. The organic layer was dried over $Na_2SO_4$, filtered, and concentrated by rotary evaporation to afford 4-methyl-2-(3-phenyl-2-[(2-pyrazinyl-carbonyl)amino]propanoylamino)pentanoic acid as white solid (1.6 g, 97%).

N2-[1-benzyl-2-(1-[(1,2-dimethylhydrazino) carbonyl]-3-methylbutylamino)-2-oxoethyl]-2-pyrazinecarboxamide (iv)

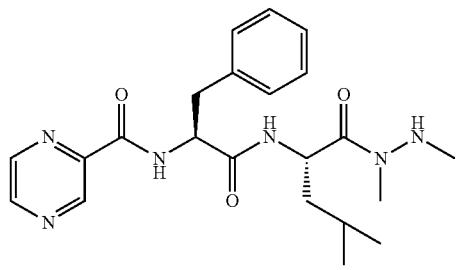

iv

4-Methyl-2-(3-phenyl-2-[(2-pyrazinylcarbonyl)amino]propanoylamino) pentanoic acid (200 mg, 0.52 mmol) was dissolved in THF (1.2 mL). N-Methylmorpholine (0.057 mL, 0.52 mmol) was added, and the resulting clear solution was cooled to −10° C. Isobutyl chloroformate (0.068 mL, 0.52 mmol) was added dropwise to cause N-Methylmorpholine HCl salt precipitation. N,N'-dimethylhydrazine hydrochloride salt (346 mg, 2.6 mmol) was dissolved in 3N NaOH (1.7 mL). The resulting mixture was added to the solution and stirred for 1 h. The solution was extracted by EtOAc, and washed with 5% $NaHSO_3$, saturated sodium bicarbonate solution, and brine. The organic layer was dried over $Na_2SO_4$, filtered, and concentrated by rotary evaporation. Purification by chromatography (silica, 20/1: DCM/MeOH, Rf=0.3) afforded N2-[1-benzyl-2-(1-[(1,2-dimethylhydrazino) carbonyl]-3-methylbutylamino)-2-oxoethyl]-2-pyrazinecarboxamide as a pale yellow solid (197 mg, 89%).

N2-[1-benzyl-2-(1-[(2-cyano-1,2-dimethylhydrazino)carbonyl]-3-methylbutylamino)-2-oxoethyl]-2-pyrazinecarboxamide (99)

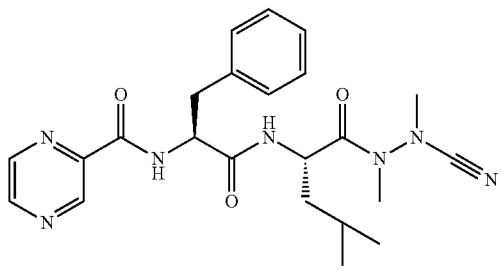

99

N2-[1-benzyl-2-(1-[(1,2-dimethylhydrazino)carbonyl]-3-methylbutylamino)-2-oxoethyl]-2-pyrazinecarboxamide (100 mg, 0.23 mmol) and sodium acetate (53 mg, 0.64 mmol) were dissolved in methanol (1 mL). Cyanogen bromide (49 mg, 0.46 mmol) was added and the solution was stirred for 4 h. Methanol was concentrated by rotary evaporation. The pH value was adjusted (5% $NaHSO_3$) to 1-2. The solution was extracted by EtOAc, and washed with water and brine. The organic layer was dried over $Na_2SO_4$, filtered, and concentrated by rotary evaporation. Purification by chromatography (silica, 1/1: Hexane/EtOAc, Rf=0.3) afforded N2-[1-benzyl-2-(1-[(2-cyano-1,2-dimethylhydrazino)carbonyl]-3-methylbutylamino)-2-oxoethyl]-2-pyrazinecarboxamide as pale yellow solid (67 mg, 65%).

$^1$H NMR (CDCl3, 400 MHz) δ 9.34 (d, J=1.2 Hz, 1H), 8.73 (d, J=2 Hz, 1H), 8.51 (dd, J=2.0, 1.2 Hz, 1H), 7.28-7.10 (m, 5H), 5.00 (dd, J=14.2, 7.6 Hz, 1H), 4.87 (dd, J=14.4, 7.2 Hz, 1H), 3.21 (s, 3H), 3.17 (s, 3H), 3.09 (m, 2H), 1.59-1.40 (m, 3H), 0.92 (d, J=6.4 Hz, 3H), 0.87 (d, J=6.4 Hz, 3H); $^{13}$C NMR (CDCl$_3$, 75 MHz) δ 173.71, 170.68, 162.86, 147.49, 144.28, 143.76, 142.71, 136.06, 129.28, 128.52, 127.01, 113.40, 53.97, 47.74, 41.03, 40.84, 38.22, 30.41, 24.74, 23.02, 21.34; LRMSEI calcd for $C_{23}H_{29}N_7O_3$ 451.23, found 452.2 (M+1), 474.2 (M+23).

Bioassays
Purification of Cathepsin S

Human cathepsin S was synthesized as a pre-proenzyme containing an N-terminal secretion signal, a pro-sequence region, and a mature polypeptide. In cells, the mature cathepsin S protein was generated by acid-activated autoprocessing of proenzyme where the 99-residue pro-sequence region was removed. To obtain recombinant cathepsin S, cDNA encoding procathepsin S (amino acids 17-331) was cloned into the vector pET23a and the protein with a His$_6$ tag (H) engineered at the C-terminus was expressed in E. coli. Recombinant procathepsin S (~35 kDa) was abundantly recovered in the soluble fraction of total bacterial lysates as well as in the solubilized inclusion bodies. Following refolding, procathepsin S was added with acetic acid (pH 4.5), resulting in the generation of cathepsin S with a molecular mass of 24.6 kDa. The identity of cathepsin S was also confirmed by Western blotting with human cathepsin S-specific polyclonal antibodies. The specific activity of recombinant cathepsin S was determined to be 0.26 U/mg by fluorometry using Z-VVR-AMC as a substrate.

Cathepsin S Assay

The activity of recombinant cathepsin S was measured using benzyloxycarbonyl-valine-valine-arginine-7-amido-4-methylcoumarin (Z-VVR-AMC) as the substrate. The assay mixture consisted of 50 mM MES buffer (pH 6.5), 1 mM DTT, 2.5 mM EDTA, 5 μM substrate and 50 nM enzyme solution in a total volume of 200 μl. The release of the fluorophore AMC from the synthetic peptide substrate Z-VVR-AMC was then monitored. Fluorescence intensity of AMC was measured continuously at 37° C. using a spectrophotometer (model LS55, Perkin Elmer instruments) with excitation and emission settings of 370 nm and 460 nm, respectively. A microplate-based screening procedure was used to identify potential cathepsin S inhibitors. Test compounds were dissolved in dimethyl sulfoxide (DMSO) to a final concentration of 100 μM and incubated with recombinant activated enzyme at 37° C. for 10 min before initiating the reaction with the addition of substrate Z-VVR-AMC as previously described. For IC$_{50}$ determination, the test compounds were 2-fold serially diluted and added to the assay mixture and AMC fluorescence intensities were measured. IC$_{50}$ was calculated using GraphPad Prism software.

Compounds 1-99 were tested and exhibited inhibitory activity. Some of them, e.g., compounds 1-56, 62-79, and 99, had IC$_{50}$ values lower than 50 nm.

Growth Inhibition Assay

Logarithmic phase cells were seeded in a 96-well plate and incubated overnight prior to addition of the designated compounds. After incubation with different concentrations of the tested compounds for three generative times, cells were incubated with medium containing 0.4 mg/mL 3-(4,5-dimethylthiazol-2-yl)-2,5-diphenyl tetrazolium bromide (MTT) for 2 hours. The conversion of MTT to formazan by metabolically viable cells was measured by the absorbance at 570 nm in a 96-well microtiter plate reader. The percentage conversion by mock-treated control cells was used to evaluate the effect of the chemicals on cell growth and to determine the concentration that inhibited 50% of growth ($GI_{50}$).

Cancer Cells Migration Assay

The cancer cell migration assay was performed in 96-wll-MultiScreen-MIC plates (Millipore) with 8 µm-pore-sized polycarbonate membrane. Briefly, highly-metastatic human lung adenocarcinoma CL1-5 cells were placed onto the upper chamber ($2\times10^4$ cells/well) with tested compounds in complete medium (RPMI 1640 medium containing 1% FBS) and only medium placed onto the lower chamber. The chamber culture was incubated for 24 h at 37° C. and, then, the non-migrated cells were washed off the upper surface of the membrane. The migrated cells on the bottom side were dissociated with Cell Detachment Buffer (Chemicon, Inc.), lysed and stained for nucleic acids with CyQuant GR dye (Molecular Probes). The signal intensities were measured using a fluorescence reader (VICTORTIM 1420 Multilabel Counter, Wallac) at excitation wavelength of 485 nm and emission wavelength of 535 nm (1 sec). The result was presented as the average values from three independent experiments performed in duplicates.

Compounds 1-4, 7, 10, 14, 16, 21-25, 30, 36, 43, 45, 49, 56, 62, 64, 66, 67, and 70-72 inhibited CL-15 cell migration by 25% or more.

Similarly, Compounds 1 and 118 were tested against human A2058 melanoma cells and pancreatic cancer cells. Compound 1 effectively inhibited migratory and invasice abilities of A2058 melanoma cells and Compound 118 effective inhibited migratory and invasice abilities of pancreatic cancer cells HUVECs Migration Assay HUVECs migration was determined using an in vitro wound healing assay. Briefly, HUVECs were placed into 6-well gelatin-coated plates ($3\times10^5$ cells/well) and allowed to grow into a confluent cell monolayer for 24 hours. A wound was created by scraping the confluent cell monolayer with a pipette tip to create an empty space. After washing with PBS to remove floating cells, medium containing 1% FBS and 20 ng/ml VEGF was added with various concentrations of tested compounds. After 24-hour incubation, cell migration was quantified by counting the number of cells migrating from the wound edge into the empty space. The viability of HUVECs was determined by MTT assay in duplicated wells.

Compounds 2-4, 9, 16, 21-25, 27, 28, 30, 36, 43, 45, and 48 inhibited HUVECs migration by 25% or more.

In Vivo Assay

BALB/cAnN-Foxn1nu/CrlNarl female mice were inoculated with A2058 melanoma cells. On day 7, 12 mice were treated i.v. with Compound 1 in DMSO (mg/kg) and 8 mice were treated with DMSO as control. The treatment was continued for 72 days. The mice were sacrificed and their lungs were weighted.

The lung weights of the compound-treated mice were significantly lower than those of the non-compound-treated mice (0.471 g vs. 0.671 g). This indicates that Compound 1 effectively inhibited cancer growth in A2058 inoculated mice.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A compound of formula (I):

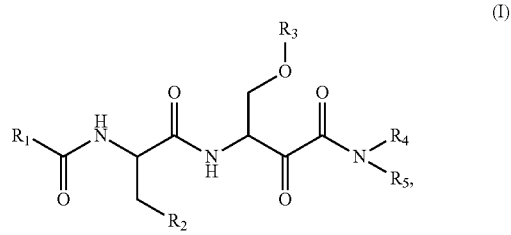

wherein $R_1$ is H, alkyl, alkenyl, alkynyl, cycloalkyl, cycloalkenyl, heterocycloalkyl, heterocycloalkenyl, aryl, heteroaryl, $OR_a$, $SR_a$, $NR_aR_b$, $N(R_a)C(O)R_b$, $N(R_a)C(O)OR_b$, $C(O)R_a$, $COOR_a$, $OC(O)R_a$, $C(S)R_a$, $C(O)NR_aR_b$, $C(S)NR_aR_b$, $N(R_a)C(S)R_b$, or $N(R_a)N(R_b)C(O)R_c$, in which each of $R_a$, $R_b$, and $R_c$, independently, is H, alkyl, alkenyl, alkynyl, cycloalkyl, cycloalkenyl, heterocycloalkyl, heterocycloalkenyl, aryl, or heteroaryl, or $R_a$ and $R_b$ together with the nitrogen atom or nitrogen atoms to which they are attached form heterocycloalkyl, heterocycloalkenyl, or heteroaryl;

each of $R_2$ and $R_3$, independently, is H, cycloalkyl, cycloalkenyl, heterocycloalkyl, heterocycloalkenyl, aryl, heteroaryl, or alkyl optionally substituted with cycloalkyl, cycloalkenyl, heterocycloalkyl, heterocycloalkenyl, aryl, or heteroaryl; and each of $R_4$ and $R_5$, independently, is H, alkyl, alkenyl, alkynyl, cycloalkyl, cycloalkenyl, heterocycloalkyl, heterocycloalkenyl, aryl, or heteroaryl, or $R_4$ and $R_5$ together with the nitrogen atom to which they are attached form heterocycloalkyl, heterocycloalkenyl, or heteroaryl.

2. The compound of claim 1, wherein the compound is of the following formula:

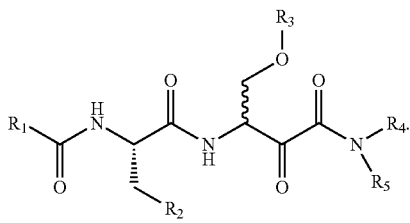

3. The compound of claim 2, wherein $R_2$ is cycloalkyl or aryl.

4. The compound of claim 3, wherein $R_2$ is cyclohexyl or phenyl.

5. The compound of claim 4, wherein $R_3$ is alkyl optionally substituted with cycloalkyl, heterocycloalkyl, aryl, or heteroaryl.

6. The compound of claim 5, wherein $R_3$ is benzyl.

7. The compound of claim 6, wherein one of $R_4$ and $R_5$ is H and the other of $R_4$ and $R_5$ is cycloalkyl, cycloalkenyl, heterocycloalkyl, heterocycloalkenyl, aryl, or heteroaryl, or alkyl optionally substituted with cycloalkyl, cycloalkenyl, heterocycloalkyl, heterocycloalkenyl, aryl, heteroaryl, $OR_d$, $C(O)R_d$, $COOR_d$, or $OC(O)R_d$, in which $R_d$ is H, alkyl, alkenyl, alkynyl, cycloalkyl, cycloalkenyl, heterocycloalkyl, heterocycloalkenyl, aryl, or heteroaryl.

8. The compound of claim 7, wherein the other of $R_4$ and $R_5$ is alkyl optionally substituted with aryl or $COOR_d$, or phenyl optionally substituted with halo or fused with heterocycloalkyl.

9. The compound of claim 2, wherein the compound is any of compounds 1-79.

10. A method for treating cancer, comprising administering to a subject in need thereof an effective amount of a compound of claim 1.

11. A pharmaceutical composition, comprising a pharmaceutically acceptable carrier and a compound of claim 1.

12. The compound of claim 1, wherein $R_2$ is isopropyl or cyclohexyl; $R_3$ is benzyl; $R_4$ is H; and $R_5$ is aryl or alkyl, in which each of aryl and alkyl is, independently, optionally substituted with cycloalkyl, cycloalkenyl, heterocycloalkyl, heterocycloalkenyl, aryl, heteroaryl, $OR_d$, $C(O)R_d$, $COOR_d$, or $OC(O)R_d$, $R_d$ being H, alkyl, alkenyl, alkynyl, cycloalkyl, cycloalkenyl, heterocycloalkyl, heterocycloalkenyl, aryl, or heteroaryl.

13. The compound of claim 12, wherein the compound is of the following formula:

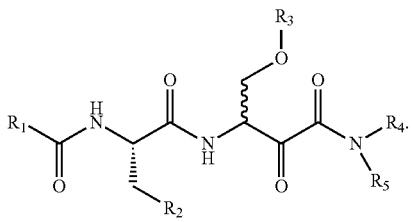

14. The compound of claim 12, wherein $R_1$ is alkyl, alkenyl, alkynyl, cycloalkyl, heterocycloalkyl, heterocycloalkenyl, aryl, heteroaryl, or $C(O)R_a$, in which $R_a$ is alkyl, alkenyl, alkynyl, cycloalkyl, cycloalkenyl, heterocycloalkyl, heterocycloalkenyl, aryl, or heteroaryl.

* * * * *